United States Patent
Wang et al.

(10) Patent No.: US 11,814,389 B2
(45) Date of Patent: Nov. 14, 2023

(54) CRYSTALLINE FORM OF (S)-7-(1-ACRYLOYLPIPERIDIN-4-YL)-2-(4-PHENOXYPHENYL)-4,5,6,7-TETRA-HYDROPYRAZOLO[1,5-A]PYRIMIDINE-3-CARBOXAMIDE, PREPARATION, AND USES THEREOF

(71) Applicant: BEIGENE SWITZERLAND GMBH, Basel (CH)

(72) Inventors: Zhiwei Wang, Beijing (CN); Yunhang Guo, Beijing (CN); Gongyin Shi, Beijing (CN)

(73) Assignee: BEIGENE SWITZERLAND GMBH, Basel (CH)

( * ) Notice: Subject to any disclaimer, the term of this patent is extended or adjusted under 35 U.S.C. 154(b) by 0 days.

(21) Appl. No.: 17/858,827

(22) Filed: Jul. 6, 2022

(65) Prior Publication Data

US 2022/0340584 A1    Oct. 27, 2022

Related U.S. Application Data

(63) Continuation of application No. 17/146,855, filed on Jan. 12, 2021, which is a continuation of application No. 16/325,447, filed as application No. PCT/IB2017/054955 on Aug. 15, 2017, now Pat. No. 10,927,117.

(51) Int. Cl.
| | | |
|---|---|---|
| C07D 487/04 | (2006.01) | |
| A61P 35/02 | (2006.01) | |
| A61P 35/04 | (2006.01) | |

(52) U.S. Cl.
CPC ............ *C07D 487/04* (2013.01); *A61P 35/02* (2018.01); *A61P 35/04* (2018.01); *C07B 2200/13* (2013.01)

(58) Field of Classification Search
CPC ...... A61P 35/02; A61P 35/04; C07B 2200/13; C07D 487/04
See application file for complete search history.

(56) References Cited

U.S. PATENT DOCUMENTS

| | | | |
|---|---|---|---|
| 7,393,848 B2 | 7/2008 | Currie et al. | |
| 7,514,444 B2 | 4/2009 | Honigberg et al. | |
| 7,718,662 B1 | 5/2010 | Chen et al. | |
| 8,084,620 B2 | 12/2011 | Liu et al. | |
| 8,735,553 B1 | 5/2014 | Li et al. | |
| 9,447,106 B2 | 9/2016 | Wang et al. | |
| 9,556,188 B2 | 1/2017 | Wang et al. | |
| 10,005,782 B2 | 6/2018 | Wang et al. | |
| 10,570,139 B2 | 2/2020 | Wang et al. | |
| 10,709,699 B2 | 7/2020 | Ding et al. | |
| 10,786,507 B2 | 9/2020 | Lu et al. | |
| 10,927,117 B2 | 2/2021 | Wang et al. | |
| 11,142,528 B2 | 10/2021 | Wang et al. | |
| 11,512,132 B2 | 11/2022 | Li et al. | |
| 11,591,340 B2 | 2/2023 | Wang et al. | |
| 11,597,768 B2 | 3/2023 | Wang et al. | |
| 11,673,951 B2 | 6/2023 | Li et al. | |
| 2002/0094989 A1 | 7/2002 | Hale et al. | |
| 2006/0178367 A1 | 8/2006 | Currie et al. | |
| 2006/0183746 A1 | 8/2006 | Currie et al. | |
| 2008/0076921 A1 | 3/2008 | Honigberg et al. | |
| 2008/0139582 A1 | 6/2008 | Honigberg et al. | |
| 2009/0105209 A1 | 4/2009 | Dewdney et al. | |
| 2009/0318441 A1 | 12/2009 | Brain et al. | |
| 2010/0004231 A1 | 1/2010 | Dewdney et al. | |
| 2010/0016296 A1 | 1/2010 | Singh et al. | |
| 2010/0016301 A1 | 1/2010 | Dewdney et al. | |
| 2010/0029610 A1 | 2/2010 | Singh et al. | |
| 2010/0035841 A1 | 2/2010 | Jankowski et al. | |
| 2010/0087464 A1 | 4/2010 | Mi et al. | |
| 2010/0105676 A1 | 4/2010 | Liu et al. | |
| 2010/0144705 A1 | 6/2010 | Miller | |
| 2010/0160292 A1 | 6/2010 | Whitney et al. | |
| 2010/0160303 A1 | 6/2010 | Liu et al. | |
| 2010/0222325 A1 | 9/2010 | Berthel et al. | |
| 2010/0249092 A1 | 9/2010 | Singh et al. | |
| 2010/0254905 A1 | 10/2010 | Honigberg et al. | |
| 2011/0118233 A1 | 5/2011 | Blomgren et al. | |
| 2011/0124640 A1 | 5/2011 | Liu et al. | |
| 2011/0224235 A1 | 9/2011 | Honigberg et al. | |
| 2011/0301145 A1 | 12/2011 | Barbosa, Jr. et al. | |
| 2012/0028981 A1 | 2/2012 | Miller | |
| 2012/0040961 A1 | 2/2012 | Gray et al. | |
| 2012/0053189 A1 | 3/2012 | Loury | |
| 2012/0058996 A1 | 3/2012 | Liu et al. | |
| 2012/0077832 A1 | 3/2012 | Witowski et al. | |
| 2012/0082702 A1 | 4/2012 | DeLucca et al. | |
| 2012/0129852 A1 | 5/2012 | Duan et al. | |

(Continued)

FOREIGN PATENT DOCUMENTS

| | | |
|---|---|---|
| CN | 1771231 A | 5/2006 |
| CN | 102656173 A | 9/2012 |

(Continued)

OTHER PUBLICATIONS

Balbach, S. et al., "Pharmaceutical evaluation of early development candidates: 'The 100 mg-approach'," International Journal of Pharmaceutics, (2004), 275, pp. 1-12.

Beigene Co., Ltd., "Phase I Clinical Research to Evaluate Safety, Tolerability and Pharmacokinetics/Pharmacodynamics Characteristics of BTK Inhibitor, BGB-3111, in Treating Chinese B Lymphocyte Tumor Patients," [Online], May 2016, Retrieved from the Internet: http://www.chinadrugtrials.org.cn/clinicaltrials.searchlistdetail.dhtml, Retrieved on: Mar. 21, 2022, 17 pages (with Machine Translation).

(Continued)

*Primary Examiner* — Kathrien A Hartsfield
(74) *Attorney, Agent, or Firm* — COOLEY LLP

(57) ABSTRACT

The present invention relates to a crystalline form of (S)-7-(1-acryloylpiperidin-4-yl)-2-(4-phenoxyphenyl)-4,5,6,7-tetra-hydropyrazolo[1,5-a]pyrimidine-3-carboxamide for inhibiting Btk, methods of preparation thereof and pharmaceutical compositions, and use of the crystalline form above in the treatment of a disease, or in the manufacturing of a medicament for the treatment of a disease.

8 Claims, 8 Drawing Sheets

(56) References Cited

U.S. PATENT DOCUMENTS

Figure 1:
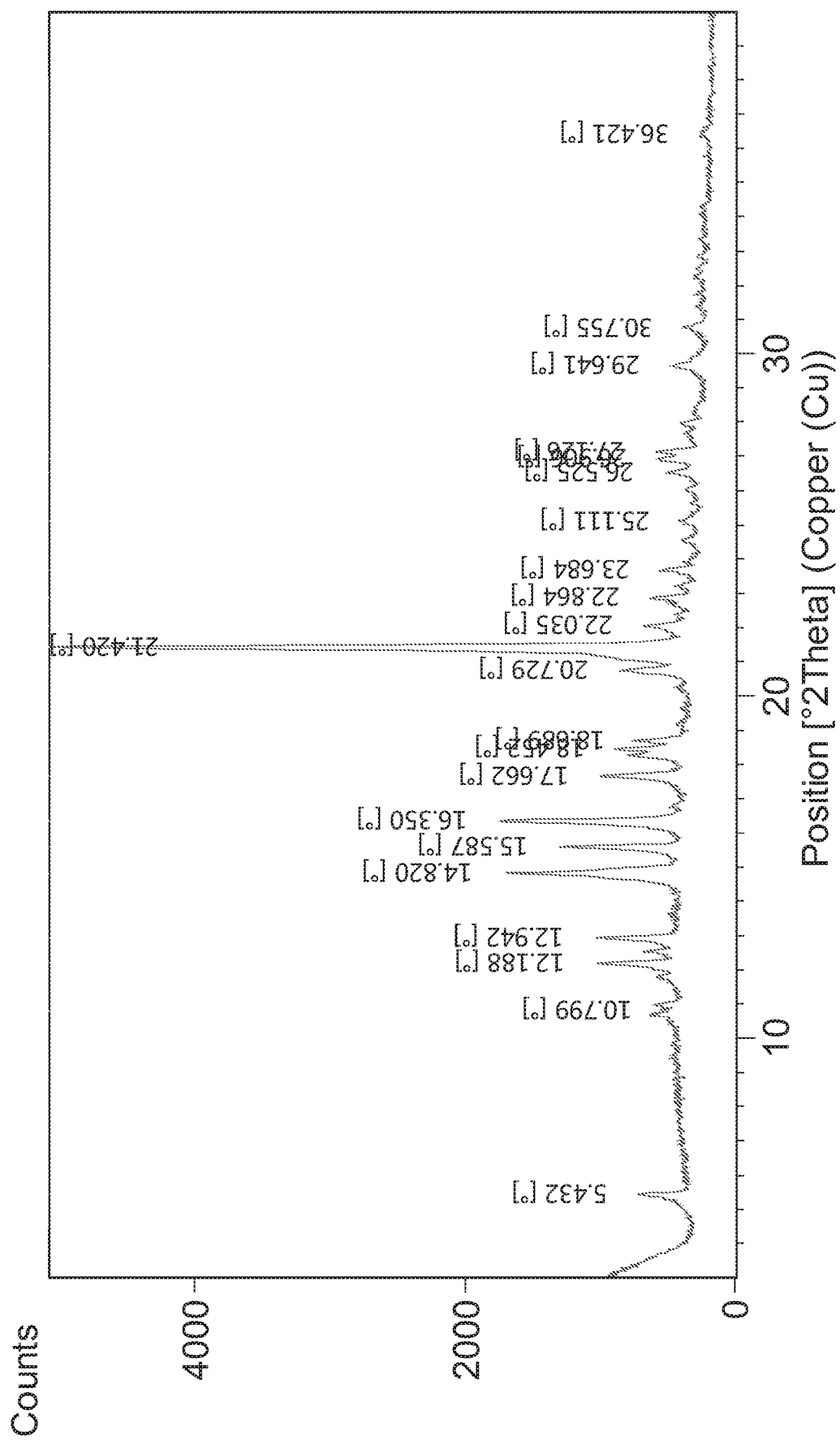

| | | |
|---|---|---|
| 2012/0157442 A1 | 6/2012 | Bui et al. |
| 2012/0157443 A1 | 6/2012 | Bui et al. |
| 2012/0232054 A1 | 9/2012 | Moriarty et al. |
| 2013/0079327 A1 | 3/2013 | Yamamoto et al. |
| 2013/0096118 A1 | 4/2013 | Liu et al. |
| 2013/0116213 A1 | 5/2013 | Cha et al. |
| 2013/0261103 A1 | 10/2013 | Currie et al. |
| 2013/0281432 A1 | 10/2013 | Currie et al. |
| 2014/0045833 A1 | 2/2014 | Laurent et al. |
| 2014/0094459 A1 | 4/2014 | Goldstein et al. |
| 2014/0107151 A1 | 4/2014 | Goldstein et al. |
| 2014/0162983 A1 | 6/2014 | Hodous et al. |
| 2014/0221398 A1 | 8/2014 | Goldstein et al. |
| 2014/0243306 A1 | 8/2014 | Heng et al. |
| 2015/0079109 A1 | 3/2015 | Li et al. |
| 2015/0118222 A1 | 4/2015 | Levy et al. |
| 2015/0259354 A1 | 9/2015 | Wang et al. |
| 2015/0315274 A1 | 11/2015 | Li et al. |
| 2016/0083392 A1 | 3/2016 | Wang et al. |
| 2017/0073349 A1 | 3/2017 | Wang et al. |
| 2018/0251466 A1 | 9/2018 | Wang et al. |
| 2019/0169201 A1 | 6/2019 | Wang et al. |
| 2020/0148690 A1 | 5/2020 | Wang et al. |
| 2020/0181150 A1 | 6/2020 | Wang et al. |
| 2020/0368237 A1 | 11/2020 | Hilger et al. |
| 2021/0130363 A1 | 5/2021 | Wang et al. |
| 2021/0275530 A1 | 9/2021 | Hu et al. |
| 2021/0332049 A1 | 10/2021 | Guo et al. |
| 2022/0241285 A1 | 8/2022 | Wang et al. |
| 2022/0249491 A1 | 8/2022 | Qiu et al. |
| 2022/0274994 A1 | 9/2022 | Wang et al. |
| 2022/0281876 A1 | 9/2022 | Wang et al. |
| 2022/0281881 A1 | 9/2022 | Wang et al. |
| 2022/0298163 A1 | 9/2022 | Wang et al. |
| 2022/0340583 A1 | 10/2022 | Wang et al. |
| 2023/0089557 A1 | 3/2023 | Yu et al. |
| 2023/0149411 A1 | 5/2023 | Wang et al. |

FOREIGN PATENT DOCUMENTS

| | | |
|---|---|---|
| CN | 104884458 A | 9/2015 |
| CN | 107530348 A | 1/2018 |
| CN | 108778281 B | 9/2021 |
| GB | 1412017 A | 10/1975 |
| JP | H07278148 A | 10/1995 |
| JP | 2006510582 A | 3/2006 |
| JP | 2010504324 A | 2/2010 |
| WO | WO-0116138 A1 | 3/2001 |
| WO | WO-0119829 A2 | 3/2001 |
| WO | WO-2002020740 | 3/2002 |
| WO | WO-0250071 A1 | 6/2002 |
| WO | WO-02072576 A1 | 9/2002 |
| WO | WO-03004497 A1 | 1/2003 |
| WO | WO-2004017908 A2 | 3/2004 |
| WO | WO-2004099249 A2 | 11/2004 |
| WO | WO-2005005429 A1 | 1/2005 |
| WO | WO-2005011597 A2 | 2/2005 |
| WO | WO-2005014599 A1 | 2/2005 |
| WO | WO-2005047290 A2 | 5/2005 |
| WO | WO-2006053121 A2 | 5/2006 |
| WO | WO-2006065946 A1 | 6/2006 |
| WO | WO-2006099075 A2 | 9/2006 |
| WO | WO-2007026720 A1 | 3/2007 |
| WO | WO-2007026950 A1 | 3/2007 |
| WO | WO-2007027594 A1 | 3/2007 |
| WO | WO-2007027729 A1 | 3/2007 |
| WO | WO-2007087068 A2 | 8/2007 |
| WO | WO-2007136790 A2 | 11/2007 |
| WO | WO-2008033834 A1 | 3/2008 |
| WO | WO-2008033854 A1 | 3/2008 |
| WO | WO-2008033857 A2 | 3/2008 |
| WO | WO-2008039218 A2 | 4/2008 |
| WO | WO-2008054827 A2 | 5/2008 |
| WO | WO-2008144253 A1 | 11/2008 |
| WO | WO-2009039397 A2 | 3/2009 |
| WO | WO-2009051822 A1 | 4/2009 |
| WO | WO-2009077334 A1 | 6/2009 |
| WO | WO-2009098144 A1 | 8/2009 |
| WO | WO-2009158571 A1 | 12/2009 |
| WO | WO-2010000633 A1 | 1/2010 |
| WO | WO-2010006947 A1 | 1/2010 |
| WO | WO-2010006970 A1 | 1/2010 |
| WO | WO-2010028236 A1 | 3/2010 |
| WO | WO-2010051549 A1 | 5/2010 |
| WO | WO-2010065898 A2 | 6/2010 |
| WO | WO-2010068788 A1 | 6/2010 |
| WO | WO-2010068806 A1 | 6/2010 |
| WO | WO-2010068810 A2 | 6/2010 |
| WO | WO-2010122038 A1 | 10/2010 |
| WO | WO-2011006074 A1 | 1/2011 |
| WO | WO-2011140488 A1 | 11/2011 |
| WO | WO-2011153514 A2 | 12/2011 |
| WO | WO-2012020008 A1 | 2/2012 |
| WO | WO-2012135801 A1 | 10/2012 |
| WO | WO-2012143522 A1 | 10/2012 |
| WO | WO-2012156334 A1 | 11/2012 |
| WO | WO-2012158795 A1 | 11/2012 |
| WO | WO-2014173289 A1 | 10/2014 |
| WO | WO-2015035606 A1 | 3/2015 |
| WO | WO-2015061752 A1 | 4/2015 |
| WO | WO-2016008411 A1 | 1/2016 |
| WO | WO-2016024228 A1 | 2/2016 |
| WO | WO-2016025720 A1 | 2/2016 |
| WO | WO-2016087994 A1 | 6/2016 |
| WO | WO-2016100914 A1 | 6/2016 |
| WO | WO-2016105582 A1 | 6/2016 |
| WO | WO-2017046746 A1 | 3/2017 |
| WO | WO-2017059224 A2 | 4/2017 |
| WO | WO-2017218844 A2 | 12/2017 |
| WO | WO-2018033135 A1 | 2/2018 |
| WO | WO-2018033853 A2 | 2/2018 |
| WO | WO-2018137681 A1 | 8/2018 |
| WO | WO-2018193105 A1 | 10/2018 |
| WO | WO-2019034009 A1 | 2/2019 |
| WO | WO-2019108795 A1 | 6/2019 |
| WO | WO-2019183226 A1 | 9/2019 |
| WO | WO-2020249001 A1 | 12/2020 |
| WO | WO-2020249002 A1 | 12/2020 |
| WO | WO-2021047623 A1 | 3/2021 |
| WO | WO-2021170045 A1 | 9/2021 |

OTHER PUBLICATIONS

Beigene, "Efficacy and Safety of Zanubrutinib in Relapsed or Refractory Chronic Lymphocytic Leukemia/Small Lymphocytic Lymphoma," [Online], Jul. 2017, Retrieved from the Internet: https://clinicaltrials.gov/ct2/show/NCT03206918, Retrieved on: Apr. 4, 2022, 7 pages.

Bradshaw, J. M., "The Src, Syk, and Tec family kinases: distinct types of molecular switches," Cell Signal., Aug. 2010, 22(8)1175-1184.

Caira, M. R. et al., "Crystalline polymorphism of organic compounds," Topics in Current Chemistry, Jan. 1, 1998, vol. 19, pp. 163-208.

Cartigny, D. et al., "General Asymmetric Hydrogenation of 2-Alkyl- and 2-Aryl-Substituted Quinoxaline Derivatives Catalyzed by Iridium-Difluorphos: Unusual Halide Effect and Synthetic Application," J. Org. Chem., Apr. 2012, vol. 77, No. 10, pp. 4544-4556.

Conley, M. E. et al., "Primary B Cell Immunodeficiencies: Comparisons and Contrasts," Annu. Rev. Immunol., 27:199-227 (2009).

Davis, R. E. et al., "Chronic active B-cell-receptor signaling in diffuse large B-cell lymphoma," Nature 463:88-92 (2010).

Extended European Search Report for European Application No. 14787642.9, dated Jan. 26, 2016, 5 pages.

Extended European Search Report for European Application No. 17841107.0, dated Feb. 21, 2020, 12 pages.

Extended European Search Report for European Application No. 17841172.4, dated Mar. 5, 2020, 6 pages.

Extended European Search Report for European Application No. 18744173.8, dated Oct. 21, 2020, 12 pages.

Gurcan, H. M. et al., "A review of the current use of rituximab in autoimmune diseases," Int. Immunopharmacol., Jan. 2009, 9(1):10-25.

(56) References Cited

OTHER PUBLICATIONS

Hackam, D. G. et al., "Translation of research evidence from animals to humans," JAMA, 296(14):1731-1732 (2006).
Hirayama, Y., "Handbook for organic compound crystal—Principle and know-how," 2008, 28 pages.
Humphries, L. A. et al., "Tec kinases mediate sustained calcium influx via site-specific tyrosine phosphorylation of the phospholipase Cgamma Src homology 2-Src homology 3 linker," J. Biol. Chem., Sep. 2004, 279(36):37651-37661.
International Search Report and Written Opinion for International Application No. PCT/CN2014/075943, dated Jul. 18, 2014, 10 pages.
International Search Report and Written Opinion for International Application No. PCT/CN2017/098023, dated Nov. 16, 2017, 10 pages.
International Search Report and Written Opinion for International Application No. PCT/CN2018/074108, dated Apr. 23, 2018, 12 pages.
International Search Report and Written Opinion for International Application No. PCT/CN2018/100145, dated Nov. 14, 2018, 8 pages.
International Search Report and Written Opinion for International Application No. PCT/CN2020/095352, dated Sep. 16, 2020, 23 pages.
International Search Report and Written Opinion for International Application No. PCT/CN2020/095353, dated Sep. 15, 2020, 23 pages.
International Search Report and Written Opinion for International Application No. PCT/IB2017/054955, dated Sep. 10, 2018, 16 pages.
International Search Report and Written Opinion for International Application No. PCT/US2018/063068, dated Feb. 27, 2019, 7 pages.
Jenkins, S. M. et al., "Substituent variation in azabicyclic triazole- and tetrazole-based muscarinic receptor ligands," J. Med. Chem., 35(13):2392-2406 (1992).
Jie, L., "Deuterated Drugs Progress," Chemical Engineering Design Communication Medicine and Chemical Industry, 2016, vol. 42, No. 4, p. 199.
Jordan, V. C., "Tamoxifen: A most unlikely pioneering medicine," Nature Reviews: Drug Discovery, 2:205-213 (2003).
Kersseboom, R. et al., "Constitutive activation of Bruton's tyrosine kinase induces the formation of autoreactive IgM plasma cells," Eur. J. Immunol. 40:2643-2654, 2010.
Khan, W. N., "Regulation of B lymphocyte development and activation by Bruton's tyrosine kinase," Immunol. Res., 23(2/3):147-156 (2001).
Kim, K.-H. et al., "Imidazo[1,5-a]quinoxalines as irreversible BTK inhibitors for the treatment of rheumatoid arthritis," Bioorg. Med. Chem. Lett., 21:6258-6263 (2011).
Kourtzelis, I., et al., "The Dual Role of Complement in Cancer and its Implication in Anti-Tumor Therapy," Annals of Translational Medicine, 2016, vol. 4(14), 14 pages.
Li, N. et al., "BGB-3111 is a novel and highly selective Bruton's tyrosine kinase (BTK) inhibitor," Cancer Center, vol. 75, No. 15, Supp. 1, Abstract No. 2597, 106th Annual Meeting of the American Association for Cancer Research, AACR 2015, Philadelphia, PA, United States, Aug. 2015, 2 pages.
Lou, Y. et al., "Bruton's tyrosine kinase inhibitors: Approaches to potent and selective inhibition, preclinical and clinical evaluation for inflammatory diseases and B cell malignancies," J. Med. Chem., 55(10):4539-4550 (2012).
Luo, J. et al., "Modern Physical Pharmaceutics Theory and Practice," Shang Hai Science and Technology Literature Publishing House, Apr. 2005, pp. 293-295.
MedChemExpress, "Zanubrutinib," Product Data Sheet, Retrieved from the Internet: www.medchemexpress.com, Retrieved Aug. 17, 2021, 2 pages.

Mohamed, A. J. et al., "Bruton's tyrosine kinase (Btk): function, regulation, and transformation with special emphasis on the PH domain," Immunol. Rev., 228:58-73 (2009).
Office Action for Japanese Application No. 2019-508889, dated Jun. 22, 2021, 7 pages.
Pan, Z, "Bruton's tyrosine kinase as a drug discovery target," Drug News Perspect, 21(7):357-362 (2008).
Pan, Z. et al., "Discovery of Selective Irreversible Inhibitors for Bruton's Tyrosine Kinase," ChemMedChem 2007, vol. 2, pp. 58-61.
Rokosz, L. L. et al., "Kinase inhibitors as drugs for chronic inflammatory and immunological diseases: progress and challenges," Expert Opin. Ther. Targets, 12(7):883-903 (2008).
Shioji, Y., "Production Technology of Solid Preparations," Tokyo, CMC Publication, Jan. 27, 2003, Popular Edition, pp. 9 and 12-13.
Singhal, D. et al., "Drug polymorphism and dosage form design: a practical perspective," Advanced Drug Delivery Reviews, 56 (2004) pp. 335-347.
Smith, C. I. et al., "Expression of Bruton's agammaglobulinemia tyrosine kinase gene, BTK, is selectively down-regulated in T lymphocytes and plasma cells," J. Immunol., Jan. 1994, 152(2):557-565.
Takada, N., "Bulk Drug Form Screening and Selection at Drug Discovery Phase," Pharm Stage, Jan. 2007, vol. 6, No. 10, pp. 20-25.
Takayama, T. et al., "Effects of the novel and potent lymphocyte-specific protein tyrosine kinase inhibitor TKM0150 on mixed lymphocyte reaction and contact hypersensitivity in mice," Arzneimittelforschung, 60(5):282-285 (2010).
Takayama, T. et al., "Ring-fused pyrazole derivatives as potent inhibitors of lymphocyte-specific kinase (Lck): Structure, synthesis, and SAR," Bioorganic & Medicinal Chemistry Letters, 20(1):112-116 (Jan. 2010).
Tam, C. S. et al., "A head-to-head Phase III study comparing zanubrutinib versus ibrutinib in patients with Waldenström macroglobulinemia," Future Oncology, vol. 14, No. 22, Sep. 2018, pp. 2229-2237.
Uckun, F. M. et al., "Bruton's tyrosine kinase as a new therapeutic target," Anti-Cancer Agents in Medicinal Chemistry, 7(6):624-632 (2007).
Vetrie, D. et al., "The gene involved in X-linked agammaglobulinaemia is a member of the src family of protein-tyrosine kinases," Nature, 361:226-233 (1993).
Wenzel, S-S et al., "MCL1 is deregulated in subgroups of diffuse large B-cell lymphoma," Leukemia, vol. 27, pp. 1381-1390 (2013).
Wilson, W. H. et al., "686—The Bruton's Tyrosine Kinase (Btk) Inhibitor, Ibrutinib (PCI-32765), Has Preferential Activity in the ABC Subtype of Relapsed/Refractory De Novo Diffuse Large B-Cell Lymphoma (DLBCL): Interim Results of a Multicenter, Open-Label, Phase2 Study," Poster #686, 54th American Society of Hematology (ASH) Annual Meeting Abstract (Dec. 10, 2012), 3 pages.
Brinckerhoff, Courtenay C., "A Fresh Look At The Lead Comound Analysis," PharmaPatents, Foley & Lardner LLP, Jan. 22, 2019, 4 pages.
Buske, C. et al., "A Head-to-Head Phase 3 Study Comparing BGB-3111 and Ibrutinib in Patients With Waldenström Macroglobulinemia," Hematological Oncology, 2017, 35: 422-423.
ClinicalTrials.gov Identifier: NCT03053440, A Study Comparing BGB-3111 and Ibrutinib in Subjects With Waldenström's Macroglobulinemia (WM) (Aug. 8, 2017), 12 pages.
ClinicalTrials.gov Identifier: NCT03145064, Study of BTK Inhibitor BGB-3111 in Subjects With Relapsed/Refractory Non-GCB Type Diffuse Large B Cell Lymphoma (May 5, 2017), 5 pages.
ClinicalTrials.gov Identifier: NCT03189524, A Study to Investigate Zanubrutinib in Chinese Participants With B-cell Lymphoma (Jun. 15, 2017), 5 pages.
ClinicalTrials.gov Identifier: NCT03206970, Study to Evaluate Efficacy and Safety of BGB-3111 in Participants With Relapsed or Refractory Mantle Cell Lymphoma (MCL) (Jul. 3, 2017). 6 pages.
Eng, Melissa C., "United States: Selecting a Lead Compound: A Balancing Act In The Chemical Obviousness Inquiry," Mondaq, Mar. 8, 2018, retrieved from the Internet on Nov. 28, 2022, 2 pages,

(56) References Cited

OTHER PUBLICATIONS

<https://www.mondaq.com/unitedstates/patent/680778/selecting-a-lead-compound-a-balancing-act-in-the-chemical-obviousness-inquiry>.

Hu, Nan, et al. "BTK inhibitor BGB-3111 demonstrates anti-tumor activity in solid tumor models." Cancer Research 77.13_Supplement (2017): 2010-2010.

"International Nonproprietary Names for Pharmaceutical Substances (INN)," WHO Drug Information, vol. 31, No. 2, 2017, pp. 241-242, 355.

Miller, Cary, "Prior Art Chemical Structures Must be More Than a 'Code Name'," Jones Day, Apr. 18, 2018, retrieved online Nov. 28, 2022, 2 pages <https://www.ptablitigationblog.com/prior-art-chemical-structures-must-be-more-than-a-code-name/>.

Noonan, Kevin E., "*Novartis Pharmaceuticals Corp. v. West-Ward Pharmaceuticals Int'l* (Fed. Cir. 2019)," Patent Docs, May 16, 2019, retreived from the internet on Nov. 28, 2022, 3 pages, <https://www.patentdocs.org/2019/05/novartis-pharmaceuticals-corp-v-west-ward-pharmaceuticals-intl-fed-cir-2019.html>.

Seymour, J. F., et al., "High Overall Response Rate With the BTK Inhibitor BGB-3111 in Patients With Chronic Lymphocytic Leukemia/Small Lymphocytic Lymphoma: An Update on Safety and Activity," Hematological Oncology, 35: 234-235.

Tam, C. et al., " The BTK Inhibitor, Bgb-3111, Is Safe, Tolerable, and Highly Active in Patients with Relapsed/ Refractory B-Cell Malignancies: Initial Report of a Phase 1 First-in-Human Trial," Blood, 2015, vol. 126 (23), 8 pages.

Tam, C. S. et al., "Phase 1 study of the selective BTK inhibitor zanubrutinib in B-cell malignancies and safety and efficacy evaluation in CLL," The American Society of Hematology, vol. 134, No. 11, pp. 851-859 (2019).

Tam, C.S. et al., "Clinical pharmacology and PK/PD translation of the second-generation Bruton's tyrosine kinase inhibitor, zanubrutinib," Expert Review of Clinical Pharmacology, 2021, vol. 14:11, pp. 1329-1344.

Tam, C.S. et al., "High Major Response Rate, Including Very Good Partial Responses (VGPR), in Patients (pts) with Waldenstrom Macroglobulinemia (WM) Treated with the Highly Specific BTK Inhibitor Bgb-3111: Expansion Phase Results from an Ongoing Phase I Study," Blood 2016; 128 (22): 1216.

Tam, C.S. et al., Twice Daily Dosing with the Highly Specific BTK Inhibitor, Bgb-3111, Achieves Complete and Continuous BTK Occupancy in Lymph Nodes, and Is Associated with Durable Responses in Patients (pts) with Chronic Lymphocytic Leukemia (CLL)/Small Lymphocytic Lymphoma (SLL). Blood 2016; 128 (22): 642. doi: https://doi.org/10.1182/blood.V128.22.642.642.

Wu, J. et al., "Second-generation inhibitors of Bruton tyrosine kinase," J Hematol Oncol. Sep. 2, 2016;9(1):80.

Atkinson, B. T., "Tec regulates platelet activation by GPVI in the absence of Btk," Blood, Nov. 15, 2003, vol. 102, Issue 19, pp. 3592-3599.

Byrd, J. C. et al., "Acalabrutinib (ACP-196) in Relapsed Chronic Lymphocytic Leukemia," N. Engl. J. Med., 2016, pp. 374:323-332.

Byrd, J. C. et al., "Targeting BTK with Ibrutinib in Relapsed Chronic Lymphocytic Leukemia," N. Engl. J. Med., 2013, vol. 369, pp. 32-42.

Byrd, J. C. et al., "Three-year follow-up of treatment-naïve and previously treated patients with CLL and SLL receiving single-agent ibrutinib," Blood, Apr. 15, 2015, vol. 125, Issue 16, pp. 2497-2506.

Chen, J. et al., "Impact of Bruton's Tyrosine Kinase Inhibitors on Collagen-Induced Platelet Aggregation: A Pharmacokinetic/Pharmacodynamic Perspective," EHA Learning Center, Meeting Abstract 2016, 4 pages.

Di Paolo et al., "Specific Btk inhibition suppresses B cell- and myeloid cell-mediated arthritis," Nat. Chem. Biol., 2011, vol. 7, pp. 41-50.

Kaur, V. et al., "Ibrutinib in CLL: a focus on adverse events, resistance, and novel approaches beyond ibrutinib," Ann. Hematol., 2017, vol. 96(7), pp. 1175-1184.

Li et al., "Skin toxicities associated with epidermal growth factor receptor inhibitors," Target Oncol.I 2009, vol. 4(2), pp. 107-119.

Melosky et al., "Supportive Care Treatments for Toxicities of Anti-EGFR and Other Targeted Agents," Curr. Oncol. 19 (Suppl 1), 2012, pp. 59-63.

Neklesa, T.K. et al., "Targeted protein degradation by PROTACs", Pharmacology & Therapeutics, 2017, vol. 174, pp. 138-144.

Raedler, L. A., "Farydak (Panobinostat): First HDAC Inhibitor Approved for Patients with Relapsed Multiple Myeloma," Am. Health Drug Benefits, Mar. 2016, vol. 9, pp. 84-87.

Wang, M. L. et al., "Targeting BTK with Ibrutinib in Relapsed or Refractory Mantle-Cell Lymphoma," N. Engl. J. Med., Aug. 8, 2013, vol. 369, pp. 507-516.

Armour, Kathryn L. et al., "Recombinant human IgG molecules lacking Fcγ receptor I binding and monocyte triggering activities," Eur. J. Immunol., Aug. 1999, vol. 29, No. 8, pp. 2613-2624.

Bowman, B.J. et al., "Hard gelatin capsules. Drug Release from HGC," Chapter 15 in Protein-Based Films and Coatings. Aristippos Gennadios (Ed.) CRC Press, 2002; p. 385.

Chan., et al., "Excipients: powders and solid dosage forms," Encyclopedia of pharmaceutical technology, 3rd ed., Informa Healthcare USA, Inc, New York 3, 2007, pp. 1646-1655.

ClinicalTrials.gov Identifier: NCT04470908, The Effect of Moderate CYP3A Inducer Rifabutin on the Pharmacokinetics of Zanubrutinab in Healthy Males, Sep. 21, 2021, 6 pages.

Extended European Search Report for European Application No. 20822606.8, dated Jun. 9, 2023, 9 pages.

He, X. "Part III. Design, Development, and Scale-Up of Formulation and Process. 18. Integration of Physical, Chemical, Mechanical, and Biopharmaceutical Properties in Solid Oral Dosage Form Development," In Developing Solid Oral Dosage Forms Pharmaceutical Theory and Practice. Elsevier Science, 2009; pp. 414-415.

Heda., et al., "8 Dry-Fill Formulation," Pharmaceutical Dosage Forms: Capsules, 2017, vol. 211, pp. 211-236.

Jiangsu Chia Tai Qingjiang Pharmaceutical Co, Ltd., Clinical Trial Reg. No. CTR20160513, Oct. 10, 2016, retrieved online at http://www.chinadrugtrials.org.cn/clinicaltrials.searchlistdetail.dhtml on May 22, 2023, 5 pages. (ENG Translation).

Ou, Y. et al., "Evaluation of drug interaction potential of zanubrutinib with cocktail probes representative of CYP34A, CYP2C9, CYP2C19, P-gp and BCRP," British Journal of Clinical Pharmacology, 2021, vol. 87, pp. 2926-2936.

Pacoud, Olivier et al., "A Woman with Relapsed Chronic Lymphocytic Leukemia and Upper Lobe Consolidation," American Thoracic Society, Nov. 2021, vol. 18, No. 11, pp. 1901-1906.

Park, B.K. et al., "The Role of Cytochrome P450 Enzymes in Hepatic and Extrahepatic Human Drug Toxicity," Pharmac. Ther., 1995, vol. 68, No. 3, pp. 385-424.

Pirmohamed, Munir et al., "The Role of Active Metabolites in Drug Toxicity," Drug Safety, 1994, vol. 11, No. 2, pp. 114-144.

Tuloup, V. et al., "Model-Based Comparative Analysis of Rifampicin and Rifabutin Drug-Drug Interaction Profile," Antimicrobial Agents and Chemotherapy, Sep. 2021, vol. 65, No. 9, e01043-21, 7 pages.

Woof, J.M., "Fc receptors and their interaction with antibodies," Biochemical Society Transactions, 1990, vol. 18, pp. 217-218.

CRYSTALLINE FORM OF (S)-7-(1-ACRYLOYLPIPERIDIN-4-YL)-2-(4-PHENOXYPHENYL)-4,5,6,7-TETRA-HYDROPYRAZOLO[1,5-A]PYRIMIDINE-3-CARBOXAMIDE, PREPARATION, AND USES THEREOF

CROSS-REFERENCE TO RELATED APPLICATIONS

This application is a continuation of U.S. application Ser. No. 17/146,855, filed on Jan. 12, 2021, which is a continuation of U.S. application Ser. No. 16/325,447, now U.S. Pat. No. 10,927,117, filed on Feb. 14, 2019, which is a U.S. National Stage Application under 35 U.S.C. § 371 of International Application No. PCT/IB2017/054955, filed on Aug. 15, 2017, which claims priority to Application No. PCT/CN2016/095510 (CN), filed Aug. 16, 2016.

FIELD OF THE INVENTION

The present invention relates to a crystalline form of (S)-7-(1-acryloylpiperidin-4-yl)-2-(4-phenoxyphenyl)-4,5,6,7-tetra-hydropyrazolo[1,5-a]pyrimidine-3-carboxamide. The present invention also relates to methods of preparing the crystalline form and methods of using the crystalline form as a Btk inhibitor.

BACKGROUND OF THE INVENTION

Bruton's tyrosine kinase (Btk) belongs to the Tec tyrosine kinase family (Vetrie et al., *Nature* 361: 226-233, 1993; Bradshaw, *Cell Signal.* 22: 1175-84, 2010). Btk is primarily expressed in most hematopoietic cells such as B cells, mast cells and macrophages (Smith et al., *J. Immunol.* 152: 557-565, 1994) and is localized in bone marrow, spleen and lymph node tissue. Btk plays important roles in B-cell receptor (BCR) and FcR signaling pathways, which involve in B-cell development, differentiation (Khan, *Immunol. Res.* 23: 147, 2001). Btk is activated by upstream Src-family kinases. Once activated, Btk in turn phosphorylates PLC gamma, leading to effects on B-cell function and survival (Humphries et al., *J. Biol. Chem.* 279: 37651, 2004).

These signaling pathways must be precisely regulated. Mutations in the gene encoding Btk cause an inherited B-cell specific immunodeficiency disease in humans, known as X-linked agammaglobulinemia (XLA) (Conley et al., *Annu. Rev. Immunol.* 27: 199-227, 2009). Aberrant BCR-mediated signaling may result in dysregulated B-cell activation leading to a number of autoimmune and inflammatory diseases. Preclinical studies show that Btk deficient mice are resistant to developing collagen-induced arthritis. Moreover, clinical studies of Rituxan, a CD20 antibody to deplete mature B-cells, reveal the key role of B-cells in a number of inflammatory diseases such as rheumatoid arthritis, systemic lupus erythematosus and multiple sclerosis (Gurcan et al., *Int. Immunopharmacol.* 9: 10-25, 2009). Therefore, Btk inhibitors can be used to treat autoimmune and/or inflammatory diseases.

In addition, aberrant activation of Btk plays an important role in pathogenesis of B-cell lymphomas indicating that inhibition of Btk is useful in the treatment of hematological malignancies (Davis et al., *Nature* 463: 88-92, 2010). Preliminary clinical trial results showed that the Btk inhibitor PCI-32765 was effective in treatment of several types of B-cell lymphoma (for example, 54th American Society of Hematology (ASH) annual meeting abstract, December 2012: 686 The Bruton's Tyrosine Kinase (Btk) Inhibitor, Ibrutinib (PCI-32765), Has Preferential Activity in the ABC Subtype of Relapsed/Refractory De Novo Diffuse Large B-Cell Lymphoma (DLBCL): Interim Results of a Multi-center, Open-Label, Phase I Study). Because Btk plays a central role as a mediator in multiple signal transduction pathways, inhibitors of Btk are of great interest as anti-inflammatory and/or anti-cancer agents (Mohamed et al., *Immunol. Rev.* 228: 58-73, 2009; Pan, *Drug News perspect* 21: 357-362, 2008; Rokosz et al., *Expert Opin. Ther. Targets* 12: 883-903, 2008; Uckun et al., *Anti-cancer Agents Med. Chem.* 7: 624-632, 2007; Lou et al, *J. Med. Chem.* 55(10): 4539-4550, 2012).

International application WO2014173289A disclosed a series of fused heterocyclic compounds as Btk inhibitors. In particular, WO2014173289A disclosed (S)-7-(1-acryloylpiperidin-4-yl)-2-(4-phenoxyphenyl)-4,5,6,7-tetra-hydropyrazolo[1,5-a]pyrimidine-3-carboxamide (hereinafter Compound 1)

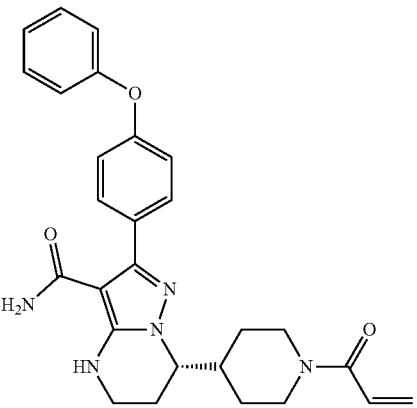

Compound 1

Compound 1 is a potent, specific and irreversible BTK kinase inhibitor. The data generated in preclinical studies using biochemical, cell based and animal studies suggested that Compound 1 could offer significant benefit in inhibiting tumor growth in B-cell malignancies. As Compound 1 was shown to be more selective than ibrutinib for inhibition of BTK vs. EGFR, FGR, FRK, HER2, HER4, ITK, JAK3, LCK, and TEC, it is expected to give rise to less side-effects than ibrutinib in clinic. In addition, Compound 1 showed significantly less inhibition of rituximab-induced antigen-dependent cell-mediated cytotoxicity (ADCC) than ibrutinib due to weaker ITK inhibition, and therefore may provide better efficacy when combined with rituximab or other ADCC-dependent antibody in treating B-cell malignancies.

Preclinical safety evaluation has demonstrated that Compound 1 was safer than ibrutinib in terms of the overall tolerance and severe toxicities in both rat and dog single and repeat dose toxicity studies up to 28 days. Additionally, Compound 1 had better bioavailability without accumulation issues observed for ibrutinib. These unique characteristics warrant further evaluation of Compound 1 in clinical studies.

Figure 7A:
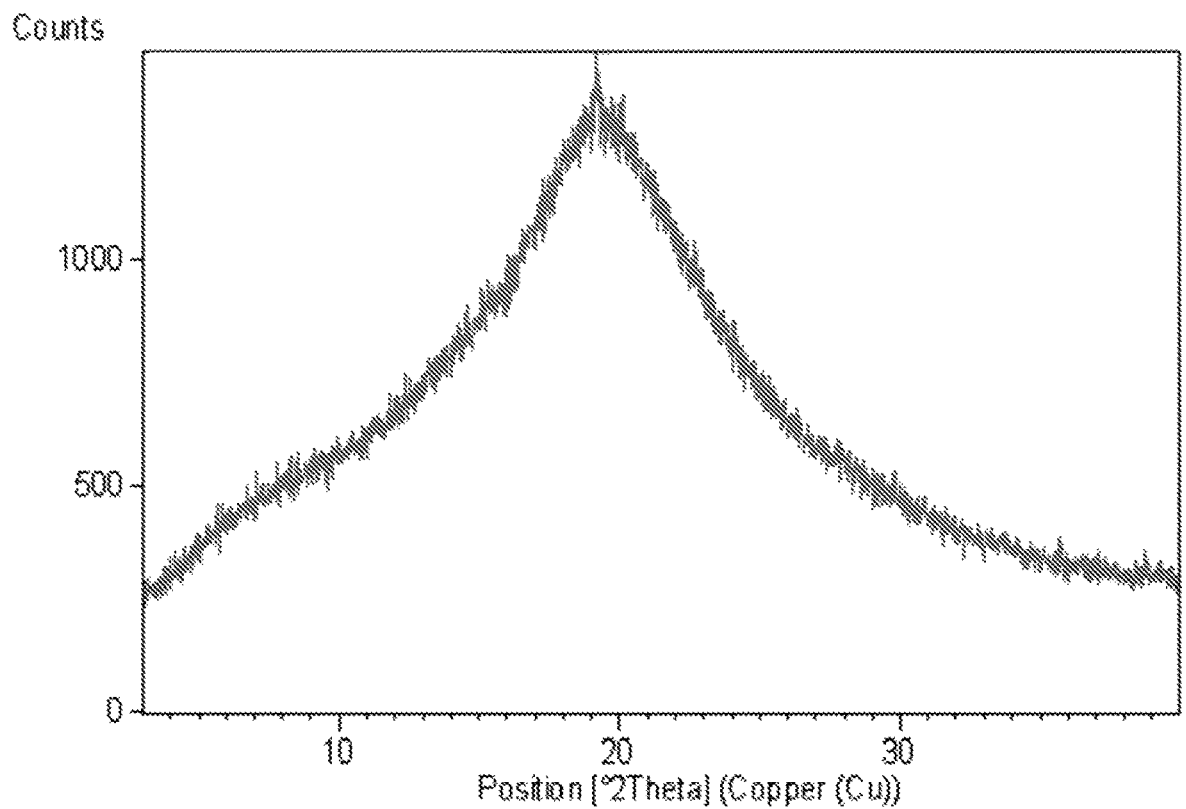
Figure 7B:
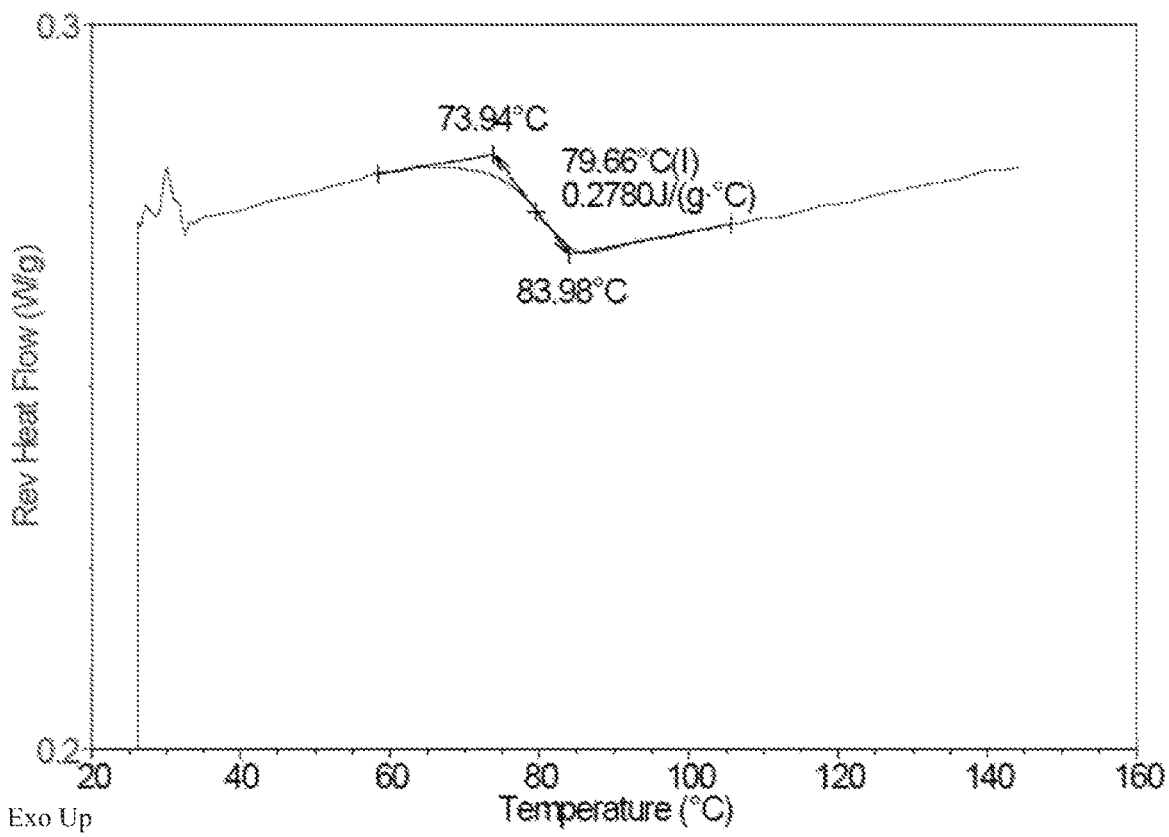

However, Compound 1 was found to be an amorphous form according to the preparation method for Compound 27 in WO 2014173289A, which was further confirmed by the X-Ray Powder Diffraction pattern of FIG. 7A. The amorphous form was shown to have a low glass transition temperature as shown in FIG. 7B, indicating some difficulties in the drug formulation with the amorphous form, such as low stability and hard to purify. Therefore, it's necessary to develop a new form of Compound 1 which possesses characteristics such as high melting point and better stability, suitable for drug formulation.

SUMMARY OF THE INVENTION

The inventors have unexpectedly found a crystalline form of Compound 1, which possesses a high melting point and shows an extremely stable profile even when stored at 25° C./60% RH for up to 24 months or stored at 40° C./75% RH condition for up to 6 months.

In a first aspect, disclosed herein is a crystalline form of Compound 1,

Compound 1

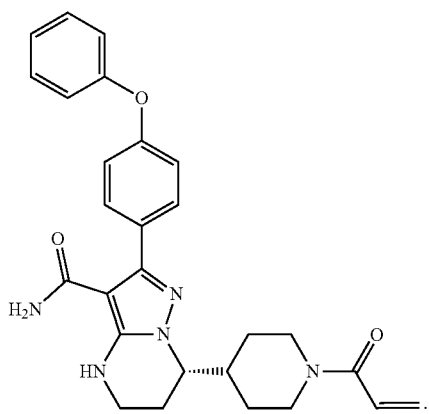

In some embodiments, the crystalline form of Compound 1 is a crystalline anhydrate (herein referred to as "Crystalline Form A").

Figure 11:
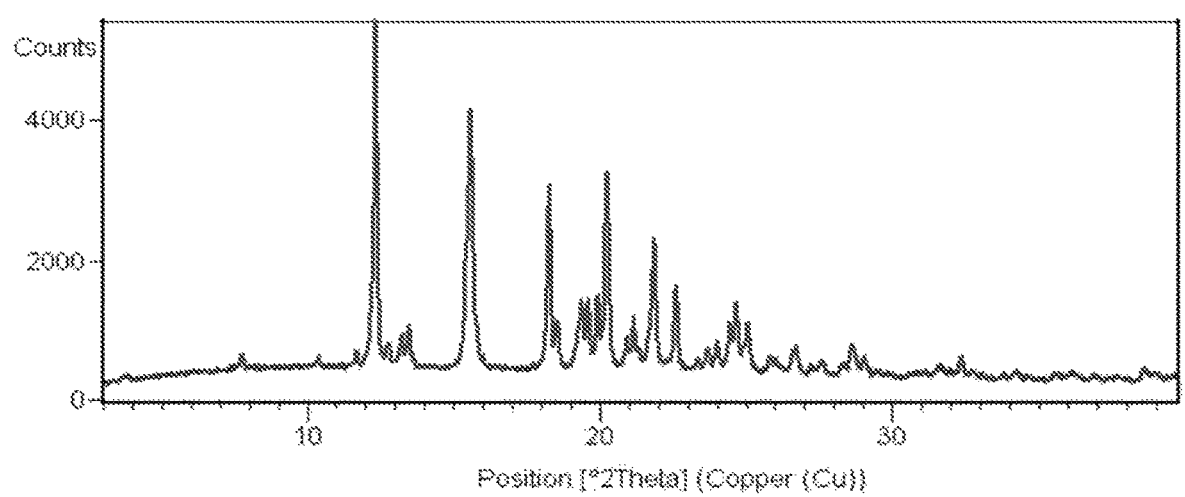

In a second aspect, disclosed herein is a crystalline form of Compound BG-13, which has an X-ray powder diffraction pattern substantially in accordance with FIG. 11.

Compound BG-13

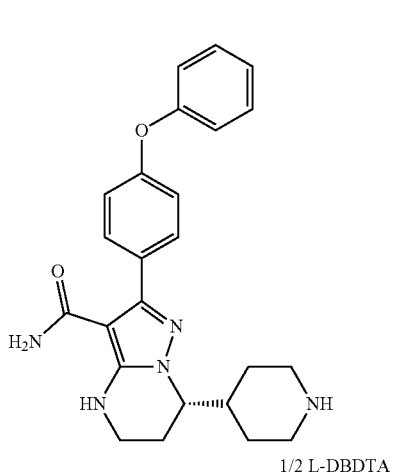

1/2 L-DBDTA

In a third aspect, disclosed herein is a method of preparing Compound 1.

Also disclosed herein is an intermediate compound of Formula Ie or a salt thereof, or Formula If or a salt thereof used to prepare Compound 1, Formula Ie

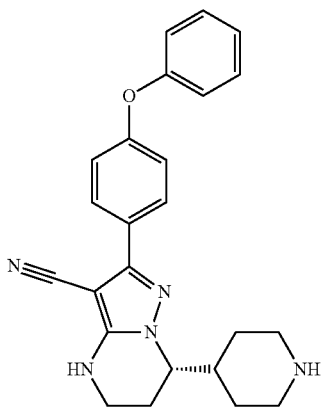

Formula If

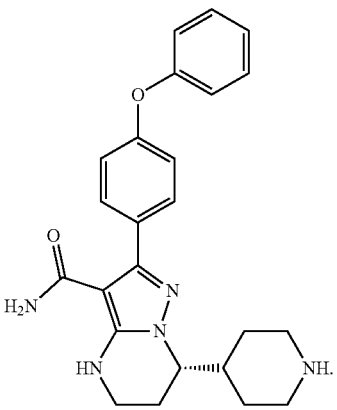

In a fourth aspect, disclosed herein is a method of preparing Crystalline Form A disclosed herein.

In a fifth aspect, disclosed herein is a pharmaceutical composition comprising a therapeutically effective amount of Crystalline Form A disclosed herein.

In a sixth aspect, disclosed herein is a method of treating a disease associated with undesirable Btk activity in a subject by administering to a subject Crystalline Form A disclosed herein.

In a seventh aspect, disclosed herein is a method of treating a disease selected from an allergic disease, an autoimmune disease, an inflammatory disease, a cancer, or a combination of two or more thereof, in a subject by administering to the subject Crystalline Form A disclosed herein.

In an eighth aspect, disclosed herein is a method of treating a B-cell proliferative disease, selected from B-cell malignancies, or relapsed/refractory B-cell malignancies, in a subject by administering to the subject Crystalline Form A disclosed herein. In some embodiment of this aspect, disclosed herein is a method of treating a B-cell proliferative disease, selected from chronic lymphocytic, non-Hodgkin's lymphoma, diffuse large B cell lymphoma, mantle cell lymphoma, follicular lymphoma, chronic lymphocytic leukemia, small lymphocytic lymphoma, waldenstrom macroglobulinemia, marginal zone lymphoma, Hairy cell leukemia, Burkitt's-like leukemia or a combination of two or more thereof, in a subject by administering to the subject Crystalline Form A disclosed herein.

In a ninth aspect, disclosed herein is a use of Crystalline Form A disclosed herein in manufacturing a medicament for treatment of at least one disease associated with undesirable Btk activity, in a subject.

In a tenth aspect, disclosed herein is a use of Crystalline Form A disclosed herein in manufacturing a medicament for treatment of a disease selected from an allergic disease, an autoimmune disease, an inflammatory disease, a cancer, or a combination of two or more thereof, in a subject.

In an eleventh aspect, disclosed herein is a use of Crystalline Form A disclosed herein in manufacturing a medicament for treatment of a B-cell proliferative disease selected from B-cell malignancies, or relapsed/refractory B-cell malignancies, in a subject. In some embodiment of this aspect, disclosed herein is a use of Crystalline Form A disclosed herein in manufacturing a medicament for treatment of a B-cell proliferative disease selected from chronic lymphocytic, non-Hodgkin's lymphoma, diffuse large B cell lymphoma, mantle cell lymphoma, follicular lymphoma, chronic lymphocytic leukemia, small lymphocytic lymphoma, waldenstrom macroglobulinemia, marginal zone lymphoma, Hairy cell leukemia, Burkitt's-like leukemia, or a combination of two or more thereof, in a subject.

In a twelfth aspect, disclosed herein is a process for preparing a crystalline form A of Compound 1, comprising mixing amorphous form of compound 1 with the following solvent system to form a clear solution; keeping the solution at room temperature or heat with or without stirring for a certain period of time to precipitate the crystalline form A, wherein the solvent system is:
  ethyl acetate:hexane=1:0.6-0.7 by volume ratio;
  ethyl acetate:heptane=1:0.6-0.7 by volume ratio;
  ethyl acetate:cyclohexane=1:0.6-1.2 by volume ratio;
  methyl acetate:hexane=1:0.6-1.2 by volume ratio;
  toluene:hexane=1.0:0.2-0.4 by volume ratio;
  toluene:cyclohexane=1.0:0.1-0.2 by volume ratio;
  methyl acetate:cyclohexane=0.6-0.8:1.0 by volume ratio;
  IPAC:cyclohexane=1.0:0.2-1.0 by volume ratio; or
  Isobutyl acetate:cyclohexane=1.0:0.2-1.0 by volume ratio.

In one embodiment, the amorphous form of compound 1 has an ee value more than 90%. In other embodiment, the amorphous form of compound 1 has an ee value of 97%.

BRIEF DESCRIPTIONS OF THE DRAWINGS

Figure 2:
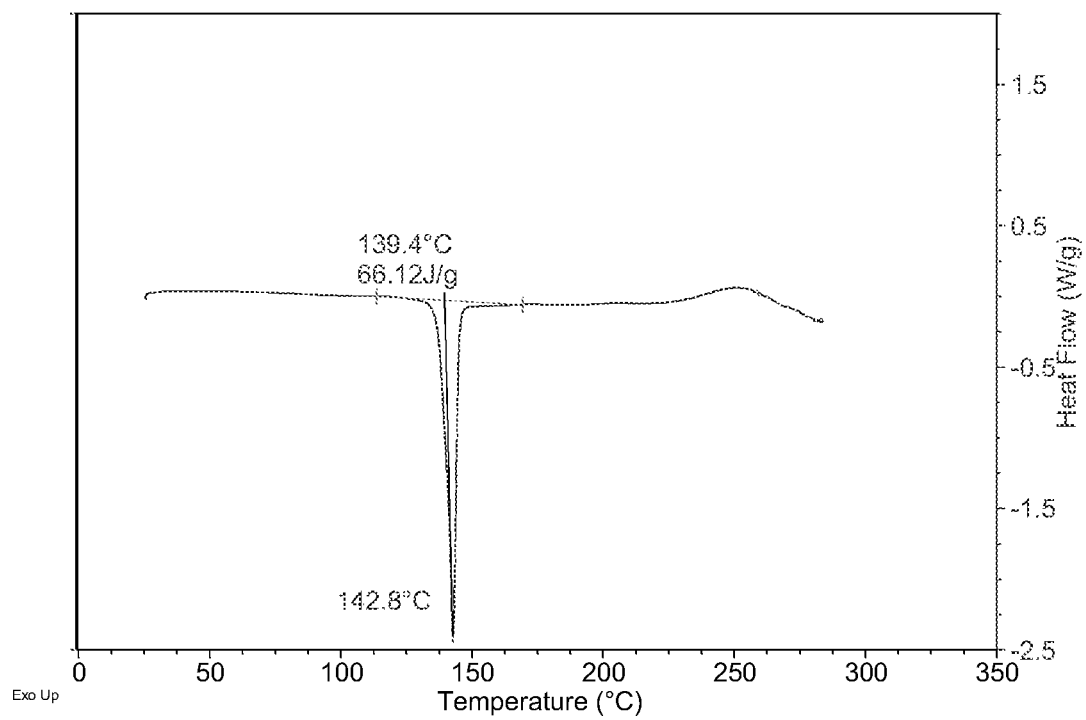
Figure 3:
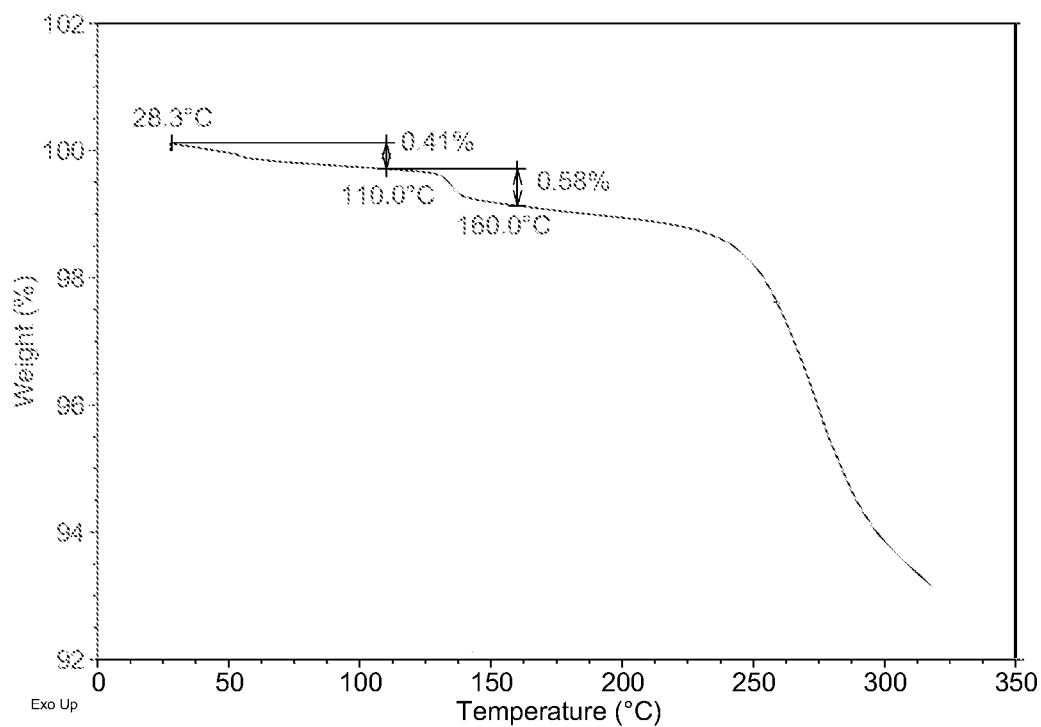
Figure 4:
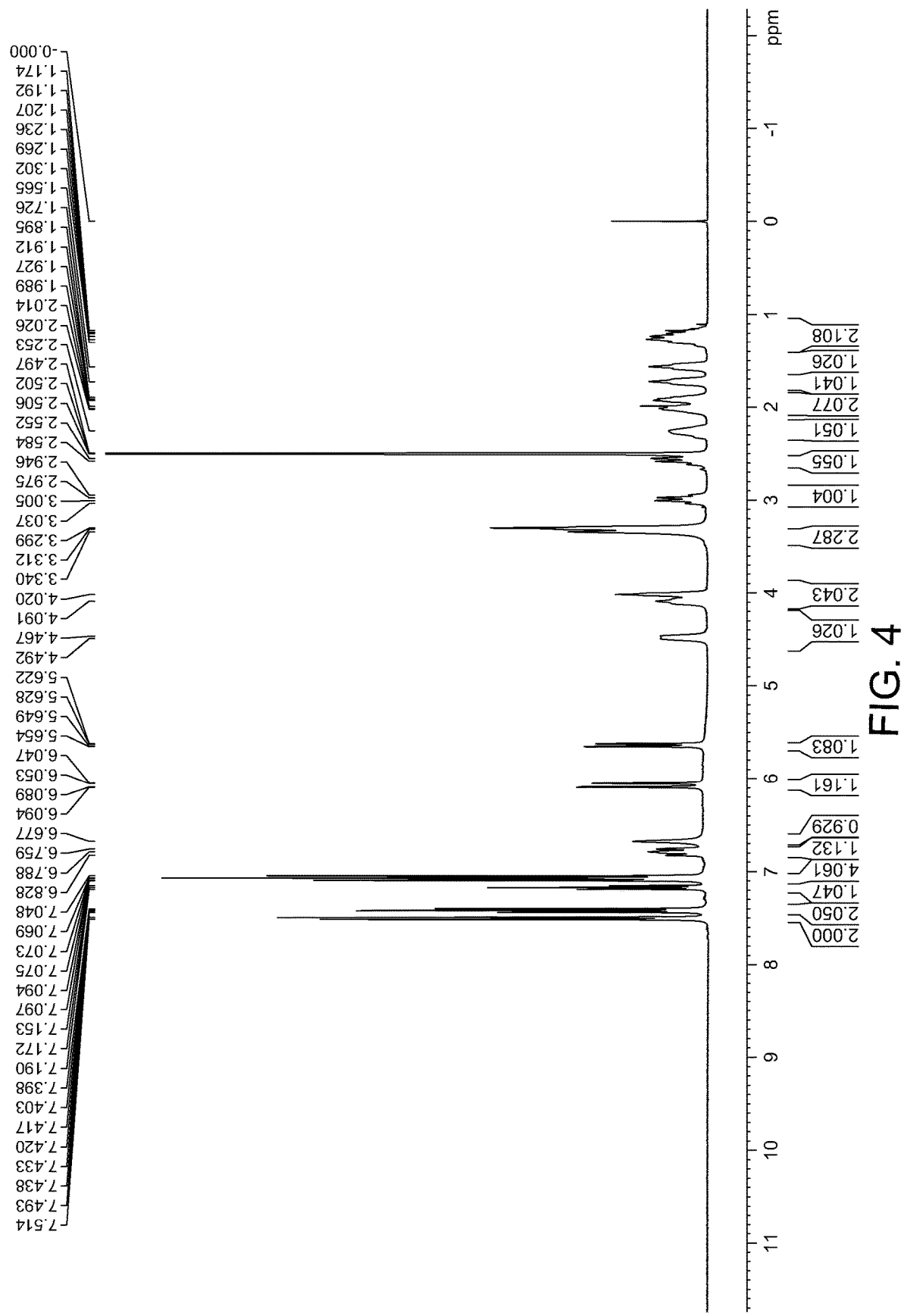
Figure 5:
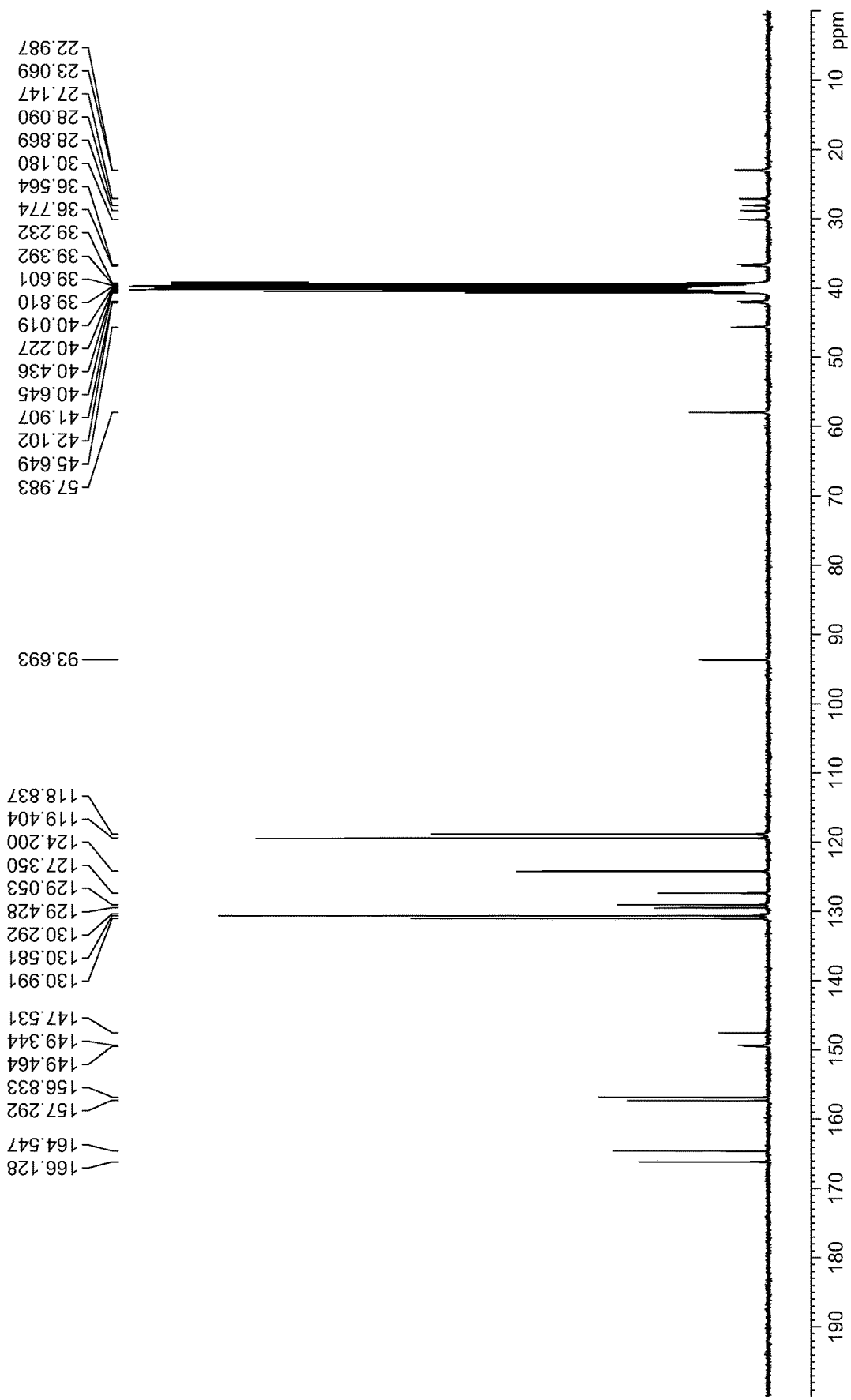
Figure 6:
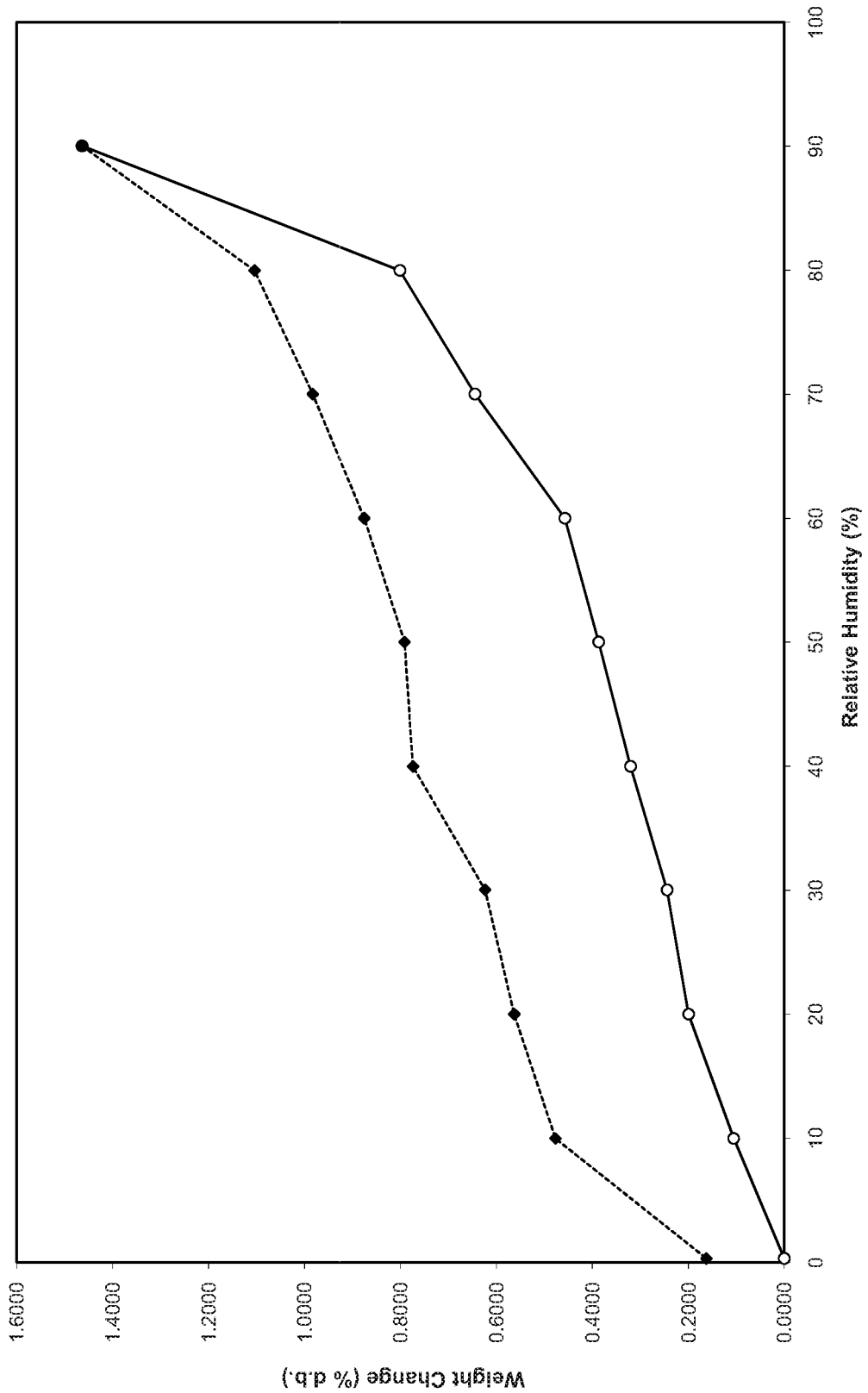
Figure 8:
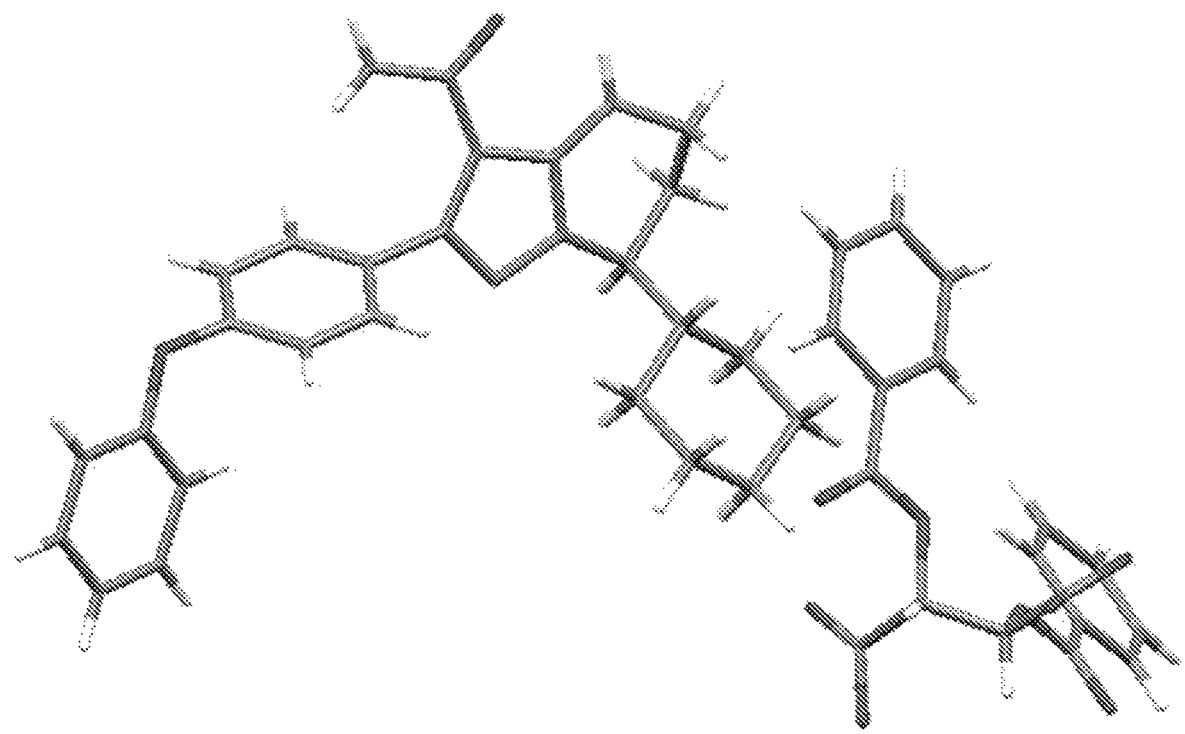
Figure 9:
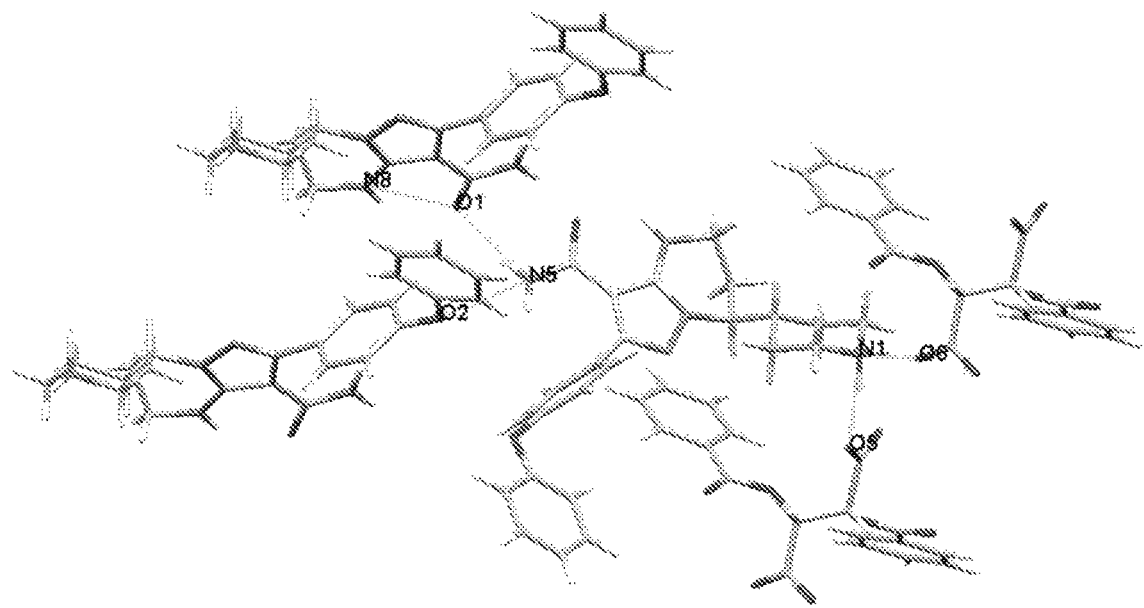
Figure 10:
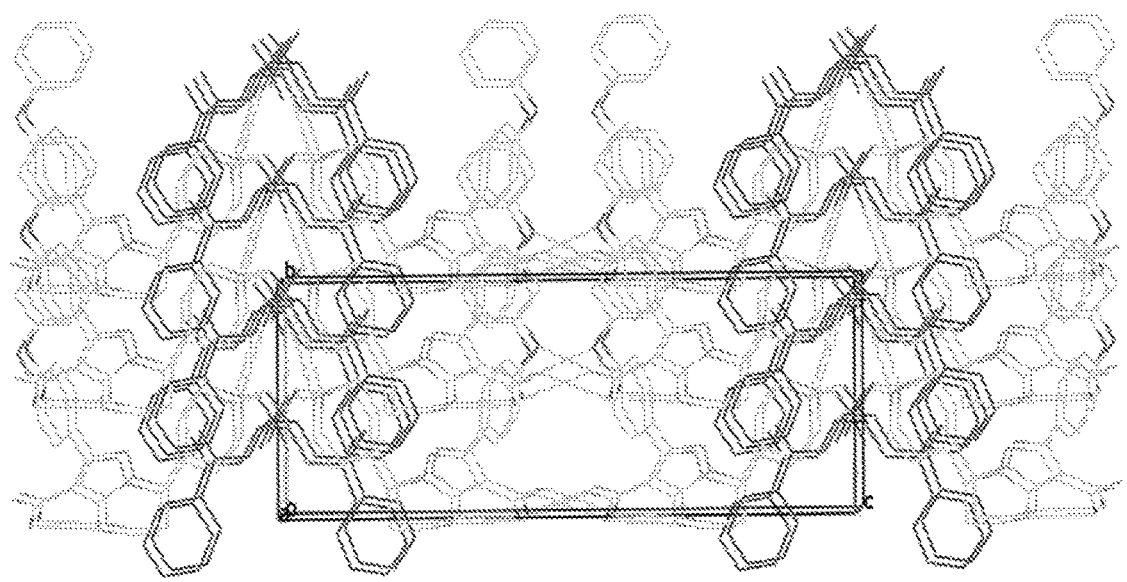

FIG. 1 shows the XRPD pattern of Crystalline Form A.
FIG. 2 shows the DSC curve of Crystalline Form A.
FIG. 3 shows the TGA curve of Crystalline Form A.
FIG. 4 shows the $^1$H-NMR of Crystalline Form A.
FIG. 5 shows the $^{13}$C-NMR of Crystalline Form A.
FIG. 6 shows DVS plot of Crystalline Form A.
FIG. 7A shows the XRPD pattern of the amorphous form of Compound 1.
FIG. 7B shows the mDSC curve of the amorphous form of Compound 1, showing the glass transition temperature of the amorphous form is 79.7° C. (mid-point temperature).
FIG. 8 shows the absolute structure of single crystal of BG-13.
FIG. 9 illustrates hydrogen bonds of single crystal of BG-13.
FIG. 10 shows a crystal packing of single crystal of BG-13.
FIG. 11 shows the XRPD pattern of single crystal of BG-13.

DETAILED DESCRIPTION OF THE INVENTION

The inventors have unexpectedly found that Compound 1 in a crystalline form, named as Crystalline Form A, can only be obtained at a particular conditions, depending on the ee value of the starting materials, and the ratio of the co-solvents and so on. A polymorph study was also performed through methods of slow evaporation, anti-solvent addition, slow cooling, vapor diffusion and polymer-induced crystallization. Most of experiments failed to get crystalline form, which indicates the obtaining of Crystalline Form A is not straight forward.

Further characterization results have revealed that Crystalline Form A is an anhydrate with a melting point of 139.4±2° C. (onset temperature). To evaluate stability, the sample of Crystalline Form A was stored at 80° C. for 2 days, 25° C./60% RH for up to 24 months or 40° C./75% RH condition for up to 6 months, and characterized by XRPD before, during and after the stability test. Results showed no crystal form change was observed for all the above periods, indicating good physical stability of Crystalline Form A at 80° C. or stored at 25° C./60% RH for up to 24 months and at 40° C./75% RH condition for up to 6 months.

In some embodiments, Crystalline Form A has an X-ray powder diffraction pattern comprising diffraction peaks having 2θ angle values independently selected from: approximately 14.8±0.2°, 16.4±0.2° and 21.4±0.2°.

In some embodiments, Crystalline Form A has an X-ray powder diffraction pattern comprising diffraction peaks having 2θ angle values independently selected from: approximately 14.8±0.2°, 15.6±0.2°, 16.4±0.2° and 21.4±0.2°.

In some embodiments, Crystalline Form A has an X-ray powder diffraction pattern comprising diffraction peaks having 2θ angle values independently selected from: approximately 12.2±0.2°, 12.9±0.2°, 14.8±0.2°, 15.6±0.2°, 16.4±0.2° and 21.4±0.2°.

In some embodiments, Crystalline Form A has an X-ray powder diffraction pattern comprising diffraction peaks having 2θ angle values independently selected from: approximately 12.2±0.2°, 12.9±0.2°, 14.8±0.2°, 15.6±0.2°, 16.4±0.2°, 17.7±0.2°, 18.5±0.2°, 20.7±0.2° and 21.4±0.2°.

In some embodiments, Crystalline Form A has an X-ray powder diffraction pattern substantially in accordance with FIG. 1.

In some embodiments, Crystalline Form A has an X-ray powder diffraction pattern summarized in Table 1.

TABLE 1

| X-ray Diffraction Pattern of Crystalline Form A | | | |
| --- | --- | --- | --- |
| Peak# | Diffraction angle (2-theta) | Spacing | Relative intensity |
| 1 | 5.432 | 16.26908 | 7.37 |
| 2 | 10.799 | 8.19295 | 2.40 |
| 3 | 12.188 | 7.26191 | 13.19 |
| 4 | 12.942 | 6.84040 | 13.51 |
| 5 | 14.820 | 5.97780 | 28.09 |
| 6 | 15.587 | 5.68534 | 19.63 |
| 7 | 16.350 | 5.42177 | 29.30 |
| 8 | 17.662 | 5.02158 | 13.62 |
| 9 | 18.452 | 4.80853 | 11.39 |
| 10 | 18.689 | 4.74791 | 8.26 |
| 11 | 20.729 | 4.28515 | 11.07 |
| 12 | 21.420 | 4.14847 | 100.00 |
| 13 | 22.035 | 4.03409 | 7.59 |
| 14 | 22.864 | 3.88958 | 6.70 |
| 15 | 23.684 | 3.75673 | 5.24 |
| 16 | 25.111 | 3.54646 | 2.43 |
| 17 | 26.525 | 3.36044 | 5.13 |

TABLE 1-continued

X-ray Diffraction Pattern of Crystalline Form A

| Peak# | Diffraction angle (2-theta) | Spacing | Relative intensity |
|---|---|---|---|
| 18 | 26.906 | 3.31381 | 6.41 |
| 19 | 27.126 | 3.28741 | 6.92 |
| 20 | 29.641 | 3.01393 | 4.61 |
| 21 | 30.755 | 2.90724 | 2.58 |
| 22 | 36.421 | 2.46692 | 1.29 |

In some preferred embodiments, Crystalline Form A has a melting point of 139±2° C. (onset temperature).

In some preferred embodiments, Crystalline Form A has a DSC substantially in accordance with FIG. 2.

In some preferred embodiments, Crystalline Form A has a TGA substantially in accordance with FIG. 3.

In some embodiments, the crystalline Form A is slightly hygroscopic. In some embodiments, the crystalline Form A is unsolvated.

In some embodiments, the crystalline Form A has substantially the same X-ray powder diffraction (XRPD) pattern post storage at 40° C. and 75% RH for up to 6 months. In some embodiments, the crystalline Form A has substantially the same X-ray powder diffraction (XRPD) pattern post storage at 25° C. and 60% RH for up to 24 months.

Also disclosed herein is a crystalline form of Compound BG-13, which has an X-ray powder diffraction pattern substantially in accordance with FIG. 11, Compound BG-13

1/2 L-DBTA

In some of embodiments, the crystalline form of BG-13 is a single crystal, which has a unit cell dimensions comprising a=16.7939(4) Å, b=7.9871(2) Å, c=23.5438(5)Å, alpha=90.00 deg., beta=108.0460(10) deg., gamma=90.00 deg.

The inventors have deduced the absolute configurations of Compound 1 to be S from the single crystal X-ray structural analysis of intermediate BG-13.

Also disclosed herein is a method for preparing Compound 1 and deuterium-labeled Compound 1, such as the procedures depicted in Scheme 1. The new synthetic methods and the crystallization/recrystallization procedures of Compound 1 via crystalline Form A disclosed herein overcome many issues associated with the processes reported previously, such as preparation of the key chiral intermediate with >98% optical purity, improve the purity of Compound 1 to reach the acceptance criteria in the specification, control the impurities in Compound 1 and provide many advantages over the existing processes. Notably, the methods disclosed herein are especially suitable for reproducible, commercial-scale manufacture of Compound 1 in high quality and good yields. In an alternative process, BG-9 or its analogs in Scheme 1 could be asymmetrically reduced with low to excellent enantioselectivities (5% ee. to 95% ee). The process of other steps are similar to those listed in Scheme 1.

Scheme 1: Preparation of Compound 1 and deuterium-labeled Compound 1

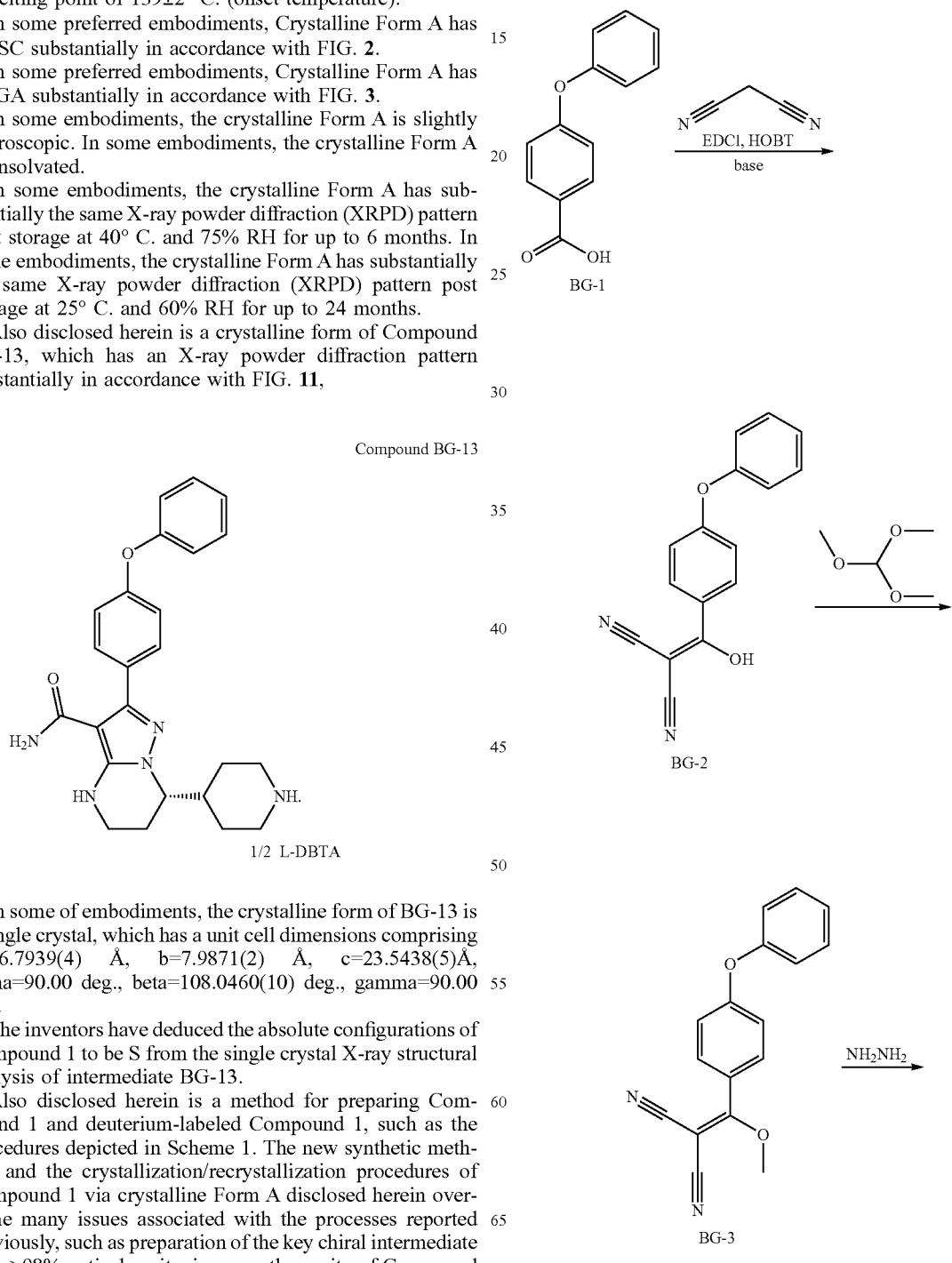

-continued
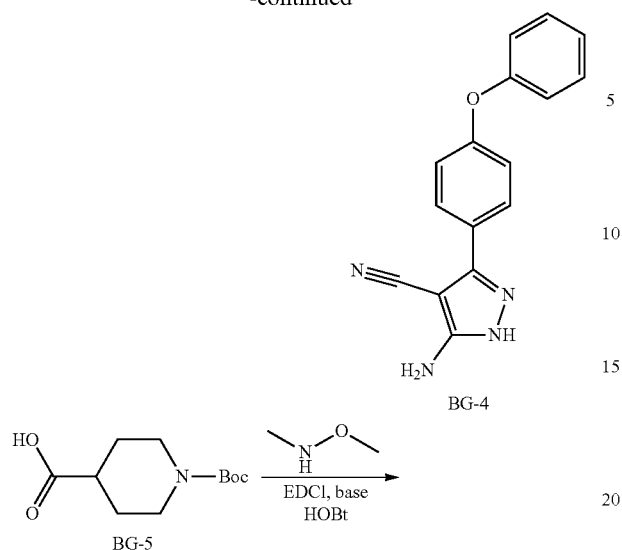
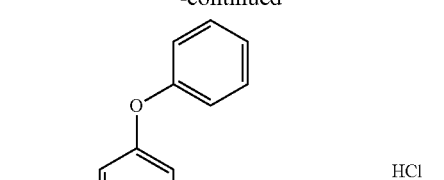
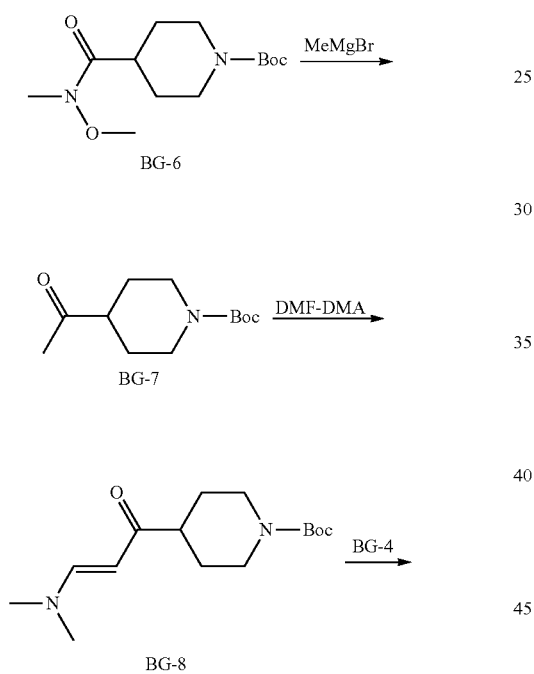
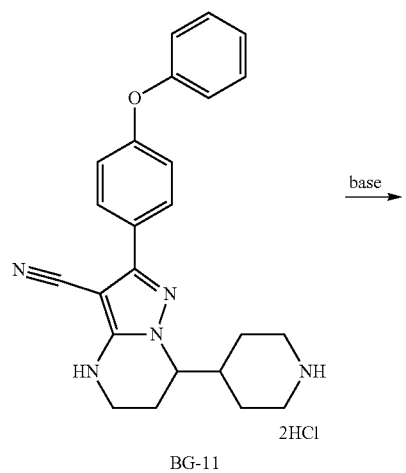
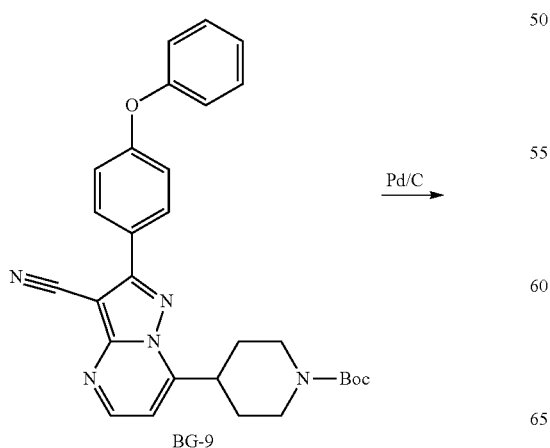
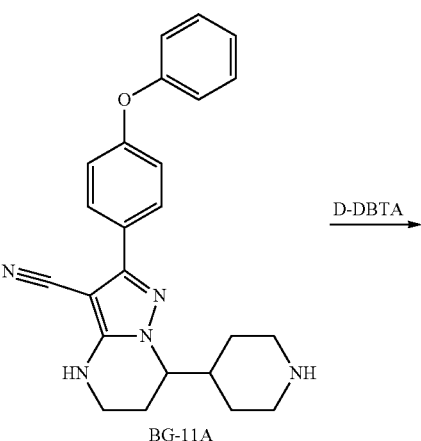

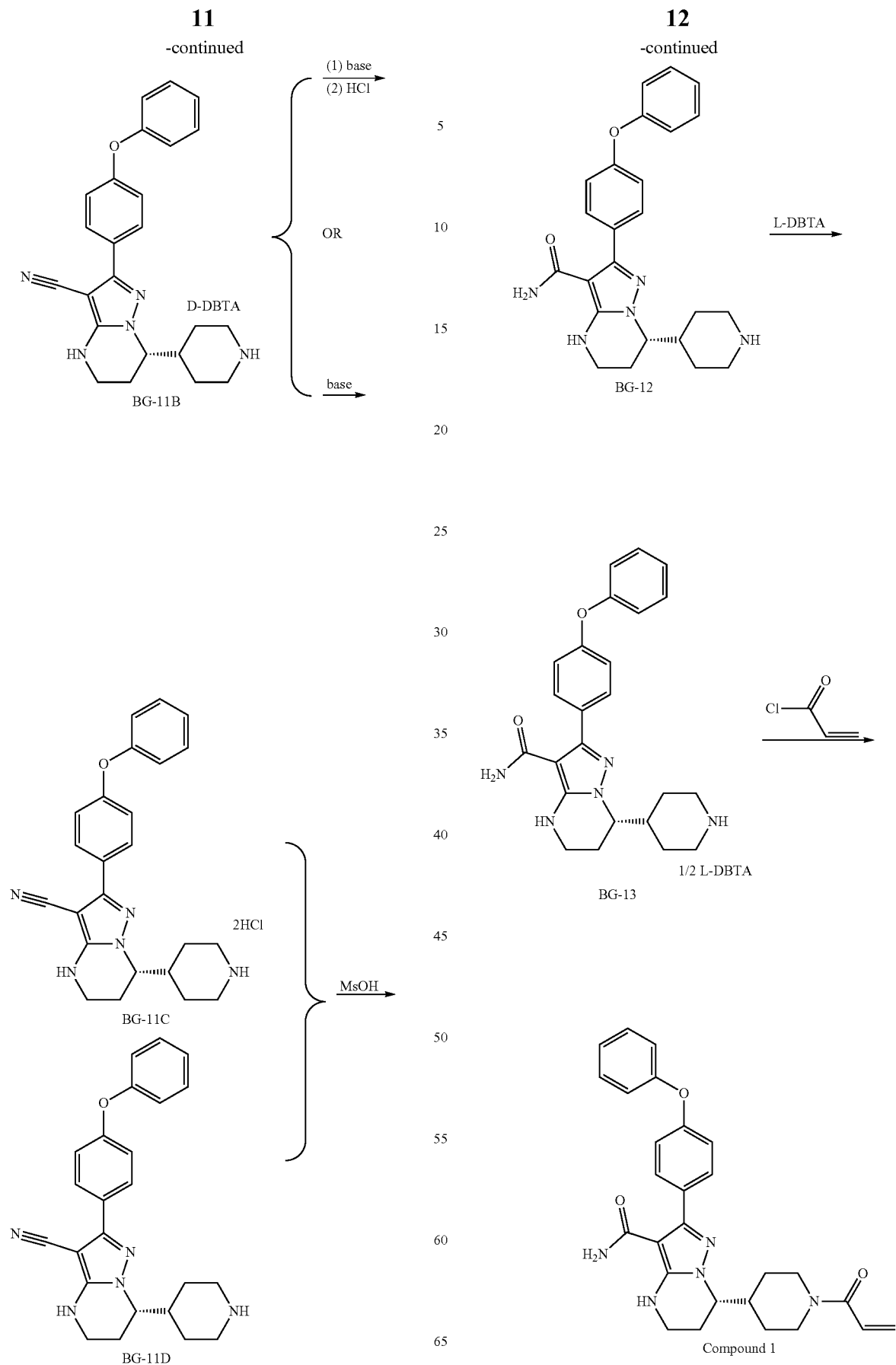

13
-continued

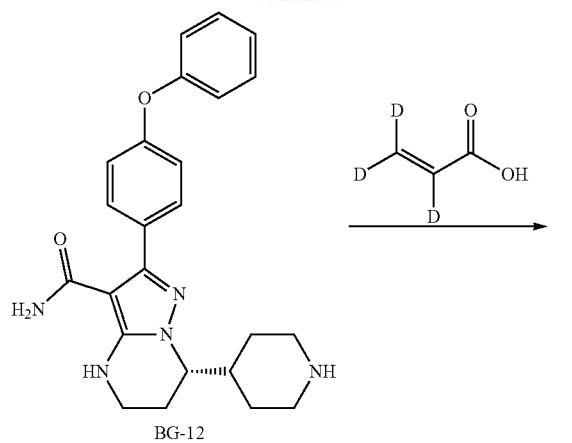
BG-12

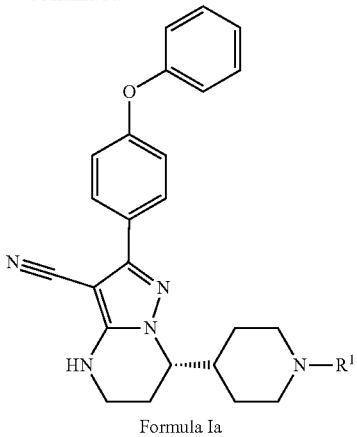
Formula Ia wherein R¹ is hydrogen or an amino protecting group.

In some embodiments, the amino protecting group includes, but not limit to, acetyl, propionyl, butyryl, phenylacetyl, benzoyl, toluyl, Phenoxyacetyl (POA), methoxycarbonyl, ethoxy carbonyl, 2,2,2-trichloroethoxycarbonyl, tert-butyloxycarbonyl (BOC), 2-iodoethoxycarbonyl, carbobenzoxy (CBZ), 4-methoxybenzyloxycarbonyl, (Fluoren-9-ylmethoxy)carbonyl (Fmoc), 4-methoxy-2,3,6-trimethylbenzenesulphonyl (Mtr), benzyl, methyl or 4-methoxybenzyl.

In some embodiments, wherein the catalyst is a neutral catalyst system or a cationic catalyst system. In some preferred embodiments, the catalyst is a iridium catalyst system including, but not limited to, [Ir(COD)Cl]$_2$/(R or S)-MeO-Biphep, [Ir(COD)Cl]$_2$/(R or S)-Binap, [Ir(COD)Cl]$_2$/(R or S)-Tol-Binap, [Ir(COD)Cl]$_2$/(R or S)-xyl-Binap, [Ir(COD)Cl]$_2$/(S,S or R,R)-Diop, [Ir(COD)Cl]$_2$/(R or S)-P-Phos, [Ir(COD)Cl]$_2$/(R or S)-Tol-P-Phos, [Ir(COD)Cl]$_2$/(R or S)-Xyl-P-Phos, [Ir(COD)Cl]$_2$/(R,R or S,S)-Me-DuPhos, [Ir(COD)Cl]$_2$/(R or S)-SegPhos, [Ir(μ-Cl)(cod)]$_2$/(R or S)-Ship, [Ir(μ-Cl)(cod)]$_2$/(R or S)-Siphos, [Ir(μ-Cl)(cod)]$_2$/(R or S)-Siphos-PE, [Ir(μ-Cl)(cod)]$_2$/(R or S)-MonoPhos, [Ir(μ-Cl)(cod)]$_2$/(R or S)-tol-SDP, [Ir(μ-Cl)(cod)]$_2$/(S,S or R,R)-Diop, [Ir(μ-Cl)(cod)]$_2$/(S,R or R,S)-Josiphos, [Ir(μ-Cl)(cod)]$_2$/(R or S)-Binap, [Ir(μ-Cl)(cod)]$_2$/(R or S)-MeO-Biphep, [Ir(μ-Cl)(cod)]$_2$/(R or S)-Synphos, or [Ir(μ-Cl)(cod)]$_2$/(R or S)-Difluorphosor [Ir(cod)$_2$]$^+$X$^-$ (X: e.g. BF$_4$, NO$_3$, OTf, PF$_6$, SbF$_6$ and BarF) plus related ligands as described above (Wen-Bo et al., *J. AM. CHEM. SOC.* 125, 10536-10537 2003. Damien et al., *J. Org. Chem.* 77, 4544-4556, 2012. Milos et al., *Org. Process Res. Dev.* 16, 1293-1300, 2012.); a rhodium catalyst system including, but not limited to, [Rh(COD)$_2$]BF$_4$ plus ligands described above (Xiang-Ping et al., *Top Organomet Chem* 36, 313-354, 2011); or, a ruthenium catalyst system including, but not limited to, RuCl$_2$(R or S)-BINAP/(R or S)-DAIPEN, RuCl$_2$(R or S)-BINAP/(R,R or S,S)-DPEN, RuCl$_2$(S or R)-BINAP (S,S or R,R)-DACH, RuCl$_2$[(R or S)-Tol-BINAP][(S,S or R,R)-DPEN], RuCl$_2$(R,R or S,S)-Me-DuPHOS/(R,R or S,S)-DPEN, RuCl$_2$(R,R or S,S)-Et-DuPHOS/(R,R or S,S)-DPEN, RuCl$_2$(R,R or S,S)-Et-DuPHOS/(R,R or S,S)-DACH, RuCl$_2$(S,S or R,R)-i-Pr-DuPHOS/(R,R or S,S)-DPEN, RuCl$_2$(R or S)-HexaPHEMP/(R,R or S,S)-DPEN, RuCl$_2$(R or S)-MeO-BIPHEP/(R,R or S,S)-DPEN (Christopher et al., *Adv. Synth. Catal.* 345, 195-201, 2003. Julian et al., *Adv. Synth. Catal.* 345, 300-307, 2003.).

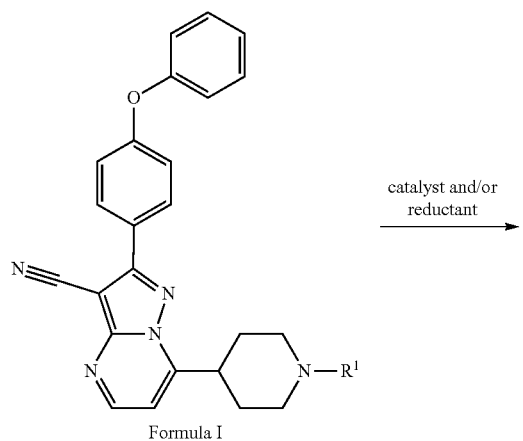
Deuterium-Labeled Compound 1

Also disclosed herein is a method for preparing the compound of Formula Ia, comprising asymmetrically reducing the compound of Formula I in the presence of the catalyst and/or reductant to produce the compound of Formula Ia, Formula I The above method was found to produce excellent enantioselectivities up to 95% ee by using the above catalyst, especially the neutral or cationic iridium catalyst system.

Also disclosed herein is a method for resolving the compound of Formula IIa to produce the compound of Formula IIb, or improving the chiral purity of the compound of Formula IIb, comprising treating the racemic compound of Formula IIa with a chiral acid,

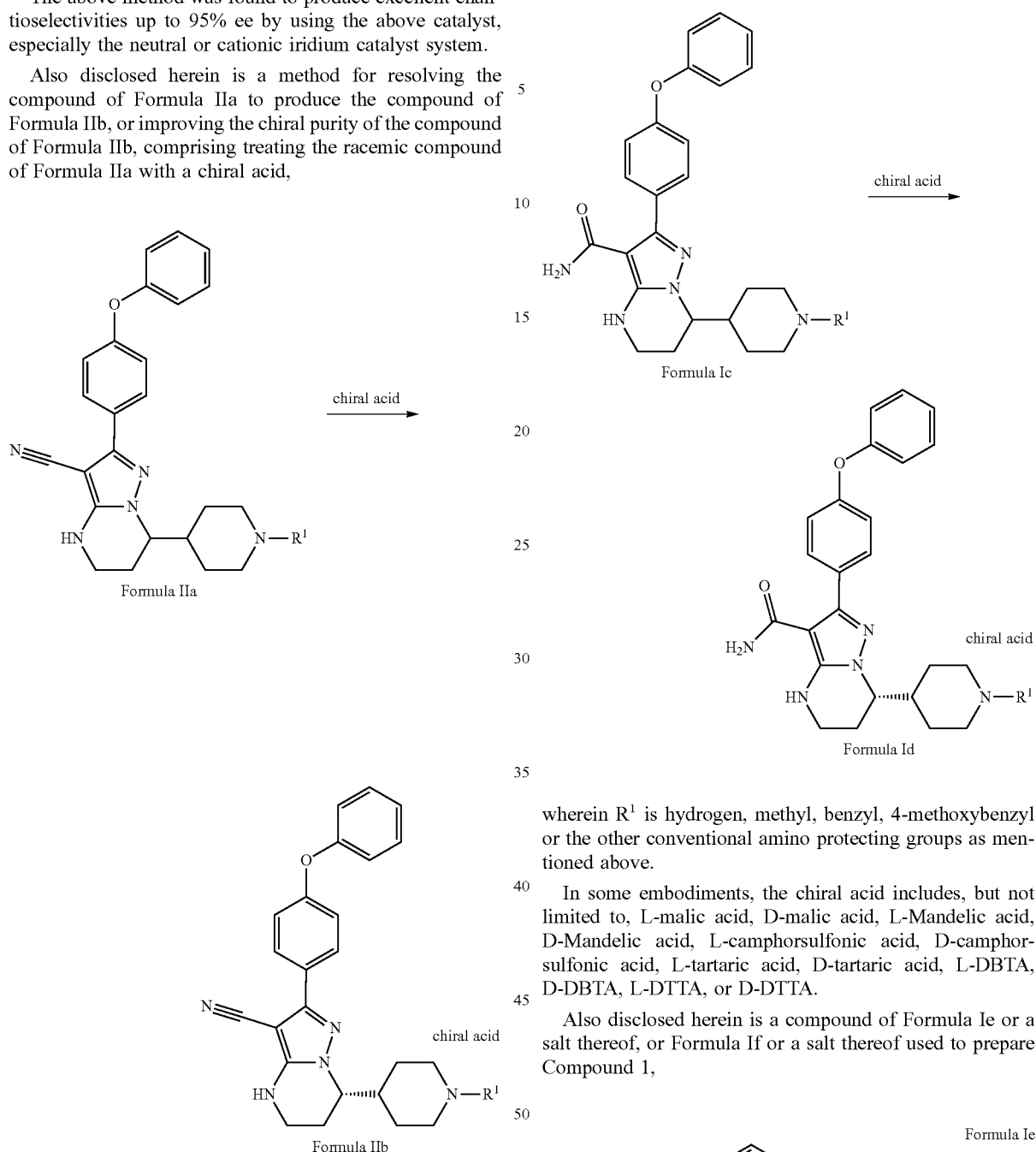

wherein $R^1$ is hydrogen, methyl, benzyl, 4-methoxybenzyl or the other conventional amino protecting groups as mentioned above.

In some embodiments, the chiral acid includes, but not limited to, L-malic acid, D-malic acid, L-Mandelic acid, D-Mandelic acid, L-camphorsulfonic acid, D-camphorsulfonic acid, L-tartaric acid, D-tartaric acid, L-DBTA, D-DBTA, L-DTTA, or D-DTTA.

Also disclosed herein is a method for resolving a compound of Formula Ic to produce a compound of Formula Id or improving the chiral purity of formula Id, comprising treating the racemic compound of Formula Ic with a chiral acid, wherein $R^1$ is hydrogen, methyl, benzyl, 4-methoxybenzyl or the other conventional amino protecting groups as mentioned above.

In some embodiments, the chiral acid includes, but not limited to, L-malic acid, D-malic acid, L-Mandelic acid, D-Mandelic acid, L-camphorsulfonic acid, D-camphorsulfonic acid, L-tartaric acid, D-tartaric acid, L-DBTA, D-DBTA, L-DTTA, or D-DTTA.

Also disclosed herein is a compound of Formula Ie or a salt thereof, or Formula If or a salt thereof used to prepare Compound 1,

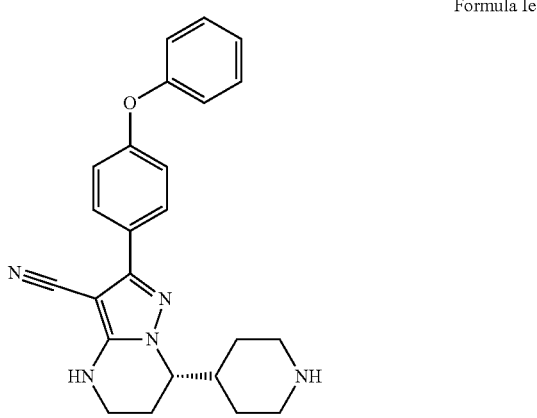 [SMILES: N#Cc1c(-c2ccc(Oc3ccccc3)cc2)nn2c1NCCC2C1CCNCC1]

Formula Ie

Formula If

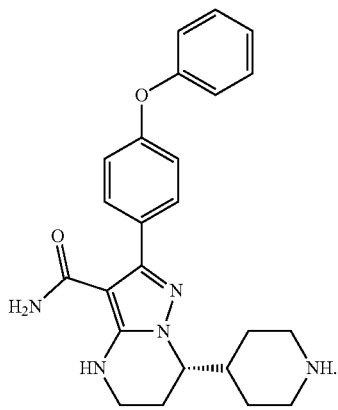

Further, the present also provides methods of preparing Crystalline Form A. The crystalline form disclosed herein can be prepared by crystallizing the compound disclosed herein from a suitable solvent system comprising at least one solvent, which can be achieved by methods of spontaneous precipitation (evaporation), cooling, and/or adding anti-solvent (in which the compound disclosed herein has relatively lower solubility), in order to achieve oversaturation in a solvent system. Crystallization can also be achieved by using or not using crystal seeds which is suitable for crystallizing the crystalline forms disclosed herein.

In some embodiments, the method of preparing Crystalline Form A comprises the steps of dissolving (S)-7-(1-acryloylpiperidin-4-yl)-2-(4-phenoxyphenyl)-4,5,6,7-tetrahydropyrazolo[1,5-a]pyrimidine-3-carboxamide (Compound 1) in DCM, swapping to solvent EA, recrystallizing from EA/MTBE, to obtain the target crystalline form.

In some embodiments, the method of preparing Crystalline Form A comprises the steps of dissolving Compound 1 in EA, adding hexane, to obtain the target crystalline form.

In some embodiments, the method of preparing Crystalline Form A is achieved by adding an anti-solvent into the solution of the solid Compound 1 or crude Form A in a solvent for dissolving the solid, wherein the anti-solvent including, but not limited to, H$_2$O and n-heptane, and the solvent for dissolving the solid including, but not limited to, acetone, DMAc, EtOAc, DCM, Toluene, and 2-MeTHF.

In some embodiments, the method of preparing Crystalline Form A is achieved by adding the solution of the solid Compound 1 or crude Form A in a solvent into an anti-solvent, and allow sufficient time for organic vapor to interact with the solution in a sealed reactor, wherein the solvent including, but not limited to, acetone, and EtOAc, and the anti-solvent including, but not limited to, n-heptane.

Also disclosed herein is a pharmaceutical composition comprises a therapeutically effective amount of Crystalline Form A, and a pharmaceutically acceptable excipient. In some embodiments, the pharmaceutical composition is used in an oral administration. In some preferred embodiments, the pharmaceutical composition comprises 1 wt % to 99 wt % of Crystalline Form A. In some more preferred embodiments, the pharmaceutical composition comprises 1 wt % to 70 wt % of Crystalline Form A. In some most embodiments, the pharmaceutical composition comprises 10 wt % to 30 wt % of Crystalline Form A.

The present invention also provide a method of treating or preventing a disease associated with undesirable Btk activity in a subject by administering to a subject Crystalline Form A.

The present invention also provide a method of treating or preventing a disease selected from an allergic disease, an autoimmune disease, an inflammatory disease, a cancer, or a combination of two or more thereof in a subject by administering to the subject Crystalline Form A.

The present invention also provide a method of treating or preventing a B-cell proliferative disease in a subject by administering Crystalline Form A to the subject.

In some embodiments, the B-cell proliferative disease is B-cell malignancies including but not limited to, lymphoma, non-Hodgkin's lymphoma (NHL), diffuse large B cell lymphoma (DLBCL), mantle cell lymphoma (MCL), follicular lymphoma (FL), chronic lymphocytic leukemia (CLL), small lymphocytic lymphoma (SLL), Waldenstrom macroglobulinemia (WM), marginal zone lymphoma (MZL), Hairy cell leukemia (HCL), Burkitt's-like leukemia (BL).

In some embodiments, the B-cell proliferative disease is relapsed/refractory (R/R) B-cell malignancies including, but limited to, R/R MCL, R/R CLL, R/R SLL, R/R WM.

The Crystalline Form A disclosed herein can be used in manufacturing a medicament for treatment of at least one disease associated with undesirable Btk activity, in a subject.

The Crystalline Form A disclosed herein can be used in manufacturing a medicament for the treatment of a disease selected from an allergic disease, an autoimmune disease, an inflammatory disease, a cancer, or a combination of two or more thereof, in a subject.

The Crystalline Form A disclosed herein can be used in manufacturing a medicament for the treatment of a B-cell proliferative disease selected from B-cell malignancies, or relapsed/refractory B-cell malignancies, in a subject.

The updated clinical trials continue to demonstrate that Compound 1 is well tolerated in treatment naive (TN) and relapsed/refractory (R/R) B-cell malignancies, eg., in WM, with a very good partial response (VGPR) rate of over 40% in an evaluable population of 42 patients and with an overall response rate (ORR) of 90% in 42 efficacy-evaluable patients with a median follow-up time of 12.3 months, and in CLL/SLL, with a high overall response rate (94%) and a very low treatment discontinuation rate (3%) at a median follow-up of 10.5 months for efficacy evaluation.

Definitions

Unless specifically defined elsewhere in this document, all other technical and scientific terms used herein have the meaning commonly understood by one of ordinary skill in the art to which this invention belongs.

As used herein, including the appended claims, the singular forms of words such as "a", "an", and "the", include their corresponding plural references unless the context clearly dictates otherwise. Thus, for example, reference to "a crystalline form" includes one or more of such different crystalline forms and reference to "the method" includes reference to equivalent steps and methods know to those of ordinary skill in the art that could be modified or substituted for the methods described herein.

As disclosed herein, the crystalline form is an approximately pure crystalline. The term "approximately pure" as herein used refers to at least 85 wt %, preferably at least 95 wt %, more preferably at least 99 wt % of Crystalline Form A disclosed herein.

For crystalline forms disclosed herein, only the main peaks (i.e, the most characteristic, significant, unique and/or reproducible peaks) are summarized; additional peaks may be obtained from the diffraction spectra by conventional methods. The main peaks described above can be reproduced within the margin of error (±2 at the last given decimal place, or ±0.2 at the stated value).

As disclosed herein, "an X-ray powder diffraction pattern substantially in accordance with FIG. 1" refers to the X-ray powder diffraction pattern that show major peaks as in FIG. 1, wherein major peaks refer to those with the relative intensity greater than 10%, preferably greater than 20%, relative to the highest peak (with its relative intensity designated to be 100%) in FIG. 1.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

The term "therapeutically effective amount" as herein used, refers to the amount of a compound that, when administered to a subject for treating a disease, or at least one of the clinical symptoms of a disease or disorder, is sufficient to affect such treatment for the disease, disorder, or symptom. The "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In the case of combination therapy, the "therapeutically effective amount" refers to the total amount of the combination objects for the effective treatment of a disease, a disorder or a condition.

The pharmaceutical composition comprising the compound disclosed herein can be administered via oral, inhalation, rectal, parenteral or topical administration to a subject in need thereof. For oral administration, the pharmaceutical composition may be a regular solid formulation such as tablets, powder, granule, capsules and the like, a liquid formulation such as water or oil suspension or other liquid formulation such as syrup, solution, suspension or the like; for parenteral administration, the pharmaceutical composition may be solution, water solution, oil suspension concentrate, lyophilized powder or the like. Preferably, the formulation of the pharmaceutical composition is selected from tablet, coated tablet, capsule, suppository, nasal spray or injection, more preferably tablet or capsule. The pharmaceutical composition can be a single unit administration with an accurate dosage. In addition, the pharmaceutical composition may further comprise additional active ingredients.

All formulations of the pharmaceutical composition disclosed herein can be produced by the conventional methods in the pharmaceutical field. For example, the active ingredient can be mixed with one or more excipients, then to make the desired formulation. The "pharmaceutically acceptable excipient" refers to conventional pharmaceutical carriers suitable for the desired pharmaceutical formulation, for example: a diluent, a vehicle such as water, various organic solvents, etc, a filler such as starch, sucrose, etc a binder such as cellulose derivatives, alginates, gelatin and polyvinylpyrrolidone (PVP); a wetting agent such as glycerol; a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, aromatics, a sweetener, and a dye.

The term "disease" refers to any disease, discomfort, illness, symptoms or indications, and can be interchangeable with the term "disorder" or "condition".

| | Abbreviations: |
|---|---|
| AcOH | Acetic acid |
| AEs | Adverse events |
| BID | Twice a day |
| CLL | Chronic lymphocytic leukemia |
| Con. | Concentrated |
| D-DBTA | (2S, 3S)-Dibenzoyl tartaric acid |
| DDQ | 2,3-Dichloro-5,6-dicyano-1,4-benzoquinone |
| DCM | Dichloromethane |
| DIEA | N,N-diisopropylethylamine |
| DLBCL | Diffuse large B cell lymphoma |
| DMAc | N,N-dimethylacetaminde |
| DMF | N,N-dimethylformamide |
| DMF-DMA | N,N-dimethylformamide dimethyl acetal |
| DMSO | Dimethylsulfoxide |
| DSC | Differential Scanning Calorimetry |
| DVS | Dynamic Vapor Sorption |
| EA | Ethyl Acetate, EtOAc |
| EDCI | 1-Ethyl-3-(3-dimethylaminopropyl) carbodiimide |
| EtOH | Ethanol |
| FL | Follicular lymphoma |
| GC | Gas Chromatograph |
| GCMS | Gas Chromatography-Mass Spectrometry |
| HOAc | Acetic Acid |
| HOBt | Hydroxybenzotriazole |
| HPLC | High Performance Liquid Chromatography |
| IPA | Isopropyl alcohol |
| IPAc | Isopropyl acetate |
| IPC | In Process Control |
| KF | Karl-Fischer |
| L-DBTA | (2R, 3R)-Dibenzoyl tartaric acid |
| LOQ | Limit of Quantification |
| MCL | Mantle cell lymphoma |
| MeCN or ACN | Acetonitrile |
| MeMgBr | Methyl Magnesium Bromide |
| MeOH | Methanol |
| 2-MeTHF | 2-Methyltetrahydrofuran |
| MIBE | 4-mehtyl-2-pentanone |
| MsOH | Methanesulfonic Acid |
| MTBE | Methyl tertiary butyl ether |
| NHL | non-Hodgkin's lymphoma |
| NLT | not less than |
| NMP | 1-Methyl-2-pyrrolidone |
| NMR | Nuclear Magnetic Resonance |
| NMT | Not more than |
| ORR | Overall response rate |
| Pd | Palladium |
| pH | Hydrogen ion concentration |
| POA | Phenoxyacetyl |
| QD | Once a day |
| RH | Relative Humidity |
| SLL | Small lymphocytic lymphoma |
| RT | Room Temperature |
| TEA | Triethylamine |
| TGA | Thermo-gravimetric Analysis |
| THF | Tetrahydrofuran |
| TN | Treatment naïve |
| VGPR | very good partial response |
| XRPD | X-ray Powder Diffraction |
| WM | Waldenstrom macroglobulinemia |

EXAMPLE

The present invention is further exemplified, but not limited, by the following examples that illustrate the invention.

Example 1

Preparation of (S)-7-(1-acryloylpiperidin-4-yl)-2-(4-phenoxyphenyl)-4,5,6,7-tetrahydropyrazolo[1,5-a]pyrimidine-3-carboxamide (Compound 1) and Crystalline Form A Thereof Step 1: Synthesis of BG-2

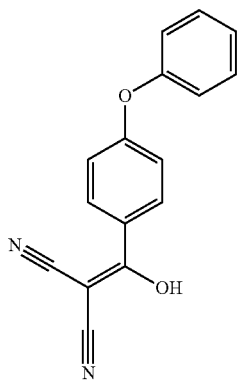

BG-2

Under nitrogen atmosphere, to a solution of EA (5 v), HOBT (1.2 eq.), EDCI (1.2 eq.), 4-phenoxybenzoic acid (BG-1, 80 Kg, 1.0 eq.) and malononitrile (1.2 eq.) was added TEA (2.4 eq.) at 10° C. The mixture was then stirred at RT until the reaction was completed. The mixture was then centrifuged and the cake was washed with EA. The filtrate was washed with aqueous NaHCO₃ twice and NH₄Cl. The organic phase was washed with 1.5 N H₂SO₄ twice and stirred. Concentrated, precipitated from methanol and purified water. The solid was collected by centrifugation and dried under vacuum. This gave 79.9 Kg of BG-2. ¹H NMR (DMSO-d₆) δ 7.62 (d, J=8.6 Hz, 2H), 7.46-7.38 (m, 2H), 7.18 (t, J=7.4 Hz, 1H), 7.06 (d, J=8.0 Hz, 2H), 6.94 (d, J=8.6 Hz, 2H).

Step 2: Synthesis of BG-3

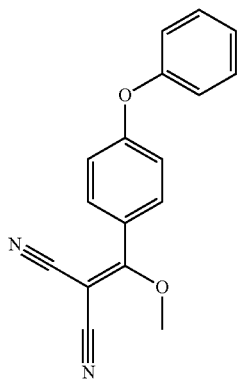

BG-3

Under nitrogen atmosphere, a solution of BG-2 (79.9 kg, 1.0 eq.) in MeCN (5.0 v) was added into trimethoxymethane (12.0 v) at 85° C. The resultant mixture was stirred until the reaction was completed. Sampled for HPLC analysis. Concentrated under vacuum. The residue was precipitated from i-PrOH and hexane. The mixture was centrifuged, and the cake was washed with hexane and dried under vacuum. This gave 71.7 Kg of product. ¹H NMR (400 MHz, DMSO-d₆) δ 7.70 (d, J=8.4 Hz, 2H), 7.52-7.45 (m, 2H), 7.28 (t, J=7.6 Hz, 1H), 7.22-7.06 (m, 4H), 3.93 (s, 3H).

Step 3: Synthesis of BG-4

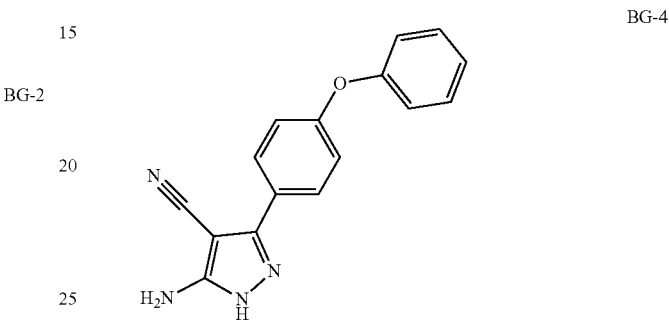

BG-4

Under nitrogen atmosphere, to a solution of BG-3 (71.6 kg, 1.0 eq.) in ethanol (2.5 v) hydrazinium hydroxide (1.0 eq) in ethanol (0.6 v) was charged dropwise to the reactor below 15° C. The solution was heated to RT and stirred until the reaction was completed. Water (4.0 v) was added to the reactor. The solution was then cooled to 5° C., centrifuged and the cake was washed with water (1.0 v). The cake was dried under vacuum. This gave 66.9 Kg of product. ¹H NMR (DMSO-d₆) δ 12.11 (br s, 1H), 7.80 (d, J=8.8 Hz, 2H), 7.46-7.39 (m, 2H), 7.18 (t, J=7.6 Hz, 1H), 7.12-7.04 (m, 4H), 6.43 (br s, 2H).

Steps 4 to 6: Synthesis of BG-8

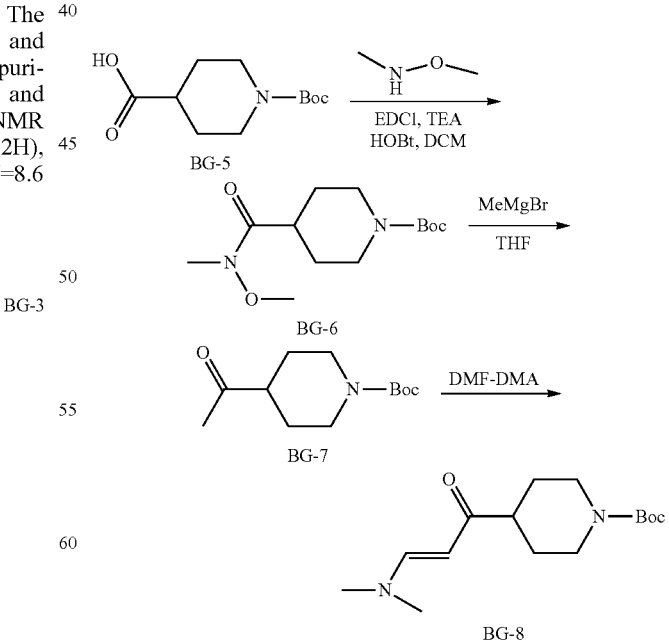

To a mixture of DCM (8.0 v), BG-5 (80.0 Kg, 1.0 eq.), V,O-dimethylhydroxylamine hydrochloride (1.2 eq.), HOBt (1.2 eq.) and EDCI (1.2 eq.), TEA (2.6 eq.) was charged dropwise below 15° C. the mixture was stirred at RT until the reaction was completed, centrifuged and the cake was washed with DCM (1.0 v) twice. The filtrate was washed with 20% aqueous NH₄Cl (3×4.0 v). The filtrate was concentrated under vacuum to give the crude product BG-6, which was used in the next step without further purification. The residue was dissolved in toluene (5.0 v) and THF (1.0 v), cooled to 10° C., charged dropwise MeMgBr (1.4 eq.) at 10° C. and then stirred at RT until the reaction was completed. The solution was cooled below 10° C. Saturated aqueous NH₄Cl was charged dropwise below 10° C. The mixture was centrifuged, separated, filtrated, and the organic phase was washed with aqueous NaCl twice. The organic phase was concentrated to give the crude product, which was used in the next step without further purification. The residue in DMF (2.5 v) and DMF-DMA (2.5 v) was stirred at 110° C. until the reaction was completed. The reaction mixture was cooled, concentrated and then DCM was added. The final mixture was washed with saturated aqueous NH₄Cl. The organic layer was concentrated and precipitated by charging hexane. The mixture was ccentrifuged and the cake was collected. The cake was dried under vacuum. This gave 82.2 Kg of the desired product. $^1$H NMR (DMSO-d$_6$) δ 7.49 (d, J=12.6 Hz, 1H), 5.01 (d, J=12.6 Hz, 1H), 3.99-3.82 (m, 2H), 3.14-2.94 (m, 2H), 2.89-2.61 (m, 6H), 2.49-2.37 (m, 1H), 1.66-1.56 (m, 2H), 1.39 (s, 9H), 1.39-1.20 (m, 2H).

Step 7: Synthesis of BG-9

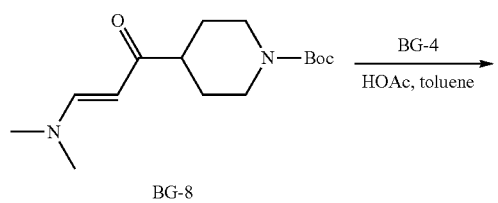

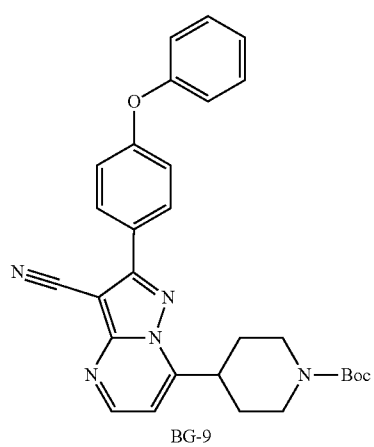

Under nitrogen atmosphere, a mixture of toluene (8.0 v), AcOH (0.5 v), BG-8 (1.2 eq.) and BG-4 (66.9 Kg 1.0 eq.) was heated to 95° C. and stirred until the reaction was completed. The mixture was cooled, concentrated and precipitated from methanol. The mixture was centrifuged and the cake was washed with methanol. The cake was dried under vacuum. This gave 107.8 Kg of product. $^1$H NMR (DMSO-d$_6$) δ 8.78 (d, J=4.6 Hz, 1H), 8.15-8.07 (m, 2H), 7.51-7.41 (m, 2H), 7.34 (d, J=4.6 Hz, 1H), 7.27-7.19 (m, 3H), 7.17-7.10 (m, 2H), 4.24-4.02 (m, 2H), 3.81-3.69 (m, 1H), 3.12-3.82 (m, 2H), 2.15-2.04 (m, 2H), 1.76-1.60 (m, 2H), 1.43 (s, 9H).

Step 8: Synthesis of BG-10

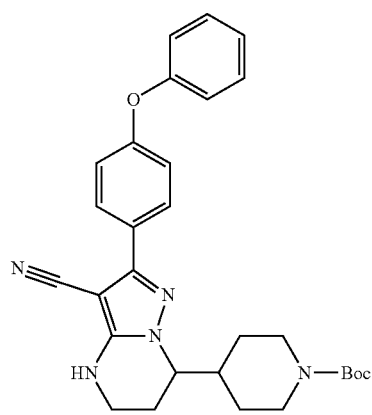

To a mixture of THF (10.0 v), BG-9 (13.0 Kg, 1.0 eq.) and D-DBTA (1.0 eq) under N₂ was charged Pd/C (10% w/w), hydrogen gas was introduced into the reactor and the hydrogen pressure was maintained to 1.8 MPa. The reactor was heated to 40° C. slowly and stirred until the reaction was completed. The mixture was then cooled, filtered, and the cake was washed with THF. The filtrate was collected, and concentrated under vacuum. DCM was added. The residue was washed with aq. NaHCO₃, concentrated and precipitated from MTBE and hexane, then centrifuged. The cake was collected and dried under vacuum to give the desired compound (yield:94.8% and purity:98.5%). $^1$H-NMR (DMSO-d$_6$) δ 7.82-7.76 (m, 2H), 7.56-7.51 (m, 1H), 7.45-7.37 (m, 2H), 7.21-7.14 (m, 1H), 7.12-7.03 (m, 4H), 4.09-3.91 (m, 3H), 3.30-3.22 (m, 2H), 2.82-2.55 (m, 2H), 2.18-1.99 (m, 2H), 1.98-1.86 (m, 1H), 1.69-1.58 (m, 1H), 1.56-1.45 (m, 1H), 1.38 (s, 9H), 1.32-1.13 (m, 2H).

Step 9: Synthesis of BG-11

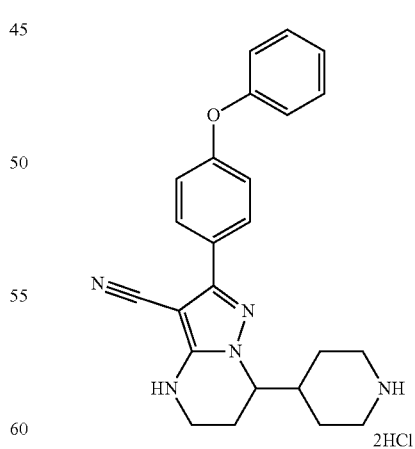

To a solution of BG-10 (100.0 Kg 1.0 eq.) in DCM (6.0 v) was added dropwise HCl in EtOH (20.9% w/w, 2.0 v) under nitrogen atmosphere. The mixture is stirred until the reaction was completed. MTBE (4.0 v) was added to the solution, cooled. The cakes was collected by centrifugation and washed with hexane (2.0 V), then the cake was slurried in hexane (5 v), and centrifuged again. The cake was washed with hexane (2.0 V) and dried under vacuum. This gave 85.2 Kg product. ¹H-NMR (DMSO-d₆) δ 9.25-8.85 (m, 2H), 7.84-7.70 (m, 2H), 7.47-7.37 (m, 2H), 7.18 (t, J=7.4 Hz, 1H), 7.12-7.03 (m, 4H), 5.73 (br s, 2H), 4.12-4.03 (m, 1H), 3.25-3.19 (m, 4H), 2.90-2.73 (m, 2H), 2.28-2.12 (m, 1H), 2.10-2.00 (m, 1H), 1.99-1.86 (m, 1H), 1.84-1.52 (m, 4H).

Step 10: Synthesis of BG-11A

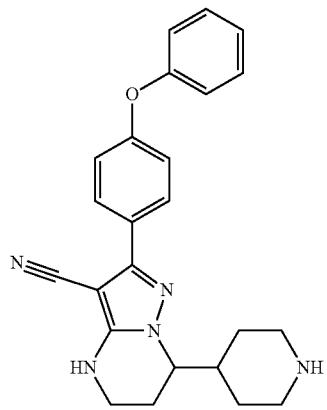

BG-11A

A mixture of BG-11 (85.0 Kg, 1.0 eq) in water (6.0 v) and NaOH (3.0 eq) was stirred until the reaction was completed at RT. The cake was collected and slurried in MTBE (6.0 v). The mixture was then centrifuged to collect the cake. The cake was dried under vacuum. This gave 71.3 Kg product. ¹H-NMR (DMSO-d₆) δ 7.82-7.74 (m, 2H), 7.54-7.49 (m, 1H), 7.45-7.38 (m, 2H), 7.21-7.14 (m, 1H), 7.12-7.04 (m, 4H), 4.03-3.95 (m, 1H), 3.29-3.21 (m, 2H), 3.00-2.87 (m, 2H), 2.46-2.31 (m, 2H), 2.11-1.83 (m, 3H), 1.58-1.12 (m, 4H).

Step 11: Synthesis of BG-11B

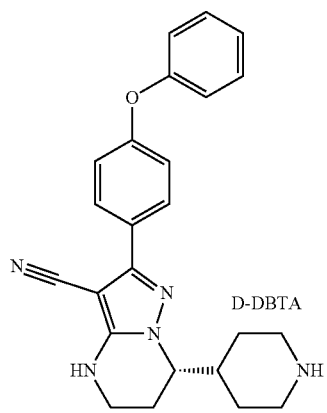

BG-11B

A mixture of enthanol/water/acetic acid (7:3:1, 46 v) and BG-11A (30 kg, 1.0 eq.) in a reactor was heated to 70±5° C. under nitrogen atmosphere, then a solution of D-DBTA (1.20 eq.) in ethanol/water/acetic acid (7:3:1, 4 v) was added dropwise with the temperature not less than 65° C. The resulting solution was stirred for 16 hrs at 60-65° C., then cooled to RT. The solid was collected by centrifugation and washed with ethanol (2.0 v). The cake was slurried in the mixed solvent of ethanol/water/AcOH (7:3:1, 20 v) for 16 hrs at 55° C. and cooled to RT. The solid was collected by centrifugation, washed with ethanol (2.0 v). The cake was dried under vacuum (Yield: 37.9%). ¹H-NMR (DMSO-d₆) δ 8.76 (br s, 2H), 7.99-7.89 (m, 4H), 7.83-7.75 (m, 2H), 7.66-7.57 (m, 3H), 7.52-7.45 (m, 4H), 7.45-7.39 (m, 2H), 7.21-7.14 (m, 1H), 7.13-7.03 (m, 4H), 5.64 (s, 2H), 4.08-4.00 (m, 1H), 3.29-3.19 (m, 4H), 2.85-2.72 (m, 2H), 2.21-1.40 (m, 7H).

Step 12: Synthesis of BG-11C

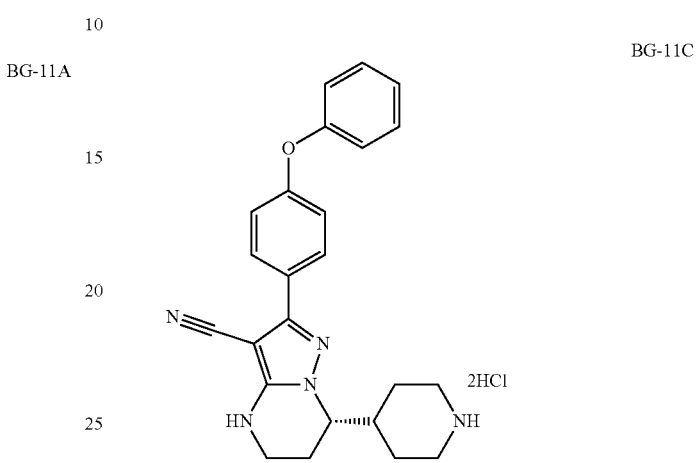

BG-11C

To a mixture of dichloromethane (15.0 v) and 20.0% aqueous KOH (3.0 v) was added bachwise BG-11B (48.0 kg, 1.0 eq.) under nitrogen atmosphere at RT. After the reaction was completed, the organic layer was collected and the water layer was extracted with dichloromethane (5.0 v). The organic layers were combined. Con. HCl (0.36 v) was added to the above organic layers at RT. The resulting mixture was stirred until the reaction was completed. The solid was collected by centrifugation and washed with dichloromethane (1.0 v). The collected solid was slurried with MTBE (6.0 v). The solid was collected by centrifugation and washed with MTBE (1.0 v), then was dried under vacuum. This gave 31.5 Kg product (Yield:100%).

Step 12: Synthesis of BG-11D (Alternative Intermediate)

ACN (5.0 v), soft water (10.0 v), KOH (5.0 eq) was charged to a reactor and stirred for at least 15 min. BG-11B (1.0 eq) was charge to the reactor in portion-wise. The mixture was stirred until the reaction was completed. The cake was collected by centrifugation, slurried in ACN (1.0 v) and soft water (5.0 v), and dried under vacuum to give the product.

Step 13: Synthesis of BG-12

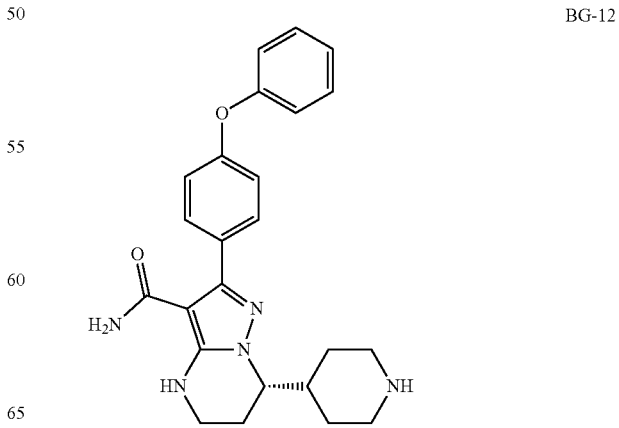

BG-12

A solution of BG-11C (15.0 Kg 1.0 eq.) in MsOH (2.5 v) was stirred at 85° C. under nitrogen atmosphere until the reaction was completed. After cooling to 5° C. purified water (4.0 v) was added dropwise to the system and kept the temperature not more than 35° C. (temperature increased obviously). The resulting solution was stirred for 16 hrs at 30° C., and then washed with DCM (2×3.0 v). The aqueous phase was collected. DCM (6.0 v) was added to the aqueous phase, the mixture was cooled to 5° C. The pH value was adjusted to 11~12 with 20% aqueous NaOH (temperature increased obviously) with stirring with the temperature not more than 30° C. The organic phase was separated and collected. The aqueous was extracted with DCM (3.0 v). The organic layers were combined and concentrated. MTBE (4.0 v) was added to the residue. The mixture was then concentrated and precipitated from n-heptane. The solid was collected by centrifugation and dried in a vacuum oven. This gave 12.55 Kg product (Yield: 94.9%). $^1$H-NMR (DMSO-$d_6$) δ 7.52-7.46 (m, 2H), 7.45-7.38 (m, 2H), 7.21-7.13 (m, 1H), 7.12-7.03 (m, 4H), 6.64 (s, 1H), 3.99-3.90 (m, 1H), 3.29-3.22 (m, 2H), 3.03-2.90 (m, 2H), 2.48-2.36 (m, 2H), 2.03 (dd, J=13.9, 5.6 Hz, 2H), 2.14-1.99 (m, 1H), 1.97-1.85 (m, 1H), 1.65-1.15 (m, 3H).

Step 14: Synthesis of BG-13

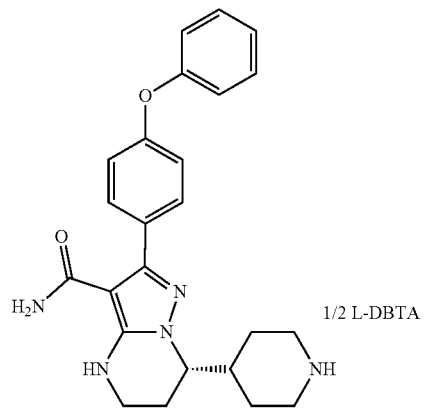

BG-13

A mixture of MeOH (13.5 v), purified water (4.5 v) and BG-12 (8.5 Kg, 1.0 eq.) in a reactor was heated to 50° C. under N$_2$ atmosphere. To the mixture was charged dropwise a solution of L-DBTA (0.7 eq) in MeOH/purified water (1.5 v/0.5 v) while keeping the temperature at 50° C. After addition, the mixture was stirred for at least 2 hrs at 50° C., and then cooled to RT and stirred for at least 16 hrs at RT. The cake was collected by Centrifugation and was washed with MeOH (2.0 v). The cake was dried in a vacuum oven. This gave 9.08 Kg product (Yield: 74.8%, ee value >98%).

Step 15: Synthesis of (S)-7-(1-acryloylpiperidin-4-yl)-2-(4-phenoxyphenyl)-4,5,6,7-tetrahydropyrazolo[1,5-a]pyrimidine-3-carboxamide (Compound 1)

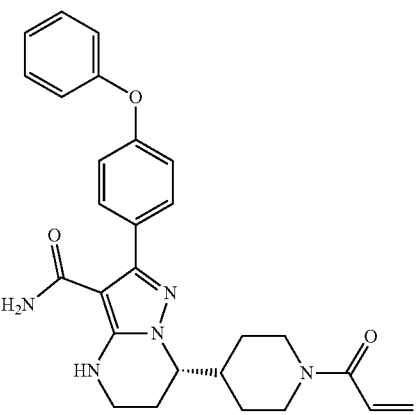 [SMILES: C=CC(=O)N1CCC([C@@H]2CCNc3c(C(N)=O)c(-c4ccc(Oc5ccccc5)cc4)nn32)CC1]

Under N$_2$ atmosphere, ACN (12.0 v), water (12.5 v), BG-13 (8.0 Kg, 1.0 eq), and NaHCO$_3$ (2.5 eq.) were added to a reactor. The mixture was then cooled to −5~0° C. To the mixture, the solution of acryloyl chloride (1.1 eq.) in MeCN (0.5 v) was added dropwise and stirred until the reaction was completed. EA (6.0 v) was then added to the reactor, and stirred. The organic phase was collected. The aqueous layer was further extracted with EA (3.0 v). The organic phases were combined and washed with brine. The organic layer was collected and concentrated.

The residue was purified by silica gel (2 wt) column, eluted with 3% w/w methanol in DCM (21.0 v). The Compound 1 solution was collected and concentrated under vacuum. The residue was precipitated from EA/MTBE (2.0 v). The cake was collected by centrifugation as the product.

Step 15: Synthesis of (S)-7-(1-acryloylpiperidin-4-yl)-2-(4-phenoxyphenyl)-4,5,6,7-tetrahydropyrazolo[1,5-a]pyrimidine-3-carboxamide (Compound 1, Alternative Method)

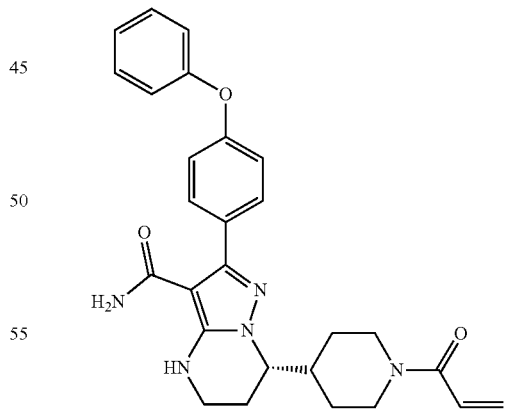

A mixture of CH$_3$CN (10.0 v), purified water (5.0 v), NaOH (1.5 eq.) and BG-13 (1.0 eq.) was stirred to get a clear solution. EtOAc (6.0 v) was then charged to the reaction and separated. The organic phase was collected and washed with 15% brine (3.0 v) twice. The organic phase prepared above was concentrated and the solvent was swapped to CH$_3$CN (residue volume: NMT 5.0 v). CH$_3$CN (7.5 v) and purified water (12.5 v) were charged and cooled to 15-20° C.

L-(+)-tartaric acid (0.5 eq) and NaHCO$_3$ (2.5 eq.) were charged to the reaction mixture. A solution of acryloyl chloride (1.1 eq.) in CH$_3$CN (0.5 v) was charged drop-wise to the reaction mixture. After the reaction was completed, EtOAc (6.0 v) was charged to the reaction mixture and organic layer was collected. Aqueous phase was further extracted with EA (3.0 v). The organic layers were combined, washed with 15% brine (5.0 v) and concentrated. The solvent was swapped to DCM (volume of residue: 1.5-2.0 v) and purified by silica gel column (silica gel: 100-200 mush; 2.0 w/w; eluent: 3% w/w MeOH in DCM (about 50 v). The collected solution was concentrated and swapped to EtOAc (4.0 v). MTBE (6.4 v) was charged drop-wise to residue at 50° C. The mixture was then cooled to 5° C. and the cake was collected centrifugation.

Step 16: Preparation of Crystalline Form A of Compound 1

The above cake of Compound 1 was dissolved in 7.0 volumes of DCM, and then swapped to solvent EA. After recrystallization from EA/MTBE, the cakes was collected by centrifugation, and was dried under vacuum. This gave 4.44 Kg product (Yield: 70.2%).

The product was then characterized by X-ray powder diffraction (XRPD) pattern method, which was generated on a PANalytical Empyrean X-ray powder diffractometer with the XRPD parameters as follows: X-Ray wavelength (Cu, kα, Kα1 (Å): 1.540598, Kα2 (Å): 1.544426; Kα2/Kα1 intensity ratio: 0.50); X-Ray tube setting (45 Kv, 40 mA); divergence slit (automatic); scan mode (Continuous); scan range (° 2TH) (3°-40); step size (° 2TH) (0.0131); scan speed (°/min) (about 10). The XRPD result found the resultant product as a crystalline shown in FIG. 1.

The differential scanning calorimetry (DSC) curves shown as in FIG. 2 was generated on a TA Q2000 DSC from TA Instruments. The DSC parameters used includes: temperature (25° C.-desired temperature); heating rate (10° C./min) ; method (ramp); sample pan (aluminum, crimped); purge gas (N$_2$). DSC result showed a sharp melting point at 139.4° C. (onset temperature).

The thermo-gravimetric analysis (TGA) curves shown as in FIG. 3 was generated on a TA Q5000 TGA from TA Instruments. The TGA parameters used includes: temperature (RT-desired temperature); heating rate (10° C./min); method (ramp); sample pan (platinum, open); purge gas (N$_2$). TGA result showed is anhydrous with no weight loss even up to 110° C.

The proton nuclear magnetic resonance ($^1$H-NMR) shown as in FIG. 4 was collected on a Bruker 400M NMR Spectrometer in DMSO-d$_6$. $^1$H-NMR (DMSO-d$_6$) δ 7.50 (d, J=8.6 Hz, 2H), 7.46-7.38 (m, 2H), 7.17 (t, J=7.6 Hz, 1H), 7.08 (d, J=7.6 Hz, 2H), 7.05 (d, J=8.8 Hz, 2H), 6.85-6.72 (m, 1H), 6.67 (s, 1H), 6.07 (dd, J=16.8, 2.2 Hz, 1H), 5.64 (dd, J=10.4 Hz, 2.2 Hz, 1H), 4.55-4.38 (m, 1H), 4.17-3.94 (m, 2H), 3.33-3.22 (m, 2H), 3.08-2.88 (m, 1H), 2.67-2.51 (m, 1H), 2.36-2.15 (m, 1H), 2.12-1.82 (m, 2H), 1.79-1.65 (m, 1H), 1.63-1.49 (m, 1H), 1.38-1.08 (m, 2H).

The carbon nuclear magnetic resonance ($^{13}$C-NMR) shown as in FIG. 5 was collected on a Bruker 400M NMR Spectrometer in DMSO-d$_6$. $^{13}$C-NMR spectra for Crystalline Form A of Compound 1.

Example 2

Preparation of Crystalline Form A of Compound 1

(S)-7-(1-acryloylpiperidin-4-yl)-2-(4-phenoxyphenyl)-4,5,6,7-tetrahydropyrazolo[1,5-a]pyrimidine-3-carboxamide (Compound 1) was prepared by the method disclosed in WO2014173289A, and further lyophilized to obtain amorphous form of Compound 1. A solution of Compound 1 (200 mg, ee value >97%) in EA (8 mL) was heated to 50° C., to the above solution was added dropwise hexane (8 mL) at 50° C. The mixture was cooled to RT and stirred for 16 hr then was filtered to give 110 mg as a white solid. The solid obtained were characterized by XRPD to be Form A.

Example 3

Preparation of Crystalline Form A of Compound 1 (Anti-Solvent Addition)

About 15 mg of sample (Crystalline Form A) was weighed into a 20-mL glass vial, followed by the addition of 0.4-1.2 mL corresponding solvent (see Table 2) to dissolve all the solid. The mixture was then magnetically stirred at the speed of 800 rpm to get a clear solution at RT. Subsequently, the relative anti-solvent (see Table 2) was added to the solution to induce precipitation or until the total amount of anti-solvent reached 15.0 mL. If no precipitation occurs, the solution was then transferred to slow evaporation at RT. The solids obtained were characterized by XRPD to be Form A.

TABLE 2

Anti-Solvent Addition Experiments

| Experiment ID | Solvent | Anti-solvent |
| --- | --- | --- |
| 1 | Acetone | H$_2$O |
| 2 | DMAc | H$_2$O |
| 3 | EtOAc | n-heptane |
| 4 | DCM | n-heptane |
| 5 | Toluene | n-heptane |
| 6 | 2-MeTHF | n-heptane |

Example 4

Preparation of Crystalline Form A of Compound 1 (Solution Vapor Diffusion)

About 15 mg of sample (Crystalline Form A) was dissolved in 0.5-1.5 mL of the corresponding solvent (acetone or EtOAc) to obtain a clear solution in a 3-mL vial. Subsequently, the solution was placed into a 20-mL vial with 3 mL of relative anti-solvent (n-heptane). The 20-mL vial was sealed with a cap and kept at RT, allowing sufficient time for organic vapor to interact with the solution. At the end of 11 days, clear solutions were transferred to evaporation at RT. The solid obtained were characterized by XRPD to be Form A.

Example 5

Stability Test of Crystalline Form A of Compound 1 and Purity of Compound 1

(1) Physical Stability Test

The Crystalline Form A of Compound 1 was stored at 80° C. for two days as a thermo-stability test, and the XRPD patterns before and after the test showed no crystal form change.

The long term stability studies of Crystalline Form A of Compound 1 showed there was no significant chemical purity change occurred when stored at 25° C./60% RH for up to 24 months (% area: T0=99.2% and T12=99.2%) and at 40° C./75% RH condition for up to 6 months (% area:

T0=99.1% and T6=99.4%). In addition, no crystal form and optical purity changes were observed when stored at 25° C./60% RH for up to 24 months and at 40° C./75% RH condition for up to 6 months.

(2) Hygroscopic Test

The dynamic vapor sorption (DVS) plots shown as in FIG. 6 was collected a SMS (Surface Measurement Systems) DVS Intrinsic. The DVS parameters used includes: temperature (25° C.); dm/dt (0.002%/min); Min. dm/dt stability duration (10 min); Max. equilibrium time (180 min); RH range (0% RH to 95% RH); RH step size (10% RH from 0% RH to 90% RH, 5% RH from 90% RH to 95% RH). As shown in FIG. 6, there is a very slight increase of mass at 80% RH, which was about 0.8% for Crystalline Form A of Compound 1.

(3) Crystallization/Recrystallization via Form A to Improve the Purity of Compound 1

Crystallization/Recrystallization via Form A is an efficient way to improve the purity of Compound 1 and control the impurities in Compound 1 to reach the acceptance criteria in the specification. See an example as shown in Table 3.

TABLE 3

Purity Changing after Crystallization/Recrystallization via Form A

| Conditions | Purity of Compound 1 |
| --- | --- |
| After Silica Gel Chromatography Purification | 98.5% area |
| After First Recrystallization | 99.3% area |
| After Second Recrystallization | 99.5% area |

Example 6

Preparation of Deuterium-Labeled (S)-7-(1-acryloylpiperidin-4-yl)-2-(4-phenoxyphenyl)-4,5,6,7-tetrahydropyrazolo[1,5-a]pyrimidine-3-carboxamide (Deuterium-Labeled Compound 1)

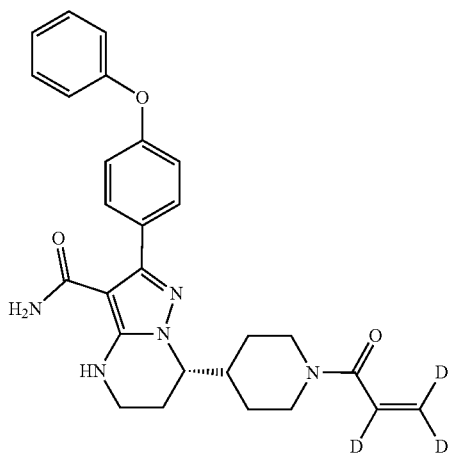 [SMILES: [2H]C([2H])=C([2H])C(=O)N1CCC([C@@H]2CCNc3c(C(N)=O)c(-c4ccc(Oc5ccccc5)cc4)nn32)CC1]

To a solution of acrylic-2,3,3-d3 acid (50 mg, 0.67 mmol) and DMF (one drop) in DCM (20 mL) was added dropwise oxalyl chloride (1.6 N, 40.9 mL, 65.5 mmol) at 0~5° C. then stirred for 2 hours at RT. The mixture was concentrated under reduced pressure to give the crude acryloyl-d$_3$ chloride.

To a solution of (S)-2-(4-phenoxyphenyl)-7-(piperidin-4-yl)-4,5,6,7-tetrahydropyrazolo[1,5-a]pyrimidine-3-carboxamide (dissociated from BG-13, see step 15, Compound 1, alternative method; 278 mg, 0.67 mmol) in DCM (20 mL) and aqu. NaHCO$_3$ (10 mL) was added dropwise a solution of the above acryloyl-d$_3$ chloride in DCM (5 mL) at 0~5° C. and stirred for 2 hours at RT. The organic combined layers were dried over anhydrous sodium sulfate, filtered, concentrated under reduced pressure and purified by prep-TLC to afford 55 mg (17.5%) of (S)-7-(1-(acryloyl-d3)piperidin-4-yl)-2-(4-phenoxyphenyl)-4,5,6,7-tetrahydropyrazolo[1,5-a]pyrimidine-3-carboxamide as an off-white solid. $^1$H NMR (400 MHz, DMSO) δ 7.50-7.44 (m, 2H), 7.42-7.35 (m, 2H), 7.17-7.10 (m, 1H), 7.09-6.99 (m, 4H), 6.64 (s, 1H), 4.52-4.40 (m, 1H), 4.10-3.95 (m, 2H), 2.29-3.25 (m, 2H), 3.04-2.86 (m, 1H), 2.63-2.50 (m, 1H), 2.32-2.13 (m, 1H), 2.06-1.81 (m, 2H), 1.75-1.45 (m, 2H), 1.35-1.08 (m, 2H). MS (ESI, m/e) [M+1]$^+$ 475.2.

Example 7

Polymorph Study of Compound 1

(1) Polymorph Study from Amorphous Form—Preparation of Form A From an Amorphous Form of Compound 1

(S)-7-(1-acryloylpiperidin-4-yl)-2-(4-phenoxyphenyl)-4,5,6,7-tetrahydropyrazolo[1,5-a]pyrimidine-3-carboxamide (Compound 1) was prepared by the method disclosed in WO2014173289A, and further lyophilized to obtain amorphous form of Compound 1.

For each experiment in Tables 4a to 4k, Tables 5a to 5e and Table 6, about 20 mg of Compound 1 as amorphous form was weighed into a glass vial, followed by the addition of corresponding solvent. The mixture was heated to give a clear solution if needed. Then the mixture was kept at RT without stirring for 1-2 days to see any solid generated from the clear solution. The solid was monitored by Polarized light microscopy.

TABLE 4a

| Experiment | Solvent | | | | Result |
| --- | --- | --- | --- | --- | --- |
| ID | EA (mL) | Hexane (mL) | RT | Heat | (1-2 d) |
| 1-1 | 0.5 | 0.1 | Y | — | No solid |
| 1-2 | 0.5 | 0.2 | Y | — | Little solid |
| 1-3 | 0.5 | 0.3 | N | Y | Oil |
| 1-4 | 0.5 | 0.4 | N | Y | Oil |
| 1-5 | 1 | 0.2 | Y | — | No solid |
| 1-6 | 1 | 0.3 | Y | — | No solid |
| 1-7 | 1 | 0.4 | Y | — | No solid |
| 1-8 | 1 | 0.5 | Y | — | No solid |
| 1-9 | 1 | 0.6 | Y | — | Little solid |
| 1-10 | 1 | 0.7 | Y | — | Little solid |
| 1-11 | 1 | 0.8 | N | Y | Oil |
| 1-12 | 1 | 0.9 | N | Y | Oil |

TABLE 4b

| Experiment | Solvent | | | | Result |
| --- | --- | --- | --- | --- | --- |
| ID | EA (mL) | Heptane (mL) | RT | Heat | (1-2 d) |
| 2-1 | 0.5 | 0.1 | Y | — | No solid |
| 2-2 | 0.5 | 0.2 | Y | — | Little solid |
| 2-3 | 0.5 | 0.3 | N | Y | Oil |
| 2-4 | 0.5 | 0.4 | N | N | Oil |
| 2-5 | 1 | 0.2 | Y | — | No solid |
| 2-6 | 1 | 0.3 | Y | — | No solid |

TABLE 4b-continued

| Experiment ID | Solvent EA (mL) | Heptane (mL) | RT | Heat | Result (1-2 d) |
|---|---|---|---|---|---|
| 2-7 | 1 | 0.4 | Y | — | No solid |
| 2-8 | 1 | 0.5 | Y | — | No solid |
| 2-9 | 1 | 0.6 | Y | — | Little solid |
| 2-10 | 1 | 0.7 | Y | — | Little solid |
| 2-11 | 1 | 0.8 | Y | — | Oil |
| 2-12 | 1 | 0.9 | N | Y | Oil |

TABLE 4c

| Experiment ID | Solvent EA (mL) | Cyclohexane (mL) | RT | Heat | Result (1-2 d) |
|---|---|---|---|---|---|
| 3-1 | 0.5 | 0.2 | Y | — | No solid |
| 3-2 | 0.5 | 0.3 | Y | — | Little solid |
| 3-3 | 0.5 | 0.4 | Y | — | Oil |
| 3-4 | 0.5 | 0.5 | Y | — | Oil |
| 3-5 | 0.5 | 0.6 | N | Y | Oil |
| 3-6 | 1 | 0.6 | Y | — | Little solid |
| 3-7 | 1 | 0.8 | Y | — | Little solid |
| 3-8 | 1 | 1.0 | Y | — | Little solid |
| 3-9 | 1 | 1.2 | Y | — | Little solid |
| 3-10 | 1 | 1.4 | Y | — | Oil |

TABLE 4d

| Experiment ID | Solvent DCM (mL) | Hexane (mL) | RT | Heat | Result (1-2 d) |
|---|---|---|---|---|---|
| 4-1 | 0.5 | 0.4 | Y | — | No solid |
| 4-2 | 0.5 | 0.6 | Y | — | No solid |
| 4-3 | 0.5 | 0.8 | Y | — | No solid |
| 4-4 | 0.5 | 1.0 | N | Y | Oil |
| 4-5 | 1.0 | 1.4 | Y | — | No solid |
| 4-6 | 1.0 | 1.6 | Y | — | No solid |
| 4-7 | 1.0 | 1.8 | Y | — | No solid |
| 4-8 | 1.0 | 2.0 | N | Y | Oil |

TABLE 4e

| Experiment ID | Solvent 1,2-Dichloro-ethane (mL) | Hexane (mL) | RT | Heat | Result (1-2 d) |
|---|---|---|---|---|---|
| 5-1 | 0.5 | 0.6 | Y | — | No solid |
| 5-2 | 0.5 | 0.8 | Y | — | No solid |
| 5-3 | 0.5 | 1.0 | Y | — | No solid |
| 5-4 | 0.5 | 1.1 | N | Y | Oil |
| 5-5 | 1.0 | 1.4 | Y | — | No solid |
| 5-6 | 1.0 | 1.6 | Y | — | No solid |
| 5-7 | 1.0 | 1.8 | Y | — | No solid |
| 5-8 | 1.0 | 2.0 | Y | — | No solid |
| 5-9 | 1.0 | 2.2 | N | Y | Oil |

TABLE 4f

| Experiment ID | Solvent MeOAc (mL) | Hexane (mL) | RT | Heat | Result (1-2 d) |
|---|---|---|---|---|---|
| 6-1 | 0.5 | 0.3 | Y | — | Little solid |
| 6-2 | 0.5 | 0.4 | Y | — | Oil |
| 6-3 | 0.5 | 0.5 | Y | — | Oil |

TABLE 4f-continued

| Experiment ID | Solvent MeOAc (mL) | Hexane (mL) | RT | Heat | Result (1-2 d) |
|---|---|---|---|---|---|
| 6-4 | 0.5 | 0.6 | N | Y | Oil |
| 6-5 | 1.0 | 0.6 | Y | — | Little solid |
| 6-6 | 1.0 | 0.8 | Y | — | Little solid |
| 6-7 | 1.0 | 1.0 | Y | — | Little solid |
| 6-8 | 1.0 | 1.2 | Y | — | Little solid |
| 6-9 | 1.0 | 1.4 | N | Y | Oil |

TABLE 4g

| Experiment ID | Solvent Toluene (mL) | Hexane (mL) | RT | heat | Result (1-2 d) |
|---|---|---|---|---|---|
| 7-1 | 1.0 | 0.2 | Y | — | Little solid |
| 7-2 | 1.0 | 0.3 | Y | — | Little solid |
| 7-3 | 1.0 | 0.4 | Y | — | Little solid |
| 7-4 | 1.0 | 0.5 | N | Y | Oil |
| 7-5 | 1.0 | 0.6 | N | Y | Oil |

TABLE 4h

| Experiment ID | Solvent Toluene (mL) | Cyclohexane (mL) | RT | Heat | Result (1-2 d) |
|---|---|---|---|---|---|
| 8-1 | 1.0 | 0.1 | Y | — | Little solid |
| 8-2 | 1.0 | 0.2 | Y | — | Little solid |
| 8-3 | 1.0 | 0.3 | Y | — | Oil |
| 8-4 | 1.0 | 0.4 | N | Y | Oil |
| 8-5 | 1.0 | 0.5 | N | Y | Little solid |
| 8-6 | 1.5 | 0.4 | Y | — | Little solid |
| 8-7 | 1.5 | 0.5 | Y | — | Little solid |

TABLE 4i

| Experiment ID | Solvent MeOAc (mL) | Cyclohexane (mL) | RT | Heat | Result (1-2 d) |
|---|---|---|---|---|---|
| 9-1 | 0.4 | 1.0 | Y | — | Little solid |
| 9-2 | 0.5 | 1.0 | Y | — | Little solid |
| 9-3 | 0.6 | 1.0 | Y | — | Little solid |
| 9-4 | 0.8 | 1.0 | Y | — | Little solid |
| 9-5 | 1.0 | 1.0 | Y | — | Little solid |

TABLE 4j

| Experiment ID | Solvent IPAC (ml) | Cyclohexane (ml) | RT | Heat | Result (2-3 d) |
|---|---|---|---|---|---|
| 10-1 | 1.0 | 0.2 | Y | — | Little solid |
| 10-2 | 1.0 | 0.4 | Y | — | Little solid |
| 10-3 | 1.0 | 0.6 | Y | — | Little solid |
| 10-4 | 1.0 | 0.8 | Y | — | Little solid |
| 10-5 | 1.0 | 1.0 | Y | — | Little solid |
| 10-6 | 1.0 | 1.2 | N | Y | Oil |

TABLE 4k

| Experiment ID | Solvent Isobutyl acetate (mL) | Cyclohexane (mL) | RT | Heat | Result (1-2 d) |
|---|---|---|---|---|---|
| 11-1 | 1.0 | 0.2 | Y | — | Little solid |
| 11-2 | 1.0 | 0.4 | Y | — | Little solid |
| 11-3 | 1.0 | 0.6 | Y | — | Little solid |
| 11-4 | 1.0 | 0.8 | Y | — | Little solid |
| 11-5 | 1.0 | 1.0 | Y | — | Little solid |
| 11-6 | 1.0 | 1.2 | N | Y | Oil |

Y = Yes, and N = No.

Table 5 Compound 1 (ee value=97%) as Starting Material

TABLE 5a

| Experiment ID | Solvent EA (mL) | Hexane (mL) | RT | Heat | Result (1-2d) |
|---|---|---|---|---|---|
| 12-1 | 1 | 0.2 | Y | — | No solid |
| 12-2 | 1 | 0.3 | Y | — | No solid |
| 12-3 | 1 | 0.4 | Y | — | No solid |
| 12-4 | 1 | 0.5 | Y | — | No solid |
| 12-5 | 1 | 0.6 | Y | — | Solid |
| 12-6 | 1 | 0.7 | Y | — | Solid |
| 12-7 | 1 | 0.8 | N | Y | Oil |
| 12-8 | 1 | 0.9 | N | Y | Oil |

TABLE 5b

| Experiment ID | Solvent EA (mL) | Heptane (mL) | RT | Heat | Result (1-2d) |
|---|---|---|---|---|---|
| 13-1 | 1 | 0.2 | Y | — | No solid |
| 13-2 | 1 | 0.3 | Y | — | No solid |
| 13-3 | 1 | 0.4 | Y | — | No solid |
| 13-4 | 1 | 0.5 | Y | — | No solid |
| 13-5 | 1 | 0.6 | Y | — | Solid |
| 13-6 | 1 | 0.7 | Y | — | Solid |
| 13-7 | 1 | 0.8 | Y | — | Oil |
| 13-8 | 1 | 0.9 | N | Y | Oil |

TABLE 5c

| Experiment ID | Solvent MeOAc (ml) | Cyclohexane (ml) | RT | Heat | Result (1-2d) |
|---|---|---|---|---|---|
| 14-1 | 0.4 | 1.0 | Y | — | No solid |
| 14-2 | 0.5 | 1.0 | Y | — | No solid |
| 14-3 | 0.6 | 1.0 | Y | — | Solid |
| 14-4 | 0.8 | 1.0 | Y | — | Solid |
| 14-5 | 1.0 | 1.0 | Y | — | No solid |
| 14-6 | 1.0 | 1.5 | Y | — | Solid |
| 14-7 | 1.0 | 2.0 | Y | — | Solid |
| 14-8 | 1.0 | 2.2 | N | Y | Oil |

TABLE 5d

| Experiment ID | Solvent EA (ml) | Cyclohexane (ml) | RT | Heat | Result (1-2d) |
|---|---|---|---|---|---|
| 15-1 | 0.5 | 0.2 | Y | — | No solid |
| 15-2 | 0.5 | 0.3 | Y | — | solid |
| 15-3 | 0.5 | 0.4 | Y | — | Oil |
| 15-4 | 0.5 | 0.5 | Y | — | Oil |
| 15-5 | 0.5 | 0.6 | N | Y | Oil |
| 15-6 | 1 | 0.6 | Y | — | solid |
| 15-7 | 1 | 0.8 | Y | — | solid |
| 15-8 | 1 | 1.0 | Y | — | solid |
| 15-9 | 1 | 1.2 | Y | — | solid |
| 15-10 | 1 | 1.4 | Y | — | Oil |

TABLE 5e

| Experiment ID | Solvent MeOAc (ml) | Hexane (ml) | RT | Heat | Result (1-2d) |
|---|---|---|---|---|---|
| 16-1 | 0.5 | 0.3 | Y | — | solid |
| 16-2 | 0.5 | 0.4 | Y | — | No solid |
| 16-3 | 0.5 | 0.5 | Y | — | No solid |
| 16-4 | 0.5 | 0.6 | N | Y | No solid |
| 16-5 | 1.0 | 0.6 | Y | — | solid |
| 16-6 | 1.0 | 0.8 | Y | — | solid |
| 16-7 | 1.0 | 1.0 | Y | — | solid |
| 16-8 | 1.0 | 1.2 | Y | — | solid |
| 16-9 | 1.0 | 1.4 | N | Y | Oil |

Y = Yes, and N = No.

Experiments in Tables 4a to 4k and Tables 5a to 5e were conducted on the same scale (i.e., the amount of the starting material—amorphous Compound 1 is about 20 mg). However, the ee value of the starting material appeared to have significant influence in the amount of the solid to be formed in each experiment. As shown in the experiments in Tables 4a to 4k starting from 90% ee of amorphous Compound 1, the solids thus formed are of little amount. The experiments in Tables 5a to 5e starting from 97% ee of amorphous Compound 1 resulted in noticeable amount of solid. Also, the obtained solid in the experiments in Tables 4a to 4k showed low ee value when crystallization from starting material with 90% ee. One solid sample from Tables 4a to 4k using EA/Hexane as crystallization system only showed 45% ee value.

The results of Table 5a were further confirmed by a scale-up experiment similar to those in Example 2, which confirmed that the resultant solid was in the desired crystalline form (Form A).

As shown in the above Tables 4a to 4k and Tables 5a to 5e, the formation of the crystalline solid may vary depending on the specific solvents, the ratio of the solvents, and so on.

The results in Table 6 further confirms that the formation of the crystalline solid depends on the specific ratio of the solvent.

TABLE 6

| Solvent-1 (0.5 mL) | Hexane V/mL | Hexane Results | MTBE V/mL | MTBE Results | Heptane V/mL | Heptane Results | Cyclohexane V/mL | Cyclohexane Results | H₂O V/mL | H₂O Results | Ether V/mL | Ether Results |
|---|---|---|---|---|---|---|---|---|---|---|---|---|
| THF | 0.4 | Little solid | 2.0 | Little solid | 0.4 | Little solid | 0.4 | Little solid | — | — | 2.0 | No solid |
| Me-THF | 0.4 | Little solid | 1.5 | No solid | 0.4 | No solid | — | — | — | — | — | — |
| DME | 0.6 | Little solid | 1.5 | No solid | 0.6 | Little solid | 0.8 | Little solid | — | — | 1.5 | No solid |
| EtOH | 2.0 | No solid | 5.0 | No solid | 2.5 | oil | 2.0 | No solid | 5.0 | No solid | 5.0 | No solid |
| i-PrOH | 1.5 | No solid | 2.5 | No solid | — | — | 2.0 | No solid | 2.0 | Little solid | — | — |
| pyridine | 1.0 | No solid | 4.0 | No solid | — | — | 1.0 | No solid | 2.0 | No solid | — | — |
| Propyl acetate | 0.3 | No solid | 0.8 | No solid | — | — | — | — | — | — | — | — |
| Isobutyl acetate | 0.2 | No solid | 2.0 | No solid | — | — | — | — | — | — | — | — |
| n-BuOH | 0.5 | No solid | 2.0 | No solid | — | — | — | — | 0.5 | No solid | — | — |
| 1,2-Dichloroethane | 1.0 | No solid | 5.0 | No solid | — | — | 1.2 | No solid | — | — | — | — |
| DCM | 1.0 | oil | 5.0 | No solid | — | — | 1.2 | No solid | — | — | — | — |
| Toluene | 0.2 | Oil and Little solid | 0.5 | No solid | 0.2 | No solid | 0.2 | Oil and Little solid | — | — | 0.5 | No solid |

(2) Polymorph Study From Crystalline Form—Preparation of Form A from Crystalline Form Slow Evaporation About 15 mg of sample (Crystalline Form A) was weighed into a 3-mL glass vial, followed by the addition of corresponding solvent or solvent mixture (see Table 7) to get a clear solution. Subsequently, the vial was covered with parafilm with 3-4 pinholes, and kept at RT to allow the solution to evaporate slowly. The solids were isolated for XRPD analysis. However, no crystal form was produced, as summarized in Table 7.

TABLE 7

Slow Evaporation Experiments

| Experiment ID | Solvent (v/v) | Solid Form |
|---|---|---|
| 1 | MeOH | Amorphous |
| 2 | EtOH | Amorphous |
| 3 | IPA | Amorphous |
| 4 | ACN | Amorphous |
| 5 | Acetone | Oil |
| 6 | EtOAc | Oil |
| 7 | THF | Oil |
| 8 | DCM | Amorphous |
| 9 | Toluene | Oil |
| 10 | Acetic acid | Oil |
| 11 | EtOH/H₂O (4:1) | Amorphous |
| 12 | Acetone/H₂O (4:1) | Amorphous |
| 13 | THF/H₂O (4:1) | Amorphous |
| 14 | DCM/n-heptane (4:1) | Amorphous |
| 15 | EtOH/n-heptane (4:1) | Amorphous |
| 16 | EtOAc/n-heptane (6.5:1) | Oil |
| 17 | ACN/MTBE (4:1) | Oil |

Anti-Solvent Addition

About 15 mg of sample (Crystalline Form A) was weighed into a 20-mL glass vial, followed by the addition of 0.4-1.2 mL corresponding solvent (see Table 8). The mixture was then magnetically stirred at the speed of 800 rpm to get a clear solution at RT. Subsequently, the relative anti-solvent (see Table 8) was added to the solution to induce precipitation or until the total amount of anti-solvent reached 15.0 mL. If no precipitation occurs, the solution was then transferred to slow evaporation at RT. Results summarized in Table 8.

TABLE 8

Anti-solvent Addition Experiments

| Experiment ID | Anti-Solvent | Solvent | Solid Form |
|---|---|---|---|
| 1 | H₂O | EtOH | Oil |
| 2 | H₂O | THF | Oil |
| 3 | H₂O | Acetic acid | Oil |
| 4 | n-heptane | 1,4-dioxane | Oil |
| 5 | MTBE | ACN | Oil |
| 6 | MTBE | NMP | N/A |
| 7 | MTBE | EtOH | Oil |
| 8 | MTBE | DCM | Oil |

N/A: no solid was obtained.

Slow Cooling

About 20 mg of sample (Crystalline Form A) was suspended in 1.0 mL of corresponding solvent (see Table 9) in a 3-mL glass vial at RT. The suspension was transferred to slurry at 50° C. using magnetic stirring with the speed of 800 rpm. The sample was equilibrated at 50° C. for 2 hrs and filtered using a 0.45 μm Nylon membrane. Subsequently, the filtrate was slowly cooled down from 50° C. at a rate of 0.1° C./min. The obtained solids were kept isothermal at 5° C. before isolated for XRPD analysis. No crystal form was obtained, as summarized in Table 9.

TABLE 9

Slow Cooling Experiments

| Experiment ID | Solvent (v/v) | Solid Form |
|---|---|---|
| 1 | IPA | N/A |
| 2 | MIBK | N/A |
| 3 | IPAc | N/A |
| 4 | Toluene | N/A |
| 5 | EtOH/H₂O (1:2) | Gel |
| 6 | Acetone/H₂O (1:2) | Gel |
| 7 | EtOAc/n-heptane (1:2) | Amorphous |
| 8 | CHCl₃/n-heptane (1:2) | N/A |
| 9 | THF/n-heptane (1:2) | Oil* |
| 10 | ACN/MTBE (1:2) | Oil* |

N/A: no solid was obtained.
*clear solution was transferred to evaporate at RT.

Solution Vapor Diffusion

About 15 mg of sample (Crystalline Form A) was dissolved in 0.5-1.5 mL of corresponding solvent (see Table 10) to obtain a clear solution in a 3-mL vial. Subsequently, the solution was placed into a 20-mL vial with 3 mL of relative anti-solvent. The 20-mL vial was sealed with a cap and kept at RT, allowing sufficient time for organic vapor to interact with the solution. At the end of 11 days, clear solutions were transferred to evaporation at RT. The solids obtained were characterized by XRPD. The results summarized in Table 10.

TABLE 10

Solution Vapor Diffusion Experiments

| Experiment ID | Solvent | Anti-solvent | Solid Form |
|---|---|---|---|
| 1 | EtOH | $H_2O$ | Amorphous* |
| 2 | ACN | $H_2O$ | N/A |
| 3 | Acetone | $H_2O$ | Amorphous* |
| 4 | THF | $H_2O$ | Amorphous* |
| 5 | Acetic acid | $H_2O$ | Oil |
| 6 | EtOH | n-heptane | N/A |
| 7 | THF | n-heptane | Amorphous* |
| 5 | DCM | n-heptane | Amorphous* |
| 8 | DMAc | MTBE | N/A |
| 9 | IPA | MTBE | N/A |
| 10 | 1,4-Dioxane | MTBE | N/A |
| 11 | Toluene | MTBE | N/A |
| 12 | NMP | MTBE | N/A |

N/A: no solid was obtained.
*solid was generated via slow evaporation.

Polymer-Induced Crystallization Experiments

About 15 mg of sample (Crystalline Form A) was dissolved in 1.0 mL of corresponding solvent (see Table 11) to obtain a clear solution in a 3-mL vial. The solution was then filtered using 0.45 μm Nylon membrane. About 2 mg of polymer mixture was added into the filtrate. The mixture was stirred at RT to induce precipitation. The solids were isolated for XRPD analysis. No crystal form was obtained, as summarized in Table 11.

TABLE 11

Polymer-induced crystallization Experiments

| Experiment ID | Solvent (v/v) | Polymer Mixture | Solid Form |
|---|---|---|---|
| 1 | EtOH | A | Amorphous |
| 2 | ACN | A | Amorphous |
| 3 | Acetone | A | Amorphous |
| 4 | THF | A | Amorphous |
| 5 | DCM | A | Amorphous |
| 6 | EtOAc | A | Amorphous |
| 7 | EtOH | B | Amorphous |
| 8 | ACN | B | Amorphous |
| 9 | Acetone | B | Amorphous |
| 10 | THF | B | Amorphous |
| 11 | DCM | B | Amorphous |
| 12 | EtOAc | B | Amorphous |

Polymer mixture A: polyvinyl pyrrolidone (PVP), polyvinyl alcohol (PVA), polyvinylchloride (PVC), polyvinyl acetate (PVAC), hypromellose (HPMC), methyl cellulose (MC) (mass ratio of 1:1:1:1:1:1)
Polymer mixture B: polycaprolactone (PCL), polyethylene glycol (PEG), poly(methyl methacrylate) (PMMA) sodium alginate (SA), and hydroxyethyl cellulose (HEC) (mass ratio of 1:1:1:1:1).

Example 8

Determination of Absolute Configuration of Compound 1

Preparation of BG-13 Single Crystal

Six single crystal growth experiments (see Table 12) were performed via slow cooling. Suitable single crystals of BG-13 were obtained by slow cooling in MeOH/$H_2O$ (1:1, v/v). The crystal data and structure refinement are listed in Table 13.

TABLE 12 single Crystal Growth Experiments

| Experiment ID | Weight (mg) | Solvent (1 mL, v/v) | Method | Temperature (° C.) | Dissolved (Y/N*) | Observation |
|---|---|---|---|---|---|---|
| 1 | 5.6 | IPA/$H_2O$ (3/1) | cooling | 60 | N | Block-like crystal |
| 2 | 5.5 | IPA/$H_2O$ (3/1) | cooling | 60 | N | Block-like crystal |
| 3 | 5.4 | IPA/$H_2O$ (3/1) | cooling | 60 | N | Block-like crystal |
| 4 | 5.5 | IPA/$H_2O$ (3/1) | cooling | 60 | N | Block-like crystal |
| 5 | 4.7 | MeOH/$H_2O$ (2/1) | cooling | 60 | N | Crystal |
| 6 | 5.5 | MeOH/$H_2O$ (1/1) | cooling | 60 | N | Crystal |

TABLE 13

Single Crystal Data and Structure Refinement of BG-13

| | | |
|---|---|---|
| Empirical formula | $C_{33}H_{34}N_5O_6$ | — |
| Formula weight | 596.65 | — |
| Temperature | 173.15 | — |
| Wavelength | 1.54178 Å | — |
| Crystal system, space group | monoclinic | C2 |
| Unit cell dimensions | a = 16.7939(4) Å | alpha = 90.00 deg.. |
| | b = 7.9871(2) Å | beta = 108.0460(10) deg. |
| | c = 23.5438(5) Å | gamma = 90.00 deg. |
| Volume | 3002.69(12) Å$^3$ | — |
| Z, Calculated density | 4 | 1.320 mg/mm$^3$ |
| Absorption coefficient | 0.756 mm$^{-1}$ | — |
| F(000) | 1260.0 | — |
| Crystal size | 0.3 × 0.21 × 0.08 mm$^3$ | — |

TABLE 13-continued

| | | |
|---|---|---|
| Theta range for data collection | 1.97 to 64.96 deg. | — |
| Limiting indices | $-19 <= h <= 17$, | — |
| | $-7 <= k <= 9$, | — |
| | $-27 <= l <= 24$ | — |
| Reflections collected/unique | 5073/3756[R(int) = 0.1062] | — |
| Completeness | 92.8% | — |
| Refinement method | Full matrix least squares on $F^2$ | — |
| Data/restraints/parameters | 3756/1/398 | — |
| Goodness-of-fit on $F^2$ | 1.192 | — |
| Final R indices [I > 2sigma(I)] | $R_1 = 0.0819$ | $wR_2 = 0.294$ |
| Absolute structure Flack | 0.0(3) | — |
| Largest diff. peak and hole | 0.50 and $-0.57$ e·$A^{-3}$ | — |

The data of single crystal were gemnerated on a Bruker APEX DUO single-crystal diffractometer with CCD dector (Cu K$\alpha$, $\lambda$ = 1.54178 Å, 173.15K).

BG-13 was confirmed to be a (2R, 3R)-dibenzoyl tartaric acid (L-DBTA) salt and the molar ratio of freebase to L-DBTA is 2:1. Configuration of both carbons (C32 and C32') in L-DBTA was confirmed to be R. Configuration of C6 in freebase was determined to be S, as shown in FIG. 8 to FIG. 10. A powder X-ray diffraction pattern method was also used to characterize the structure of the single crystals, as shown in FIG. 11.

Absolute Configuration of Compound 1

The absolute configurations of Compound 1 was deduced to be S from the single crystal X-ray structural analysis of intermediate BG-13.

Example 9

Chiral Resolution of BG-11A

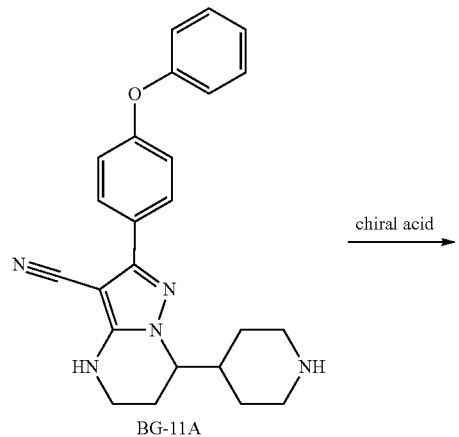

BG-11A chiral acid →

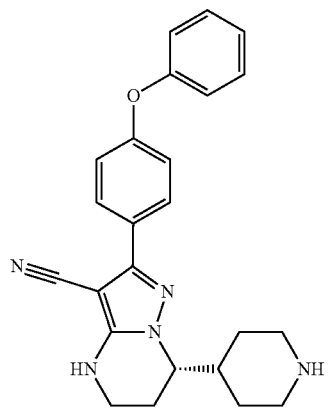

General procedure: To a solution of compound BG-11A in a prepared solvent system was added a chrial acid at elevated temperature. After stirring at this temperature, it was cooled to RT and stirred overnight at RT. The solid was filtered and washed with the prepared solvent system. The ee value was tested by chiral HPLC directly from the related salt or its Boc-derivative (see Table 14). Other chiral acids or solvent system gave no ee value, low ee value or not desired chiral compound.

TABLE 14

Chiral Resolution of BG-11A

| Solvent System | Amount of 11A | Chiral acid | temperature | ee value | Yield |
|---|---|---|---|---|---|
| EtOH/H$_2$O/AcOH 7/3/1 (1.9 L) | 40.0 g | D-DBTA (0.5 eq.) | 70° C. to RT | >85% ee | 42.2% |
| i-PrOH/H$_2$O/AcOH 7/3/1 (25 mL) | 500 mg | D-DBTA (1.0 eq.) | 70° C. to RT | 77% ee | 38.5% |
| i-PrOH/H$_2$O/AcOH 7/3/1 (25 mL) | 500 mg | D-DBTA (0.5 eq.) | 70° C. to RT | 85% ee | 38.9% |
| EtOH/H$_2$O/AcOH 7/3/1 (25 mL) | 500 mg | D-DBTA (0.5 eq.) | 70° C. to RT | 86% ee | 39.8% |
| MeOH/H$_2$O/AcOH 7/3/1 (25 mL) | 500 mg | D-DBTA (0.5 eq.) | 70° C. to RT | 82% ee | 42.2% |
| AcOH/H$_2$O 3/1 (40 mL) | 1 g | D-DBTA (0.55 eq.) | 60° C. to RT | 83% ee | 27.6% |

TABLE 14-continued

| Chiral Resolution of BG-11A | | | | | |
|---|---|---|---|---|---|
| Solvent System | Amount of 11A | Chiral acid | temperature | ee value | Yield |
| 1,4-dioxane/H2O 1/1 (2.5 mL) | 25 mg | D-DBTA (2.0 eq.) | 60° C. to RT | No Solid | No Solid |
| MeOH/H$_2$O 1/1 (2.5 mL) | 25 mg | D-DBTA (2.0 eq.) | 60° C. to RT | 36% ee | Not weigh |
| CH$_3$CN/H$_2$O 9/1 (2.5 mL) | 25 mg | D-DBTA (2.0 eq.) | 60° C. to RT | 14% ee | Not weigh |
| CH$_3$CN/H$_2$O 6/1 (2.5 mL) | 25 mg | D-DBTA (2.0 eq.) | 60° C. to RT | 89% ee | Not weigh |
| i-PrOH/H$_2$O 1/1 (2.5 mL) | 25 mg | D-DBTA (2.0 eq.) | 60° C. to RT | 79% ee | Not weigh |
| CH$_3$CN/H$_2$O 4/1 (1 mL) | 50 mg | D-DBTA (1.0 eq.) | 60° C. to RT | 24% ee | 46% |
| CH$_3$CN/H$_2$O 4/1 (1.5 mL) | 50 mg | D-DBTA (1.0 eq.) | 60° C. to RT | 91% ee | 33.7% |

Example 10

Chiral Resolution of BG-12A and Improve the Chiral Purity

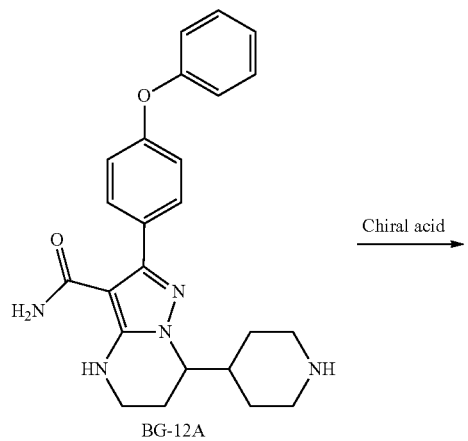

BG-12A

→ Chiral acid

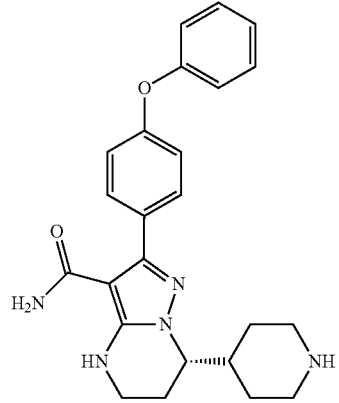

General procedure: To a solution of compound BG-12A in a prepared solvent system was added chrial acid in at elevated temperature. After stirring at this temperature, it was cooled to RT and stirred overnight at RT. The solid was filtered and washed with the prepared solvent system. The chiral purity was tested by chiral HPLC directly from the related salt or free base (see Table 15). Other chiral acids or solvent system gave no ee value, low ee value or not desired chiral compound.

TABLE 15

| Chiral Resolution of BG-12A | | | | | |
|---|---|---|---|---|---|
| Solvent System | Amount of BG-12A | Chiral acid | Temperature | ee value | Yield |
| MeOH/H$_2$O 3/1 (1500 mL) | 50 g | L-DBTA (0.35 eq.) | 50° C. to RT | 85.6% ee | 43.1% |
| EtOH/H$_2$O 6/1 (250 mL) | 14.4 g | L-DBTA (0.55 eq.) | 78° C. to RT | 79.1% ee | 41.8% |
| n-BuOH/H$_2$O 6/1 (20 mL) | 1 g | L-DBTA (0.8 eq.) | 80° C. to RT | 95% ee | 20% |
| MeOH (4 mL) | 500 mg | L-DBTA (1.1 eq.) | Reflux to RT | No solid | |
| EtOH (17 mL) | 1.0 g | L-DBTA (1.1 eq.) | Reflux to RT | 40% ee | Not weigh |
| EtOH (30 mL) | 500 mg | L-DBTA (2.2 eq.) | Reflux to RT | No ee | Not weigh |

The obtained L-DBTA salt (31 g, 85.6% ee) was added to THF/H$_2$O (1/1, 1034 mL), the suspension was warmed to 70° C. and stirred until all solid dissolved. Then 517 mL of water was added. The solution was then slowly cooed to 40° C. and added seed crystal (10 mg). After stirring for about 2 hrs, the solution was slowly cooled to ambient temperature and stirred for 2 days. Filtered, the solid was washed with THF/H$_2$O=1/1 (20 mL) and dried over under reduced pressure to give the product as a white solid (22.5 g, 72% yield, >98.5 ee value).

The obtained free base (6.02 g, 79.1% ee) was dissolved in (1 g/15 mL) EtOH/H$_2$O (6/1, 90 mL), stirred at 78° C. allowing all the starting material to be dissolved. Then, a solution of L-DBTA (2.84 g, 7.9 mmol, 0.55 eq) in EtOH/H$_2$O (6/1, 7 mL) was added. The solid quickly formed, the mixture was stirred at this temperature for 1 h before removing the heating system. The mixture was allowed to cool to RT. Filtered, the solid was washed with EtOH/H$_2$O (6/1, 10 mL). The collected solid was converted to free base using in NaOH aqueous solution and DCM to get the product (4.7 g, yield: 32.6%, 93% ee) as a white foam.

A suspension of the obtained free base (70.0 g, 90.5% ee) in CH$_3$CN/H$_2$O (1/1, 700 mL) was heated to 60° C. to give a clear solution. To the above solution was then added L-DBTA (33 g, 0.55 eq). After stirring at 60° C. for about 2 hr, the mixture was slowly cooled to RT and stirred for overnight. Filtered, the solid was washed with CH$_3$CN/H$_2$O (1/1, 50 mL), dried over under reduced pressure to give the product as a off-white solid (80 g, yield: 80% ee value >98%).

Example 11

Efficacy Tests (S)-7-(1-acryloylpiperidin-4-yl)-2-(4-phenoxyphenyl)-4,5,6,7-tetrahydropyrazolo[1,5-a]pyrimidine-3-carboxamide was tested hereinafter by using its Crystalline Form A.

Test 1: Inhibition and Selectivity of the Kinases

Methods:
(1) BTK Kinase Enzymatic Assays

Crystalline Form A of Compound 1 was tested for inhibition of BTK kinase (aa2-659, Cama Biosciences) in assays based on the time-resolved fluorescence-resonance energy transfer (TR-FRET) methodology. The assays were carried out in 384-well low volume black plates in a reaction mixture containing BTK kinase, 5 μM ATP, 2 μM peptide substrate and 0-10 μM compound in buffer containing 50 mM Tris pH 7.4, 10 mM MgCl$_2$, 2 mM MnCl$_2$, 0.1 mM EDTA, 1 mM DTT, 0.005% Tween-20, 20 nM SEB and 0.01% BSA. The kinase was incubated with compound for 60 minutes at room temperature and the reaction was initiated by the addition of ATP and peptide substrate. After reaction at room temperature for 60 minutes, an equal volume of stop/detection solution was added according to the manufacture's instruction (CisBio Bioassays). The stop/detection solution contained Eu$^{3+}$ cryptate-conjugated mouse monoclonal antibody (PT66) anti-phosphotyrosine and XL665-conjugated streptavidin in buffer containing 50 mM HEPES pHn 7.0, 800 mM KF, 20 mM EDTA, and 0.1% BSA. Plates were sealed and incubated at room temperature for 1 hour, and the TR-FRET signals (ratio of fluorescence emission at 665 nm over emission at 620 nm with excitation at 337 nm wavelength) were recorded on a PHERAstar FS plate reader (BMG Labtech). Phosphorylation of peptide substrate led to the binding of anti-phosphotyrosine antibody to the biotinylated peptide substrate, which places fluorescent donor (Eu$^{3+}$ crypate) in close proximity to the accepter (Streptavidin-XL665), thus resulting in a high degree of fluorescence resonance energy transfer from the donor fluorophore (at 620 nm) to the acceptor fluorophore (at 665 nm). Inhibition of BTK kinase activity resulted in decrease of the TR-FRET signal. The IC$_{50}$ for Compound 1 was derived from fitting the data to the four-parameter logistic equation by Graphpad Prism software.

(2) Biochemical Kinase Selectivity

Selectivity of Crystalline Form A was profiled against a panel of 342 kinases at 1 □M at Reaction Biology Corp.. Crystalline Form A displayed less than 70% inhibition against 329 kinases, and greater than 70% inhibition against 13 kinases including BTK. IC$_{50}$s of Crystalline Form A (see Table 13), including ITK, TEC, JAK3 and EGFR assays carried out in-house at BeiGene by using a TR-FRET assay and corresponding peptides as the substrate.

IC$_{50}$ determination of ITK: The protocol of ITK assay is similar to BTK assay except for the following modification: 3 μM ATP and 2 μM TK substrate were used in the kinase reaction.

IC$_{50}$ determination of TEC: The protocol of Tec assay is similar to BTK assay except for the following modifications: 1) 280 μM ATP and 2 nM Poly-GT substrate were used in the kinase reaction; 2) the reaction buffer doesn't contain SEB.

IC$_{50}$ determination of JAK3: The protocol of JAK3 assay is similar to BTK assay except for the following modifications: 1) 3.4 μM ATP and 3 μM peptide substrate (B-EE-15, Biotin-EQEDEPEGDYFEWLE) were used in the kinase reaction; 2) the reaction buffer contains 50 mM Tris pH 7.8, 10 mM MgCl$_2$, 5 mM DTT, 0.01% Triton X-100 and 0.01% BSA.

IC$_{50}$ determination of EGFR: The protocol of EGFR assay is similar to BTK assay except for the following modifications: 1) 20 μM ATP, 1.44 μM TK substrate-biotin (one universal substrate for tyrosine kinases) and 0-1000 nM compound (the final concentration of 1% DMSO) were used in the kinase reaction; 2) the reaction buffer contains 50 mM HEPES pH 7.5, 10 mM MgCl$_2$, 1 mM EGTA, 0.01% Brij-35, 2.5 mM DTT and 0.1% BSA; 3) the stop/detection solution buffer contains 25 mM HEPES pH 7.5, 400 mM KF, 50 mM EDTA, 0.01% Triton-X100 and 0.1% BSA.

Results:

IC$_{50}$ of Crystalline From A for BTK kinase was 0.27 nM. Crystalline Form A was shown to be a potent, specific and irreversible BTK kinase inhibitor. In terms of its selectivity, Crystalline Form A inhibited only 13 other kinases more than 70% when profiled against a panel of 342 human kinases at 1 μM.

TABLE 16

Enzymatic Inhibition Activities of Crystalline Form A

| Enzyme | IC$_{50}$ (nM) |
|---|---|
| BTK | 0.27 |
| ITK | 53 |
| TEC | 1.9 |
| JAK3 | 600 |
| EGFR | 3.6 |
| BLK | 1.13 |
| BMX/ETK | 0.62 |
| BRK | 33 |
| ERBB4/HER4 | 1.58 |
| FGR | 155 |

TABLE 16-continued

Enzymatic Inhibition
Activities of Crystalline Form A

| Enzyme | IC$_{50}$ (nM) |
|---|---|
| FRK/PTK5 | 379 |
| LCK | 187 |
| TXK | 2.95 |

Note:
BTK, EGFR, ITK, TEC and JAK3 assays were carried out by using a TR-FRET assay and corresponding peptides as substrate. IC$_{50}$s of Crystalline Form A were measured at K$_M$ of ATP for the five kinases and with 1-hour pre-incubation. HER4, BMX, TXK, BLK FGR, LCK, FRK/PTK5 assays were carried out at Reaction Biology Corp. using $^{33}$P-ATP and filter-binding assay. IC$_{50}$s of Crystalline Form A were measured at 1M ATP and with 1-hour pre-incubation.

kinases and with 1-hour pre-incubation. HER4, BMX, TXK, BLK FGR, LCK, FRK/PTK5 assays were carried out at Reaction Biology Corp. using 33P-ATP and filter-binding assay. IC$_{50}$s of Crystalline Form A were measured at 1 □M ATP and with 1-hour pre-incubation.

Test 2: BTKpY223 Cellular Assay by Crystalline Form A

Methods:

BTKpY223 cellular assay is a HTRF based assay intended to quantitatively determine the endogenous levels of phosphorylationat BTK Tyr223. Phosphorylated Tyr223 is necessary for full activation of BTK. The assay was performed in Ramos cells (CRL-1596, ATCC) with a BTKpY223 assay kit (63IDC000, Cisbio).

Briefly, Ramos cells were serum starved in 0.5% FBS-containing RPMI1640 for 2 hours. Following starvation, the cells were incubated with Crystalline Form A to be detected at various concentrations in a CO$_2$ incubator for 1 hour. After incubation, cells were stimulated with 1 mM pervanadate (PV) or Na$_3$VO$_4$ (OV) for 20 min. Then, the cells were spun down and lysed with 1× lysis buffer at RT for 10 min (4× lysis buffer supplied in the kit). During incubation, 1× antibody mix was prepared by diluting anti-BTK-d2 and anti-pBTK-K in detection buffer (supplied in the kit). 2 ul/well of 1× antibody mixture was dispensed into the OptiPlate-384 assay plate (6005620, Perkin Elmer). After that, 18 μL of cell lysate was transferred to the assay plate pre-loaded with antibody solution. After mixing gently and spinning briefly, the plate was sealed up and kept in dark at RT for 18 hours. The fluorescence emission was measured at two different wavelengths (665 nm and 620 nm) on a compatible HTRF reader (PHERAstar FS, BMG). The potency of Compound 1 was calculated basing on the inhibition of ratio between signal intensities at 665 nm and 620 nm. IC$_{50}$ values were calculated with GraphPad Prism software using the sigmoidal doseresponse function.

Results:

Crystalline Form A inhibited the phosphorylation of BTK in the B cell lymphoma cell line, Ramos, at concentration as low as 1.8±0.2 nM (n=3).

Test 3: Effects of Crystalline Form A on Tumor Cell Proliferation in Haematological Cancer Lines (Rec-1, Mino, JEKO-1 and TMD-8)

Methods:

3 MCL cell lines (Rec-1, Mino and JEKO-1) and an ABC type diffuse large B-cell lymphoma cell line (TMD8) were used in this study. Cell lines were maintained in RPMI-1640 supplemented with 10% fetal bovine serum/FBS (Thermo Scientific); 100 units/ml penicillin (Gibco) and 0.1 mg/ml streptomycin (Gibco) and kept at 37° C. in a humidified atmosphere of 5% CO$_2$ in air. Cell lines were reinstated from frozen stocks that were laid down within 30 passages from the original cells purchased.

The growth-inhibitory activity of compounds in Rec-1, Mino, JEKO-1 and TMD-8 cells was determined using CellTiter-Glo luminescent cell viability assay (Promega). The number of cells seeded per well of a 96-well plate was optimized for each cell line to ensure logarithmic growth over 6 days treatment period. Cells were treated in triplicate with a 10-point dilution series. Following a 6-day exposure to the compound, a volume of CellTiter-Glo reagent equal to the volume of cell culture medium present in each well was added. Mixture was mixed on an orbital shaker for 2 minutes to allow cell lysis, followed by 10 minutes incubation at room temperature to allow development and stabilization of luminescent signal, which corresponded to quantity of ATP and thus the quantity of metabolically active cells. Luminescent signal was measured using PHERAstar FS reader (BMG Labtech). IC$_{50}$ values for cell viability were determined with GraphPad Prism software and were the mean of 3 independent assays.

Results:

Crystalline Form A of Compound 1 exhibited specific and potent inhibitory effect on cellular proliferation in 3 MCL cell lines and an ABC type diffuse large B-cell lymphoma cell line (TMD8) (Table 17).

TABLE 17

Inhibition of Crystalline Form A on hematic tumor cell proliferation

| Cell line | Cell Type | Potency IC50(nM) | Standard deviation(nM) |
|---|---|---|---|
| Rec-1 | MCL | 0.36 | 0.03 |
| Mino | MCL | 3.8 | 1.8 |
| JEKO-1 | MCL | 20.0 | NA |
| TMD-8 | DLBCL(ABC) | 0.54 | 0.3 |

Test 4: Pharmacokinetics Study of Crystalline Form A in Mouse

Methods:

For time course study, mice were randomly assigned into 7 groups with 4 mice per group. Mice were treated with single dose of Crystalline Form A of Compound 1 and euthanized using carbon dioxide at different time points (30 minutes, 1, 2, 4, 12, 24 hrs) after dosing. For dose dependency study, mice were randomly assigned into 9 groups with 4 mice per group. Mice were treated with different dose levels of Crystalline Form A of Compound 1 and euthanized using carbon dioxide at 4 hrs after dosing. Treatments were administered by oral gavage (p.o.) in a volume of 10 ml/kg body weight. Body weight was assessed immediately before dosing and volume dosed was adjusted accordingly.

PK SAMPLE PREPARATION: For time course study, blood samples (50 μL per mouse) were collected from the retro-orbital sinus under isoflurane/oxygen anesthesia at 15 min after dosing (this group of mice were also used for 24 hr time point) or heart puncture after euthanization for the other time points. For dose dependency study, blood samples were collected from the retro-orbital sinus under isoflurane/oxygen anesthesia at 30 minutes after dosing. Plasma was collected by centrifugation at 3,000 g for 10 minutes and was kept frozen in −80° C. until analysis.

PK Analysis: maximum plasma concentration (Cmax) and time to reach Cmax (Tmax) were taken directly from the plasma concentration versus time profiles.

Results:

Crystalline Form A was quickly absorbed and eliminated in ICR mice.

Test 5: Efficacy Study of Crystalline Form A for in TMD-8 Xenograft Model

Tumor Implantation Methods:

Animals were pre-treated with cyclophosphamide (prepared in saline, 150 mg/kg i.p.) and disulfiram (prepared in 0.8% Tween 80 in saline, 125 mg/kg p.o., one hour after each dose of cyclophosphamide) once daily for two days. Animals were then inoculated with TMD-8 cells 24 hours after the second dose of cyclophosphamide. On the day of implantation, cell culture medium was replaced with fresh medium. Four hours later, media was removed and cells were collected as described above. Cells were re-suspended in cold (4° C.) PBS and same volume of matrigel (BD, Cat #356237) was added to give a final concentration of $2.5 \times 10^7$ cells/ml. Resuspended cells were placed on ice prior to inoculation The right axilla region of each mouse was cleaned with 75% ethanol prior to cell inoculation. Each animal was injected subcutaneously with $5 \times 10^6$ cells in 200 µl of cell suspension in the right front flank via a 26-gauge needle.

For in vivo efficacy studies, starting from day 3 after cell inoculation, animals were randomly assigned into desired number of groups with 10 mice per group. Mice were treated twice daily (BID) with vehicle (0.5% carboxymethylcellulose (CMC)+0.2% Tween 80), and different dose levels of Crystalline Form A of Compound 1 for 39 days. Treatments were administered by oral gavage (p.o.) in a volume of 10 ml/kg body weight. Body weight was assessed immediately before dosing and volume dosed was adjusted accordingly. Tumor volume was measured twice weekly in two dimensions using a calliper (measureable from day 11 post inoculation in this study). Tumor volume was calculated using the formula: $V=0.5 \times (a \times b^2)$ where a and b are the long and short diameters of the tumor, respectively. Statistical analysis was conducted using the student T-test. P<0.05 was considered statistically significant. One individual was responsible for tumor measurement for the entire duration of the study. Body weights were also recorded twice weekly. Mice were also being monitored daily for clinical signs of toxicity for the duration of the study.

Results:

In vivo efficacy of Crystalline Form A was examined in TMD-8 DLBCL xenografts grown subcutaneously in NOD/SCID mice. Following daily oral administration at well tolerated at different dose levels twice daily (BID), Crystalline Form A of Compound 1 induced dose-dependent anti-tumor effects. Crystalline Form A of Compound 1 at lowest dose tested already showed strong anti-tumor activity. All treatment groups had no significant impact on animal body weight throughout the study.

Test 6: Efficacy Study of Crystalline Form A in Systemic REC-1 Xenograft Model Tumor Implantation Methods:

Animals were pre-treated with cyclophosphamide (prepared in saline, 150 mpk i.p.) and disulfiram (prepared in 0.8% TW-80 in saline, 125 mpk p.o., one hour after each dose of cyclophosphamide) once daily for two days. Animals were then inoculated with REC-1 cells 24 hours after the second dose of cyclophosphamide. On the day of implantation, cell culture medium was replaced with fresh medium. Four hours later, media was removed and cells were collected as described above. Cells were re-suspended in cold (4° C.) PBS to give a final concentration of $1 \times 10^8$ cells/ml. Resuspended cells were placed on ice prior to implantation. Each animal was injected intravenously via tail vein with $1 \times 10^7$ cells in 100 µl of cell suspension.

For in vivo efficacy studies, starting from day 8 after cell inoculation, animals were randomly assigned into desired number of groups with 10 mice per group. Mice were treated either twice daily (BID) with vehicle (0.5% carboxymethylcellulose (CMC)+0.2% Tween 80), different dose levels of Crystalline Form A of Compound 1 for 71 days. All dosing was stopped on day 78 after inoculation. Treatments were administered by oral gavage (p.o.) in a volume of 10 ml/kg body weight. Body weight was assessed immediately before dosing and volume dosed was adjusted accordingly. Body weight was recorded twice weekly (changed to three times per week from day 33). Mice were also watched daily for clinical signs of sickness for the duration of the study. The endpoint of the study is overall survival. In the case of severe toxic effect, such as loss of movement, mice were euthanized and scored as death.

For Data Analysis: Survival analysis was performed by Kaplan-Meier method. The survival time was defined as the time from the day of tumor cell inoculation to the date of animal death or being euthanized. For each group, median survival time (MST), range of survival time (RST) with 95% confidence interval and increase in life-span (ILS) were calculated. Median survival is defined as the time when 50% of mice have died. ILS was calculated using the following formula:

$$\% \text{ ILS} = (\text{MST} - \text{MST}_{(vehicle)}/\text{MST}_{(vehicle)}) \times 100$$

Statistical analysis was conducted between each group using Gehan-Breslow-Wilcoxon Test. P<0.05 was considered as statistically significant.

Results:

Crystalline Form A of Compound 1 demonstrated dose-dependent anti-tumor activity against systemic REC-1 MCL engrafts in NOD/SCID mice. Crystalline Form A of Compound 1 was significantly effective in this xenograft model.

Test 7: Toxicology of Crystalline Form A

A comprehensive nonclinical toxicity study program, including 28-day GLP studies in rats and dogs and several investigational studies, was conducted for the evaluation of the preclinical safety of Crystalline Form A of Compound 1 at different doses. These studies took account the available regulatory guidance for preclinical development of anticancer drugs. In these studies, Compound 1 demonstrated a favorable toxicology and safety pharmacology profile. No test article-related mortality occurred at any dose levels throughout the study. No toxicologically significant changes in clinical chemistry or coagulation were noted throughout the study. None of these changes were noted after the recovery phase.

Test 8: Pharmacokinetics of Crystalline Form A

The fully-validated LC-MS/MS method was well used for the pharmacokinetic (PK) studies of Crystalline Form A of Compound 1 in Sprague-Dawley rats and beagle dogs following single- and multiple-dose administrations.

Crystalline Form A of Compound 1 has good oral bioavailability in rats. It was quickly absorbed and exhibited high plasma clearance (CL) in rats. The kinetics was linear over the dose range in male rats. The linearity in male rats was not as good. There was no statistically significant accumulation of Compound 1 following multiple oral dosing in both male and female rats. Crystalline Form A of Compound 1 exhibited moderate clearance (CL), reasonably good bioavailability (F %), linear PK over the dose range and no accumulation of Compound 1 following multiple oral dosing in dogs.

Test 9: ADME of Crystalline Form A

Compound 1 was widely distributed to various tissues, but was low in brain tissue, indicating the drug does not easily cross the blood-brain barrier.

$IC_{50}$ values of Crystalline Form A of Compound 1 for seven major drug metabolizing CYP isozymes (CYP1A2, CYP2B6, CYP2C8, CYP2C9, CYP2C19, CYP2D6, and CYP3A) were determined in human liver microsomes and the time-dependent inhibition potential on major CYP isozymes of Compound 1 was also evaluated. It showed weak inhibition on CYP2C8 ($IC_{50}$=4.03 μM), CYP2C9 ($IC_{50}$=5.69 μM) and CYP2C19 ($IC_{50}$=7.58 μM), but lower inhibition on other CYP isozymes. Compound 1 is unlikely to be time dependent CYP inhibitors on these 7 major human CYPs. CYP3A is the major CYP isoform responsible for the metabolism in human liver microsomes.

Example 12

Clinical Trail Study (1) Ongoing Clinical Trial Phase 1 Result on Compound 1 in Patients with Advanced B Cell Malignancies The first-in-human multi-center, open-label phase 1 trial of Compound 1 is being conducted in Australia and New Zealand and is comprised of two parts—a dose-escalation phase involving 25 patients and a dose-expansion phase, in which we plan to enroll a total of 100 patients. A total of 39 patients, including all 25 patients from the initial dose-escalation component and 14 patients from the ongoing dose-expansion component were enrolled. Based on the pharmacokinetics, pharmacodynamics, safety and efficacy of Compound 1 in the dose-escalation phase, 320 mg once daily (QD) and 160 mg twice daily (BID) are being further explored in the ongoing dose-expansion trial.

As of Oct. 19, 2015, the cutoff date for data analysis, 29 objective responses have been observed, including 3 complete responses (CRs), 1 very good partial response (VGPR), and 25 partial responses (PRs). Responses by histology are summarized in Table 18. 31 of the 39 patients remain on study treatment, free of progression, including all patients to date who have achieved an objective response.

TABLE 18

Responses by histology of Patients

| | Follow-up Days Median (Range) | Best Response | | | | ORR (CR + PR) |
|---|---|---|---|---|---|---|
| | | CR | PR | SD | PD | |
| Chronic Lymphocytic Leukemia | 220 (83-329) | 0/14 (0%) | 13/14[1] (93%) | 1/14 (7%) | 0 (0%) | 13/14 (93%) |
| Mantle Cell Lymphoma | 148 (84-392) | 2/10 (20%) | 6/10 (60%) | 1/10 (10%) | 1/10 (10%) | 8/10 (80%) |
| Waldenström's Macroglobulinemia | 271 (11-398) | 0/7 (0%) | 6/7[2] (86%) | 0/7 (0%) | 1/7 (14%) | 6/7 (86%) |
| DLBCL | 29 (20-236) | 1/4 (25%) | 0/4 (0%) | 0/4 (0%) | 3/4 (75%) | 1/4 (25%) |
| Indolent NHL | 233 (215-250) | 0/2 (0%) | 0/2 (0%) | 2/2 (100%) | 0/2 (0%) | 0/2 (0%) |
| Hairy Cell Leukemia | 362 | 0/1 (0%) | 1/1 (100%) | 0/1 (0%) | 0/1 (0%) | 1/1 (100%) |
| Burkitt's-like Lymphoma | 84 | 0/1 (0%) | 0/1 (0%) | 0/1 (0%) | 1/1 (100%) | 0/1 (0%) |

[1]Includes five patients with lymphocytosis at latest assessment;
[2]Includes one patient with VGPR
Note:
CR = complete response;
PR = partial response;
SD = stable disease;
PD = progressive disease;
ORR = objective response rate 8 patients discontinued Compound 1, including 6 due to disease progression and 2 due to adverse events related to their underlying malignancy. 3 patients died during study as a result of disease progression or complications of disease progression. There were no drug-related serious adverse events (SAEs). The vast majority of adverse events, regardless of relationship to treatment, were Grade 1 or 2 in severity and not treatment-limiting. Of the 19≥Grade 3 AEs, 4 were assessed by investigators as possibly drug-related—all were self-limited neutropenia, not requiring treatment discontinuation. There was one case of major hemorrhage, defined as a bleeding event grade 3 or higher or an intracranial bleeding event of any grade: GI hemorrhage in a mantle cell lymphoma patient with lymphomatous involvement of the GI tract; this bleeding event occurred during drug hold, and resolved rapidly with re-initiation of Compound 1 treatment, and therefore is not considered to be drug-related. 6 patients had a baseline history of atrial fibrillation/flutter (AF), and no exacerbation or new event of AF was reported.

(2) Ongoing Clinical Trial Phase 1 result on Compound 1 in Patients with Waldenstrom's Macroglobulinemia (WM)

The multi-center, open-label Phase 1 trial of Compound 1 in B-cell malignancies is being conducted in Australia, New Zealand, South Korea, and the United States and consists of a dose-escalation phase and a dose-expansion phase in disease-specific cohorts, which include treatment naive and relapsed/refractory waldenstrom's macroglobulinemia (R/R WM). The dose-escalation component of the trail tested total daily doses ranging from 40 mg to 320 mg, and the ongoing dose-expansion phase is testing doses of 160 mg twice a day (BID) or 320 mg once a day (QD). As of Mar. 31, 2017, 48 patients with WM were enrolled in the study. Responses were determined according to the modified Sixth International Workshop on WM (IWWM) criteria.

Compound 1 was shown to be well tolerated with no discontinuation for Compound 1-related toxicity to date. Adverse events (AEs) were generally mild in severity and self-limited. The most frequent AEs (>10%) of any attribution among 48 patients evaluable for safety were petechiae/purpura/contusion (35%), upper respiratory tract infection (31%), constipation (25%), diarrhea (19%), epistaxis (19%), nausea (17%), cough (15%), anemia (15%), headache (15%), neutropenia (13%), and rash (13%), all of which were grade 1 or 2 in severity except for grade 3 or 4 anemia and neutropenia (8% each) as well as grade 3 or 4 diarrhea and headache (2% each). Five serious AEs were assessed to be possibly related to Compound 1; these included one case each of hemothorax, atrial fibrillation, colitis, febrile neutropenia, and headache. Among AEs of special interest, there were a total of three cases of atrial fibrillation (all grade 1 or 2), and one case of serious hemorrhage (hemothorax), defined as grade 3 or higher hemorrhage or central nervous system hemorrhage of any grade. Three events led to treatment discontinuation: one case each of bronchiectasis, prostate adenocarcinoma, and adenocarcinoma of pylorus.

At the time of the data cutoff, 42 patients were evaluable for response. Patients not evaluable for efficacy included two patients with less than 12 weeks of follow-up, three patients with IgM<500 mg/dl at baseline, and one patient with inaccurate baseline IgM due to cryoprotein. At a median follow-up of 12.3 months (4.4-30.5 months), the ORR was 90% (38/42 patients) and the major response rate was 76% (32/42 patients), with VGPRs in 43% (18/42) of patients and partial responses in 33% (14/42) of patients.

(3) Ongoing Clinical Trial Phase 1 Result on Compound 1 in Patients with Chronic Lymphocytic Leukemia and Small Lymphocytic Lymphoma (CLL/SLL)

The multi-center, open-label Phase 1 trial of Compound 1 in patients with B-cell malignancies is being conducted in Australia, New Zealand, South Korea, and the United States and consists of a dose-escalation phase and a dose-expansion phase in disease-specific cohorts, which include treatment naive (TN) and relapsed/refractory (R/R) CLL/SLL. The dose-escalation component of the trail tested total daily doses between 40 mg and 320 mg, and the ongoing dose-expansion component is testing doses of 160 mg twice a day (BID) or 320 mg once a day (QD). As of Mar. 31, 2017, 69 patients with CLL or SLL (18 TN, 51 R/R) were enrolled in the study.

Compound 1 was shown to be well tolerated in CLL/SLL. The most frequent adverse events (AEs) (≥10%) of any attribution were petechiae/purpura/contusion (46%), fatigue (29%), upper respiratory tract infection (28%), cough (23%), diarrhea (22%), headache (19%), hematuria (15%), nausea (13%), rash (13%), arthralgia (12%), muscle spasms (12%), and urinary tract infection (12%); all of these events were grade 1 or 2 except for one case of grade 3 purpura (subcutaneous hemorrhage), which was the only major bleeding event. Additional adverse events of interest included one case of each grade 2 diarrhea and grade 2 atrial fibrillation. A total of 18 serious AEs (SAEs) occurred in 13 patients, with no SAE occurring in more than one patient. Only one patient discontinued treatment due to an AE, a grade 2 pleural effusion.

At the time of the data cutoff, 66 patients (16 TN and 50 R/R) had more than 12 weeks of follow-up and were evaluable for efficacy, and three other patients had less than 12 weeks of follow-up. After a median follow-up of 10.5 months (2.2-26.8 months), the overall response rate (ORR) was 94% (62/66) with complete responses (CRs) in 3% (2/66), partial responses (PRs) in 82% (54/66), and PRs with lymphocytosis (PR-Ls) in 9% (6/66) of patients. Stable disease (SD) was observed in 5% (3/66) of patients. The patient with pleural effusion discontinued treatment prior to week 12 and was not evaluable for response. There was one instance of Hodgkin's transformation. In TN CLL/SLL, at a median follow-up time of 7.6 months (3.7-11.6 months), the ORR was 100% (16/16) with CRs in 6% (1/16), PRs in 81% (13/16) and PR-Ls in 13% (2/16) of patients. In R/R CLL/SLL, at a median follow-up time of 14.0 months (2.2-26.8 months), the ORR was 92% (46/50) with CRs in 2% (1/50), PRs in 82% (41/50), and PR-Ls in 8% (4/50) of patients. Stable disease was observed in 6% (3/50) patients.

The invention claimed is:

1. A composition comprising:
    (i) a solid amorphous form of Compound 1,

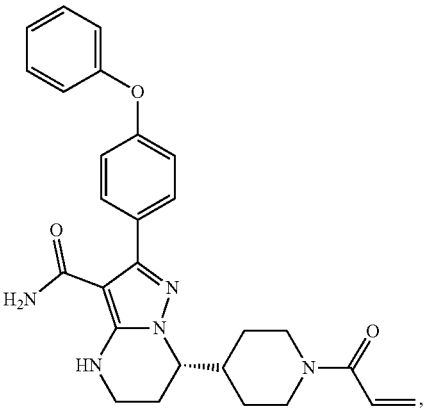

Compound 1 wherein the solid amorphous form has:
    (a) a mid-point temperature of a glass transition temperature of about 79.7° C.; and
    (b) an enantiomeric excess value of at least 97%; and
   (ii) a crystalline form of Compound 1, wherein the crystalline form exhibits an X-ray powder diffraction pattern comprising diffraction peaks having 2θ angle values at 14.8±0.2°, 16.4±0.2° and 21.4±0.2°.

2. The composition of claim 1, wherein the crystalline form has a melting point onset temperature of 139±2° C.

3. The composition of claim 1, wherein the crystalline form has an enantiomeric excess value of at least 45%.

4. The composition of claim 1, wherein the crystalline form has a purity of at least 99.3%.

5. The composition of claim 1, wherein the crystalline form has a purity of at least 99.5%.

6. The composition of claim 1, wherein the crystalline form exhibits an X-ray powder diffraction pattern comprising diffraction peaks having 2θ angle values at 14.8±0.2°, 15.6±0.2°, 16.4±0.2°, and 21.4±0.2°.

7. The composition of claim 1, wherein the crystalline form of Compound 1 is present in about 95% by weight of the composition.

8. The composition of claim 1, wherein the crystalline form of Compound 1 is present in about 99% by weight of the composition.

* * * * *